United States Patent
Choi et al.

(10) Patent No.: US 11,904,021 B2
(45) Date of Patent: Feb. 20, 2024

(54) DUAL TARGETING AND THERAPEUTIC NANOPARTICLE FOR TREATING RENAL FIBROSIS

(71) Applicant: The Chinese University of Hong Kong, Hong Kong (CN)

(72) Inventors: Chung Hang Jonathan Choi, Hong Kong (CN); Cecilia Ka Wing Chan, Hong Kong (CN); Yun Wong James Lau, Hong Kong (CN)

(73) Assignee: THE CHINESE UNIVERSITY OF HONG KONG, Hong Kong (CN)

( * ) Notice: Subject to any disclaimer, the term of this patent is extended or adjusted under 35 U.S.C. 154(b) by 98 days.

(21) Appl. No.: 17/452,041

(22) Filed: Oct. 22, 2021

(65) Prior Publication Data

US 2022/0152220 A1    May 19, 2022

Related U.S. Application Data

(60) Provisional application No. 63/104,262, filed on Oct. 22, 2020.

(51) Int. Cl.
*A61K 47/69* (2017.01)
*A61K 33/242* (2019.01)
*A61K 33/38* (2006.01)
*A61K 33/26* (2006.01)
*A61P 13/12* (2006.01)
*A61K 33/243* (2019.01)
*A61K 47/54* (2017.01)
*A61K 9/51* (2006.01)
*A61K 33/24* (2019.01)

(52) U.S. Cl.
CPC ........ *A61K 47/6929* (2017.08); *A61K 9/5146* (2013.01); *A61K 33/24* (2013.01); *A61K 33/242* (2019.01); *A61K 33/243* (2019.01); *A61K 33/26* (2013.01); *A61K 33/38* (2013.01); *A61K 47/545* (2017.08); *A61P 13/12* (2018.01)

(58) Field of Classification Search
CPC .... A61K 47/6929; A61K 47/545; A61P 13/12
See application file for complete search history.

(56) References Cited

U.S. PATENT DOCUMENTS 8,765,096 B2 * 8/2014 Leamon et al. ....... A61K 51/00

OTHER PUBLICATIONS

DOI: 10.1002/ddr.21545—Folic acid functionalized nanoparticles as pharmaceutical Asghar Narmani1 e Melina Rezvani2 Bagher Farhood3 Parvaneh Darkhor4 Javad Mohammadnejad1 Bahram Amini5 Soheila Refahi6 Nouraddin Abdi Goushbolagh7 (Year: 2019).*

Biochemical Engineeringjournal 89 (2014) 33-41 Engineered drug-protein nanoparticle complexes for folate receptor targeting Dongmei Ren a, Felix Kratz b, Szu-Wen Wanga,* (Year: 2014).*

Folic acid functionalized nanoparticles as pharmaceutical carriers in drug delivery systems Asghar Narmani, Melina Rezvani Bagher Farhood Parvaneh Darkhor Javad Mohammadnejad Bahram Amini Soheila Refahi Nouraddin Abdi Goushbolagh; DOI: 10.1002/ddr.21545 (Year: 2019).*

Engineered drug-protein nanoparticle complexes for folate receptor targeting CrossMark Dongmei Ren a, Felix Kratz b, Szu-Wen Wanga, Biochemical Engineeringjournal 89 (2014) 33-41 (Year: 2014).*

Haidong, W., et al., "Global, regional, and national life expectancy, all-cause morality, and cause-specific mortality for 249 causes of death, 1980-2015: a systematic analysis for the Global Burden of Disease Study 2015," Lancet, 2016, 388: 1459-1544.

Zeisberg, M., et al., "Mechanisms of Tubulointerstitial Fibrosis," Journal of the American Society of Nephrology, 2010, 21:1819-1834.

Williams, R.M., et al., "Nanomedicines for Kidney Diseases," Kidney International Author manuscript, pp. 1-14.

Yang, C.; Nilsson, L.; Cheema, M. U.; Wang, Y.; Frøkiær, J.; Gao, S.; Kjems, J.; Nørregaard, R. Chitosan/SiRNA Nanoparticles Targeting Cyclooxygenase Type 2 Attenuate Unilateral Ureteral Obstruction-Induced Kidney Injury in Mice. Theranostics 2015, 5, 110-123.

Meng, X.- M., et al., "Treatment of renal fibrosis by rebalancing TGF-β/Smad signaling with the combination of asiatic acid and naringenin," Oncotarget, 2015, 6(35):36984-36997.

Dolman, M.E.M., et al., "Drug targeting to the kidney: Advances in the active targeting of therapeutics to proximal tubular cells," Advanced Drug Delivery Reviews, 2010, 62:1344-1357.

Birn, H., "The kidney in vitamin B12 and folate homeostasis: characterization of receptors for tubular uptake of vitamins and carrier proteins," Am J Physiol Renal Physiol, 2006, 291:F22-F36.

Zhao, X., et al., "Targeted drug delivery via folate receptors," Expert Opinion on Drug Delivery, 2008, 5(3):309-319.

Knight, S.F., et al., "Folate Receptor-Targeted Antioxidant Therapy Ameliorates Renal Ischemia-Reperfusion Injury," Journal of the American Society of Nephrology, 2012, 23:793-800.

Sarin, H., "Physiologic upper limits of pore size of different blood capillary types and another perspective on the dual pore theory of microvascular permeability," Journal of Angiogenesis Research, 2010, 2:1-19.

Du, B., et al., "Transport and interactions of nanoparticles in the kidneys," Nature Reviews Materials, 2018, 3:358-374.

Hesketh, E.E., et al., "A Murine Model of Irreversible and Reversible Unilateral Ureteric Obstruction," Journal of Visualized Experiments, 2014, 94:1-6.

Ho, L.W.C., et al., "Nano-Cell Interactions of Non-Cationic Bionanomaterials," Accounts of Chemical Research, 2019, 52:1519-1530.

(Continued)

*Primary Examiner* — Robert A Wax
*Assistant Examiner* — Andre Mach
(74) *Attorney, Agent, or Firm* — Saliwanchik, Lloyd & Eisenschenk

(57) ABSTRACT

The subject invention pertains to compositions and methods for making and use of metal-based coated nanoparticles. The metal-based, PEG-coated nanoparticles of the invention comprise folic acid molecules on their surface exercise dual functionality by specifically targeting renal tubule cells and treating renal fibrosis.

18 Claims, 69 Drawing Sheets

(56) References Cited

OTHER PUBLICATIONS

Yang, H.-C., et al., "Models of chronic kidney disease," Drug Discovery Today: Disease Models, 2010, 7(1-2):13-19.

Liu, Y., "Renal fibrosis: New insights into the pathogenesis and therapeutics," Kidney International, 2006, 69:213-217.

Nogueira, A., et al., "Pathophysiological Mechanisms of Renal Fibrosis: A Review of Animal Models and Therapeutic Strategies," In Vivo, 2017, 31:1-22.

Liu, Y., "Cellular and molecular mechanisms of renal fibrosis," Nature Reviews Nephrology, 2011, 7:684-696.

Chaar, M.E., et al., "Effect of combination therapy with enalapril and the TGF-β antagonist 1D11 in unilateral ureteral obstruction," Am J Physiol Renal Physiol, 2007, 292:F1291-F1301.

Gao, X., et al., "Hepatocyte growth factor gene therapy retards the progression of chronic obstructive nephropathy," Kidney International, 2002, 62:1238-1248.

Lan, H.U., et al., "Inhibition of Renal Fibrosis by Gene Transfer of Inducible Smad7 Using Ultrasound-Microbubble System in Rat UUO Model," Journal of the American Society of Nephrology, 2003, 14:1535-1548.

He, W., et al., "Wnt/β-Catenin Signaling Promotes Renal Interstitial Fibrosis," Journal of the American Society of Nephrology, 2009, 20:765-776.

Tan, R.J., et al., "Wnt/β-catenin signaling and kidney fibrosis," Kidney International Supplements, 2014, 4:84-90.

Huo, S., et al., "Ultrasmall Gold Nanoparticles Behavior in Vivo Modulated by Surface Polyethylene Glycol (PEG) Grafting," Bioconjugate Chemistry, 2017, 28:239-243.

Piella, J., et al., "Size-Controlled Synthesis of Sub-10-nanometer Citrate-Stabilized Gold Nanoparticles and Related Optical Properties," Chemistry of Materials, 2016, 28:1066-1075.

Bastus, N.G., et al., "Kinetically Controlled Seeded Growth Synthesis of Citrate-Stabilized Gold Nanoparticles of up to 200 nm: Size Focusing versus Ostwald Ripening," Langmuir, 2011, 27:11098-11105.

Haiss, W., et al., "Determination of Size and Concentration of Gold Nanoparticles from UV-Vis Spectra," Analytical Chemistry, 2007, 79(11):4215-4221.

Hurst, S.J., et al., "Maximizing DNA Loading on a Range of Gold Nanoparticle Sizes," Analytical Chemistry, 2006, 78(24):8313-8318.

Ho, L.W.C., et al., "Effect of Alkylation on the Cellular Uptake of Polyethylene Glycol-Coated Gold Nanoparticles," ACS Nano, 2017, 11:6085-6101.

Chevalier, R.L., et al., "Ureteral obstruction as a model of renal interstitial fibrosis and obstructive nephropathy," Kidney International, 2009, 75:1145-1152.

Takemoto, M., et al., "A New Method for Large Scale Isolation of Kidney Glomeruli from Mice," American Journal of Pathology, 2002, 161(3):799-805.

Kah, J.C.Y., et al., "Molecular contrast of EGFR expression using gold nanoparticles as a reflectance-based imaging probe," Molecular and Cellular Probes, 2008, 22:14-23.

Yamashita, S., "Heat-induced antigen retrieval: Mechanisms and application to histochemistry," Progress in Histochemistry and Cytochemistry, 2007, 41:141-200.

Veenstra, D.L., et al., "Incidence and Long-Term Cost of Steroid-Related Side Effects After Renal Transplantation," American Journal of Kidney Diseases, 1999, 33(5):829-839.

Fried, L.F., "Combined Angiotensin Inhibition for the treatment of Diabetic Nephropathy," The New England Journal of Medicine, 2013, 369:1892-1903.

Choi, C.H.J., et al., "Targeting kidney mesangium by nanoparticles of defined size," PNAS, 2011, 108(16):6656-6661.

Zuckerman, J.E., et al., "Polycation-siRNA nanoparticles can disassemble at the kidney glomerular basement membrane," PNAS, 2012, 109(8):3137-3142.

Huang, Y., et al., "The effect of size, charge, and peptide ligand length on kidney targeting by small, organic nanoparticles," Bioengineering & Translational Medicine, 2020, 5:1-11.

Williams, R.M., et al., "Selective Nanoparticle Targeting of the Renal Tubules," Hypertension, 2018, 71(1):1-17.

Du, B., et al., "Glomerular barrier behaves as an atomically precise bandpass filter in a sub-nanometre regime," Nature Nanotechnology, 2017, 12:1-9.

Kamaly, N., et al., "Nanomedicines for renal disease: current status and future applications," Nature Reviews Nephrology, 2016, 12:738-753.

Wang, J., et al., "Oral delivery of metformin by chitosan nanoparticles for polycystic kidney disease," Journal of Controlled Release, 2021, 329:1198-1209.

Huang, C. et al., "Folate Receptor-Mediated Renal-Targeting Nanoplatform for the Specific Delivery of Triptolide to Treat Renal Ischemia/Reperfusion Injury," ACS Biomater. Sci. Eng., 2019, 5:2877-2886.

Zhang, Y.-N., et al., "Nanoparticle-liver interactions: Cellular uptake and hepatobiliary elimination," Journal of Controlled Release, 2016, 240:332-348.

Choi, H.S., et al., "Renal clearance of quantum dots," Nature Biotechnology, 2007, 25(10):1165-1170.

Wu, Z., et al., "Solubility of Folic Acid in Water at pH Values between 0 and 7 at Temperatures (298.15, 303.15, and 313.15) K," Journal of Chemical & Engineering Data, 2010, 55(9):3958-3961.

Nestor, J., et al., "Lupus antibodies induce behavioral changes mediated by microglia and blocked by ACE inhibitors," Journal of Experimental Medicine, 2018, 215(10):2554-2566.

Keppler, A., et al., "Plasma creatinine determination in mice and rats: An enzymatic method compares favorably with a high-performance liquid chromatography assay," Kidney International, 2007, 71:74-78.

Dunnett, C.W., "A Multiple Comparison Procedure for Comparing Several Treatments with a Control," Journal of the American Statistical Association, 1955, 50(272):1096-1121.

Yin, B., et al., "Intrapulmonary Cellular-Level Distribution of Inhaled Nanoparticles with Defined Functional Groups and Its Correlations with Protein Corona and Inflammatory Response," ACS Nano, 2019, 13:14048-14069.

Cobley, C.M., et al., "Gold nanostructures: a class of multifunctional materials for biomedical applications," Chem. Soc. Rev., 2011, 40:44-56.

Ucero, A.C., et al., "Unilateral ureteral obstruction: beyond obstruction," Int Urol Nephrol, 2014, 46:765-776.

Forbes, M.S., et al., "Fight-or-flight: murine unilateral ureteral obstruction causes extensive proximal tubular degenernation, collecting duct dilation, and minimal fibrosis," Am J Physiol Renal Physiol, 2012, 303:F120-F129.

Malyala, P., et al., "Endotoxin Limits in Formulations for Preclinical Research," Journal of Pharmaceutical Sciences, 2008, 97(6): 2041-2044.

Jiang, D., et al., "Nanomedicines for Renal Management: From Imaging to Treatment," Accounts of Chemical Research, 2020, 53:1869-1880.

\* cited by examiner

FIG. 1A
FIG. 1B
FIG. 1C
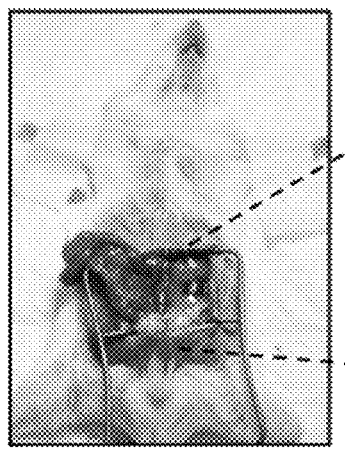
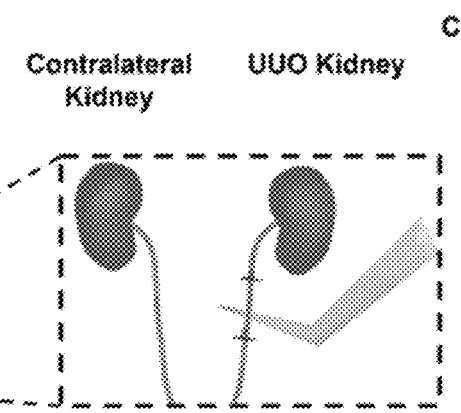
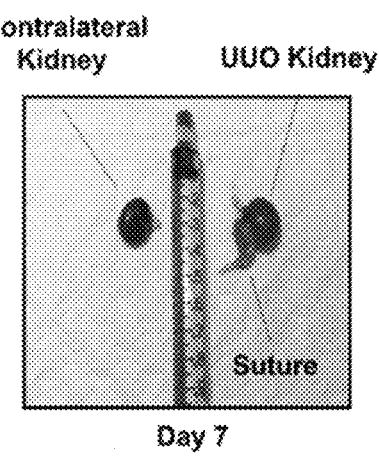
FIG. 2
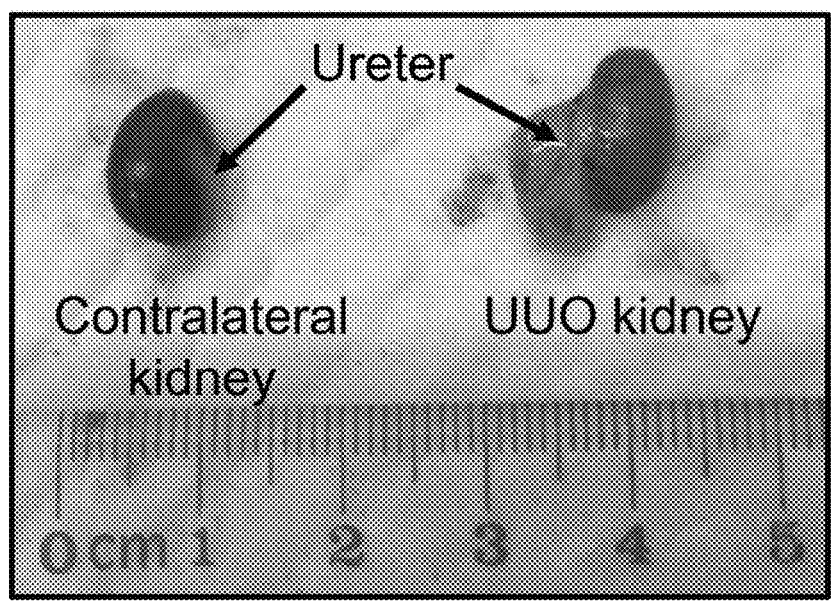

$Au_x$-$PEG_y$ NP

Au$_3$-PEG$_{500}$-FA$_{32}$ NP

Healthy mice ■ UUO 7 days

Au5-PEG$_{1000}$ NPs

Healthy mice ■ UUO 7 days

DUAL TARGETING AND THERAPEUTIC NANOPARTICLE FOR TREATING RENAL FIBROSIS

CROSS-REFERENCE TO RELATED APPLICATION

This application claims the benefit of U.S. Patent Application Ser. No. 63/104,262, filed Oct. 22, 2020, which is hereby incorporated by reference in its entirety including any tables, figures, or drawings.

BACKGROUND OF THE INVENTION

Chronic kidney disease (CKD) is an emergent global disease, with approximately 1.2 million people died from kidney failure in 2015, an increase of 32% from 2005[1]. Renal fibrosis, a common pathway in CKD, affects about 10% of the adult population worldwide. Independent of the various initial cause, renal fibrosis is the final common pathway in CKD that can lead to renal failure[2]. Unfortunately, there is no effective treatment for preventing the progression of renal fibrosis, and the development of a precise therapeutic strategy will be key in addressing unmet challenges in the management of CKDs. The major challenge for targeted therapy against kidney fibrosis is to design a delivery system that can reach the kidney, without being cleared too rapidly to achieve a therapeutic effect[3].

Several studies explored the application NPs for the treatment of CKD[4-5]. However, they primarily used nanomedicines as a preventive treatment, where the animals were treated with the nanomedicine before the induction of renal fibrosis and did not address whether nanomedicines could affect renal fibrosis after it is established in the kidneys. The distinction between kidney fibrosis prevention and kidney fibrosis treatment is clinically significant because most treatment involving kidney fibrosis to date are only capable of preventing fibrosis or preventing further fibrosis in the kidney but are not able to treat or reduce the fibrosis already present in a fibrotic kidney. Further, previous nanomedicine designs contained one agent for targeting a kidney cell and a separate agent for treatment of a kidney disease increasing production cost, decreasing production efficiency and harboring the potential of off-target effects.

Nanoparticles (NPs) are promising drug carriers to the kidneys because they can be made small enough[35] to traverse membrane barriers and their surface charge[36,37] and dosage[38] can be easily tailored. In healthy kidneys, plasma fluid is filtered across the kidney glomerular filtration barrier (GFB) to form urine. Filtration is achieved through endothelium fenestrations (~60-70 nm) lining the glomerular capillaries, pores (5-8 nm) in the glomerular basement membrane and gaps (3-4 nm) from the slit diaphragm of podocytes that envelope the capillaries in the GFB (FIGS. 9B-9C)[39]. To treat renal fibrosis in CKD, NPs must be <10 nm to cross the GFB before reaching the kidney tubules (major site of renal fibrosis)[40]. Studies have shown polymeric NPs (≥100 nm) loaded with siRNA[4] and small molecules[41] are effective for treating CKD. Others have exploited overexpressed folate receptors (FR) on apical membranes of kidney tubular cells[6,7] to localize NPs (~100 nm) in tubules[42]. However, these large NPs are non-specifically cleared by the liver[43] and must disassemble to cross the GFB[42,20], making them inefficient and unpredictable for targeted delivery. While sub-10 nm NPs can bypass the liver and clear through the kidneys following intravenous (i.v.) injection in healthy animals[44], the size threshold for crossing the GFB in mice with kidney disease is unknown.

Therefore, new compositions that treat, and not only prevent, kidney fibrosis, are more efficiently produced, and have low off-target effects are urgently needed.

BRIEF SUMMARY OF THE INVENTION

Provided are compositions and methods of making and using them for simultaneous targeting of renal tubal cells and treating of renal fibrosis using a single combined targeting and treating bionanomaterial. Specifically, the combination targeting and treating compositions of the invention comprise selective compounds that function as a dual targeting ligand of renal tubules and a therapeutic moiety against fibrosis.

In some embodiments, a dual function bionanomaterial for the treatment of kidney fibrosis is provided. The dual function bionanoparticle of the invention comprises a nanoparticle comprising a metal core; at least one polymer; and at least one dual function targeting and therapeutic molecule.

The metal core of the dual function bionanoparticle of the invention can comprise gold, silver, nickel, iron or platinum. The at least one polymer of the dula function bionanoparticle can comprise at least one of poly(ethylene glycol), poly(ethylene oxide), poly(lactic acid), poly(glycolic acid), poly(ethylene oxide)-poly(lactic acid), poly(ethylene oxide)-poly(glycolic acid), poly(glycolic acid)-poly(lactic acid), sodium alginate, dextran, poloxamers, or combiations thereof.

In preferred embodiments, the at least one dual function targeting and therapeutic molecule of the nanoparticle of the invention is selected from folic acid, folate, dihydrofolate, tetrahydrofolate, 10-formyl, 5,10-methylene, and 5-methyl substituted folate.

In further preferred embodiments, the at least one dual function targeting and therapeutic molecule is at least one folic acid molecule that is present on the surface of the nanoparticle.

In more preferred embodiments, the dual function bionanomaterial of the invention comprises 8, 16 or 32 folic acid molecules that are present on the surface of each nanoparticle.

Further provided are methods of treating kidney diseases in subjects, which methods comprise administering at least one therapeutically effective amount of a dual function bionanomaterial of the invention to the subject.

In preferred embodiments, a dual function bionanomaterial of the invention is administered to the subject, which bionanomaterial comprises folic acid, PEG-coated gold nanoparticles (FA-PEG NPs). Advantageously, the FA-PEG AuNPs of the invention are selectively and highly efficiently excreted in the glomerular filtrate and taken up by tubular renal cells through folate receptors. Further, advantageously, the FA-PEG AuNPs following tubule cell uptake inhibit the expression of kidney fibrosis-promoting molecules and, thereby, treat kidney fibrosis.

The dual function bionanomaterials do not accumulate in or cause damage to other organs following systemic administration. Further, the dual function bionanomaterials are efficiently and cost-effectively produced, are stable following systemic administration and efficiently reduces the area of renal fibrosis.

In certain embodiments, sub-10 nm NPs conjugated with folic acid (FA) can cross the glomerular filtration barrier (GFB) effectively and prevent the progression of kidney fibrosis. In certain embodiments, 3 nm diameter gold (Au)

NPs conjugated with a shell of 500 Da polyethylene glycol (PEG) strands and ~32 FA molecules ($Au_3$—$PEG_{500}$-$FA_{32}$ NPs) can cross the GFB and bind to a folate receptor (FR) in fibrotic renal tubules. In certain embodiments, upregulation of the folate receptor can occur upon administration of sub-10 nm NPs conjugated with FA to patients with renal fibrosis. In certain embodiments, a single injection of sub-10 nm NPs conjugated with FA can prevent tissue degeneration and reduce fibrosis more effectively than Captopril (a conventional ACE inhibitor for treating CKD) in 7 days, without inducing toxicity.

BRIEF DESCRIPTION OF THE DRAWINGS

FIG. 1A shows the surgical site of the Unilateral Urethral Obstruction (UUO) surgery.

FIG. 1B shows a schematic of the double suture of the left ureter leading to complete obstruction. FIG. 1C shows the swelling (hydronephrosis) of the left kidney following urine buildup observed on Day 7 post-UUO surgery.

FIG. 2 shows the gross anatomy of the UUO kidney and the corresponding contralateral (CL) kidney.

FIG. 9B (right), Schematic illustrating the glomerular filtration barrier (GFB) consists of endothelial fenestrations, pores in the glomerular basement membrane (GBM) and gaps from podocytes. Intravenously injected NPs must penetrate GFB to reach the renal tubules where fibrosis occurs, but the size threshold for crossing GBM in CKD kidneys is currently unknown.

FIG. 13A, Schematic of a $Au_3$-$PEG_{500}$-$FA_{32}$ NP engaging folate receptors (FR) that are overexpressed on the lumen side of a tubule cell. FIG. 13B, Organ-level distribution of Au$_3$-PEG$_{500}$-FA$_{32}$ and Au$_3$—PEG$_{500}$ NPs in UUO and CL kidneys 24 h post-injection show enhanced accumulation of Au$_3$-PEG$_{500}$-FA$_{32}$ NPs in UUO kidneys. % ID=percentage of injected dose. Data are from n=6, across 2 experiments. FIG. 13C shows the expression of folate receptor (FR) in UUO kidneys and normal kidneys by immunohistochemistry. FIG. 13D, IHC staining shows that the elevated expression of FR (brown) in selected tubule cells in UUO kidney is distinct from the homogenous FR expression in healthy and CL kidneys. Representative images from n=3 kidney sections from 3 mice/group. FIG. 13E, IHC staining of kidney biopsies from patients with varying degrees of fibrosis show fibrotic tubules had higher expression of FR (brown) than their adjacent healthy tissues. Representative images from n=2 kidney sections from each group. FIG. 13F shows the tissue-level distribution of Au$_3$-PEG$_{500}$-FA$_{32}$ NPs in the UUO kidney by silver enhancement staining. FIG. 13G shows representative light micrographs of silver-enhanced kidney sections showing the localization of NPs in the renal cortex. Dark brown or black signals indicate the location of AuNPs. FIG. 13H shows the tissue-level distribution of Au$_3$-PEG$_{500}$-FA$_z$ NPs by confocal reflectance microscopy with the colocalization of Au$_3$-PEG$_{500}$-FA$_{32}$ NPs (green) with folate receptors (brown) being higher than that of Au$_3$-PEG$_{500}$ NPs with Folate receptors. FIG. 13I, Targeted Au$_3$-PEG$_{500}$-FA$_{32}$ NPs accumulated significantly in the tubules and interstitial space of UUO kidney 24 h post-injection. Data are from n=6, across 2 experiments. For FIG. 13I, statistical significance was evaluated using One-Way ANOVA with Tukey's post hoc test for multiple comparison. All p values less than or equal to 0.05 are displayed as * p<0.05,  p<0.01, * p<0.001, ****p<0.0001. P values that are not significant are not displayed. All bars and error bars represent mean±SD.

FIG. 24A, UUO mice were treated with one intravenous dose of either Au$_3$-PEG$_{500}$-FA$_{32}$, Au$_3$—PEG$_{500}$ NPs, saline or free FA on Day 7 and a daily intraperitoneal injection of Captopril from Day 7 before they were sacrificed at Day 14. FIG. 24B, Gross appearance of a healthy kidney and a CL kidney from UUO mice. FIG. 24C, Only UUO kidneys of animals treated with Au$_3$-PEG$_{500}$-FA$_{32}$ NPs and free FA did not degenerate. FIG. 24D, Representative histological images of UUO kidneys show mice treated with Au$_3$-PEG$_{500}$-FA$_{32}$ NPs had the least tubule injury (black arrows). Black circle indicates an intact tubule. Representative images from n=3 kidney sections from 9 mice/group. FIG. 24E, Mice treated with Au$_3$-PEG$_{500}$-FA$_{32}$ NPs had significantly higher UUO kidney-to-body weight ratio at point of sacrifice (Day 14) than those treated with saline and Au$_3$—PEG$_{500}$ NPs. Data are from n=9, across 2 experiments. FIG. 24F, Blood creatinine in UUO mice treated with Au$_3$-PEG$_{500}$-FA$_{32}$ NPs and free FA were cleared more rapidly than those treated with saline, Captopril or Au$_3$—PEG$_{500}$ NPs. Data are from n=9, across 3 experiments. For FIGS. 24E-24F, statistical significance was evaluated using One-Way ANOVA with Tukey's post hoc test for multiple comparison. All p values less than or equal to 0.05 are displayed as * p<0.05. P values that are not significant are not displayed. All bars and error bars represent mean±SD.

FIG. 27A, IHC analysis of type I collagen expression in the same UUO kidneys harvested for RNA-seq 48 h post-injection. Both Au$_3$-PEG$_{500}$-FA$_{32}$ NP and free FA groups show lower type I collagen protein expression than saline group. Data are from n=3, across 1 experiment. Statistical significance was evaluated using One-Way ANOVA with Tukey's post hoc test for multiple comparison. P values that are not significant are not displayed. All bars and error bars represent mean±SD. FIG. 27B, Venn diagram of differentially expressed gene (DEGs) identified in pairwise comparisons between the three treatment groups (Q value <0.05). Number in the overlapping region between two or more circles indicate the number of DEGs that are shared between the pairwise comparisons. Note that "Group X vs. Group Y" indicates statistically significant changes in RNA expression that were found in Group Y with reference to Group X as baseline. There are 169 DEGs commonly identified in the "saline vs. Au$_3$—PEG$_{500}$-FA$_{32}$ NP" and "free FA vs. Au$_3$—PEG$_{500}$-FA$_{32}$ NP" pairwise comparisons (marked with red border in Venn diagram). FIG. 27C, Of the 169 DEGs identified in both pairwise comparisons, 19 of them have FPKM values >2 for at least 6 out of the 9 UUO kidneys analyzed by RNA-seq.

FIG. 31A, Heat map of normalized transcript expression from the Au$_3$-PEG$_{500}$-FA$_{32}$ NP group with reference to the saline group as baseline (saline vs. Au$_3$-PEG$_{500}$-FA$_{32}$ NP). FIG. 31B, Heat map of normalized gene expression from the free FA group with reference to the saline group as baseline (saline vs. free FA). FIG. 31C, Heat map of normalized transcript expression from the Au$_3$-PEG$_{500}$-FA$_{32}$ NP group with reference to the free FA group as baseline (free FA vs. Au$_3$-PEG$_{500}$-FA$_{32}$ NP). The horizontal axis shows the normalized expression [fragments per kilobase million (FPKM) value of each transcript. The vertical axis shows the detected transcripts in triplicates.

FIG. 32A, biological processes, FIG. 32B, cellular component, and FIG. 32C, molecular function. (Q<0.05).

FIG. 33A, biological processes, FIG. 33B, cellular component, and FIG. 33C, molecular function. (Q<0.05).

FIG. 34A, biological processes, FIG. 34B, cellular component, and FIG. 34C, molecular function. (Q<0.05).

DETAILED DISCLOSURE OF THE INVENTION

Figure 3:
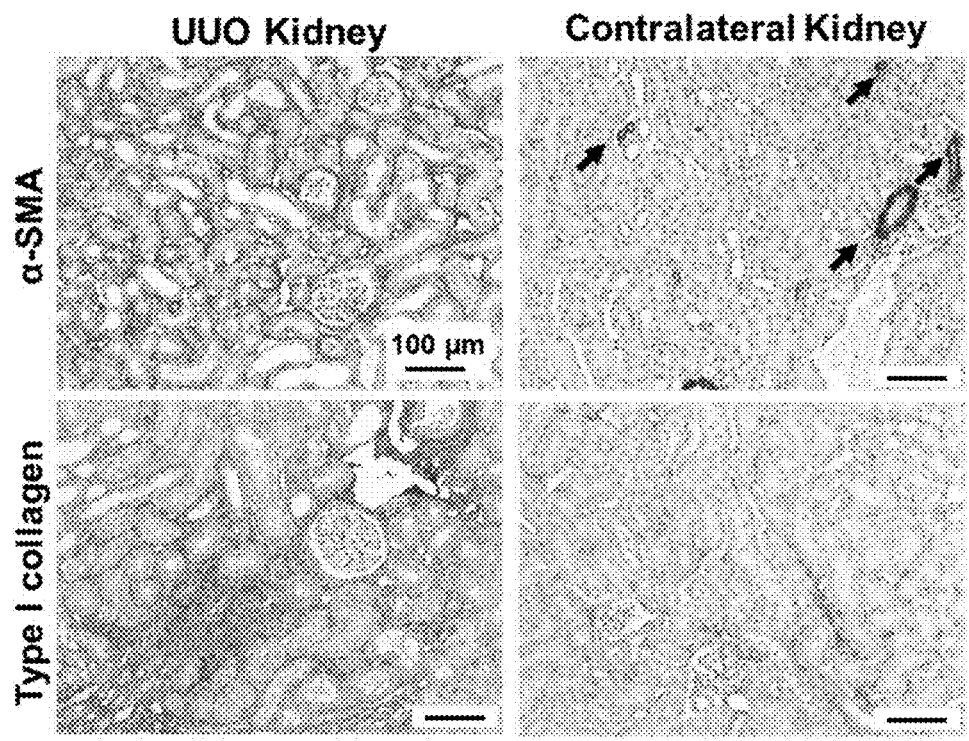
FIG. 3 shows the IHC staining of UUO kidneys (left) and contralateral kidneys (right) using antibodies against α-smooth muscle (top) and type I collagen (bottom) at day 7 after the UUO surgery. The black arrows indicate smooth muscle cells that line the blood vessel walls.

Provided are compounds and compositions for targeting renal tubule cells and treating renal fibrosis. Advantageously, the compounds and compositions of the invention comprise a single agent for renal tubule cell targeting and treatment of renal fibrosis. The single targeting and therapeutic agent is part of the structure of a metal-based nanoparticle. In preferred embodiments, the single targeting and therapeutic agent is exposed on the surface of the metal-based nanoparticle. In some embodiments, the single targeting and therapeutic agent is integrated within the metal-based nanoparticle and becomes exposed on the surface of said nanoparticle upon delivery.

The metal-based nanoparticle of the invention comprises a metal including, but not limited to, gold, silver, nickel, iron, and platinum. In preferred embodiments, the nanoparticle of the invention is a gold nanoparticle.

The metal nanoparticle of the invention also comprises one or more biocompatible polymers. In some embodiments, the metal nanoparticle of the invention is coated with at least one biocompatible polymer. The at least one polymer can be derived from poly(ethylene glycol), poly(ethylene oxide), poly(lactic acid), poly(glycolic acid), poly(ethylene oxide)-poly(lactic acid), poly(ethylene oxide)-poly(glycolic acid), poly(glycolic acid)-poly(lactic acid), sodium alginate, dextran, poloxamers, or any combinations thereof. The metal nanoparticle of the invention can comprise mixtures of at least two polymers in ratios including, but not limited to, ratios of about 0.1:99.9; about 0.5:99.5; about 1:99; about 1.5:98.5; about 2:98; about 5:95; about 7.5:92.5; about 10:90; about 12.5:87.5; about 15:85; about 17.5:82.5; about 20:80; about 22.5:77.5; about 25:75; about 27.5:72.5; about 30:70; about 32.5:67.5; about 35:65; about 37.5:62.5; about 40:60; about 42.5:57.5; about 45:55; about 50:50. In some embodiments, the mixtures of polymers comprise equal amounts of at least three polymers. In some embodiments, the mixtures of polymers comprise different amount of at least three polymers with each polymer comprising from about 1% to about 97% of the total amount of polymers and any % amounts in between.

In some embodiments, the metal nanoparticle of the invention is coated with PEG molecules comprising at least 16 units. In further embodiments, the number of units per each PEG molecules of the nanoparticles of the invention include, but are not limited to, 32, 48, 64, 80, 96, 112, 128, 144, 160, 176, 192, 208, 224, and 240 units. In some embodiments, the PEG molecules of the nanoparticles of the invention comprise a molecular weight of at least 200 Da, 400 Da, 500 Da, 600 Da, 800 Da, 1000 Da, 1500 Da, 2000 Da, 2500 Da, 3000 Da, 3500 Da, 4000 Da, 4500 Da, 5000

Da, 5500 Da, or 6000 Da, 6500 Da, 7000 Da, 7500 Da, 8000 Da, 8500 Da, 9000 Da, 9500 Da, 10000 Da, 15000 Da, and 20000 Da.

In preferred embodiments, the PEG molecules of the nanoparticles of the invention comprise a molecular weight of at least 200 Da, 500 Da, 1000 Da, 2000 Da, or 5000 Da.

In some embodiments, the PEG molecules of the metal nanoparticles of the invention are linear. In some embodiments, the PEG molecules of the metal nanoparticles of the invention are branched.

In some embodiments, the PEG molecules of the metal nanoparticles of the invention are functionalized. In some embodiments, the PEG are mono-, di- or multi-functionalized with different functional groups including, but not limited to, methoxy, amino, carboxyl, hydroxyl, thiol, bromyl moieties.

The PEG-coated nanoparticles of the invention can comprise different numbers of PEG strands per nanoparticles. For example, the PEG-coated metal nanoparticles of the invention can comprise from about 50 PEG strands to about 5000 PEG strands per nanoparticle. In some embodiments, the nanoparticles comprise about 55 to about 4500; from about 60 to about 4000; from about 65 to about 3500; from about 70 to about 3000; from about 75 to about 2500; from about 80 to about 2000; from about 85 to about 1800; from about 90 to about 1600; from about 95 to about 1400; from about 100 to about 1200; from about 120 to about 1000; about 140 to about 800; about 160 to about 700; about 180 to about 600; and from about 200 to about 400 PEG strands per nanoparticle.

In preferred embodiments, the nanoparticles of the invention comprise about 500 to about 5000 PEG strands per nanoparticle.

In some embodiments, the gold nanoparticles (AuNPs) of the invention are synthesized via the reduction of tetrachloroauric by sodium citrate. In some embodiments, AuNPs of the invention are synthesized via reduction of tetrachloroauric by sodium citrate and tannic acid. In preferred embodiments, PEG-coated AuNPs are synthesized using tetrachloroauric acid, methoxy- and thiol-terminated PEG (monomethoxy-poly(ethylene glycol), $mPEG_{200}$-SH) and sodium borohydride. The core diameter of NPs thus synthesized preferably is about 2 nm.

In further preferred embodiments, AuNPs with a core diameter of about 3 nm are synthesized using tetrachloroauric, sodium citrate, tannic acid, and potassium carbonate. In some preferred embodiments, PEG-coated AuNPs with a core diameter of about 5 nm are synthesized using AuNPs of 3 nm core diameter, tetrachloroauric, and sodium citrate.

In some preferred embodiments, PEG-coated AuNPs are synthesized using a seed-mediated growth method. To this end, AuNPs seeds are synthesized using tetrachloroauric and sodium citrate. In preferred embodiments, a seed AuNPs of a core size of about 8 nm is generated and further incubated in several cycles with tetrachloroauric and sodium citrate until an AuNPs of the desired size of about 20 nm is reached.

In some embodiments, the core size of the NPs of the invention is from about 2 nm to about 50 nm. In some embodiments, the NP core size is from about 2.2 nm to about 45 nm; from about 2.5 nm to about 40 nm; from about 2.7 nm to about 35 nm; from about 3 nm to about 30 nm; from about 3.2 nm to about 28 nm; from about 3.5 nm to about 25 nm; from about 3.7 nm to about 22 nm; from about 4 nm to about 20 nm; from about 4.2 nm to about 43 nm; from about 4.5 nm to about 16 nm; from about 4.7 nm to about 14 nm; from about 5 nm to about 12 nm; from about 5.2 nm to about 10 nm; from about 5.5 nm to about 8 nm; from about 5.7 nm to about 7 nm.

In some embodiments, the hydrodynamic diameter of the nanoparticle of the instant invention is from about 1 nm to about 100 nm; from about 2 nm to about 95 nm; from about 3 nm to about 90 nm; from about 4 nm to about 85 nm; from about 5 nm to about 80 nm; from about 6 nm to about 75 nm; from about 7 nm to about 70 nm; from about 8 nm to about 65 nm; from about 9 nm to about 60 nm; from about 10 nm to about 55 nm; from about 11 nm to about 50 nm; from about 12 nm to about 45 nm; from about 13 nm to about 40 nm; from about 14 nm to about 35 nm; from about 15 nm to about 30 nm; from about 16 nm to about 25 nm; from about 17 nm to about 20 nm.

In preferred embodiments, the hydrodynamic diameter of the nanoparticle of the invention is from about 2 nm to about 60 nm. In further preferred embodiments, the hydrodynamic diameter of the nanoparticle of the invention is from about 5 nm to about 50 nm. In most preferred embodiments, the hydrodynamic diameter of the nanoparticles of the invention is above 10 nm. Advantageously, the nanoparticles of the invention with a diameter of more than 10 nm accumulate preferentially in the urine of a subject and are taken up efficiently by renal tubule cells of said subject.

In preferred embodiments, citrate-capped AuNPs of the invention are functionalized with thiolated methoxy PEG including, but not limited to, $mPEG_{200}$-SH, $mPEG_{500}$-SH, $mPEG_{1000}$-SH, and $mPEG_{5000}$-SH.

In some embodiments, the thiolated PEG is used at a concentration from about 1 to about 50 molecules per $nm^2$, including about 2 to about 45 molecules; about 4 to about 40 molecules; about 3 to about 35 molecules; about 4 to about 30 molecules; about 5 to about 25 molecules; about 6 to about 400 molecules; about 17 to about 300 molecules; about 17 to about 200 molecules; about 18 to about 100 molecules; about 19 to about 90 molecules; about 20 to about 80 molecules; about 21 to about 70 molecules; about 22 to about 60 molecules; about 23 to about 50 molecules; about 24 to about 45 molecules; and about 25 to about 40 molecules per $nm^2$.

In preferred embodiments, the thiolated PEG is used at a concentration of 10 PEG molecules per $nm^2$ of NP surface.

In some embodiments, the PEG-coated metal nanoparticles of the invention are coated with a compound selected from folic acid (FA), folate, dihydrofolate, tetrahydrofolate and substituted folate including, but not limited to, 10-formyl, 5,10-methylene, and 5-methyl substituted folate.

In some embodiments, the folic acid (FA)-terminated, PEG-coated AuNPs are synthesized by replacing $mPEG_{200}$-SH, $mPEG_{500}$-SH, $mPEG_{1000}$-SH, and $mPEG_{5000}$-SH with $FA-PEG_{200}$-SH, $FA-PEG_{500}$-SH, $FA-PEG_{1000}$-SH, and $FA-PEG_{5000}$-SH.

In preferred embodiments, folic acid (FA)-terminated, PEG-coated AuNPs are synthesized using PEG-coated AuNPs of a core diameter of about 3 nm and substituting $mPEG_{500}$-SH, $mPEG_{1000}$-SH, and $mPEG_{5000}$-SH with $FA-PEG_{500}$-SH, $FA-PEG_{1000}$-SH, and $FA-PEG_{5000}$-SH.

In further preferred embodiments, FA-terminated, PEG-coated AuNPs of 3 nm in core diameter are synthesized using the methods of the invention and substituting $mPEG_{500}$-SH with $FA-PEG_{500}$-SH.

In yet further preferred embodiments, FA-terminated, PEG-coated AuNPs of 5 nm in core diameter are synthesized using the methods of the invention and substituting $mPEG_{1000}$-SH with $FA-PEG_{1000}$-SH.

In specific embodiments, the AuNPs of the invention comprise PEG molecules of at least 200 Da to ensure solubilization of FA.

In further embodiments, citrate-capped AuNPs of 3 nm in diameter with different mixing ratios of FA-PEG$_{500}$-SH to mPEG$_{500}$-SH are used keeping the total PEG loading constant at a concentration of 10 PEG molecules per nm$^2$ of NP surface. The mixing ratios of mPEG$_{500}$-SH and FA-PEG$_{500}$-SH include, but are not limited to, 1:0 for Au-PEG NP, 3:1 for Au-PEG-FA¼ NPs (25% of the maximal amount of FA on the NP), 1:1 for Au-PEG-FA½ NPs (50% of the maximal amount of FA on the NP), and 0:1 for Au-PEG-FA NPs (100% of the maximal amount of FA on the NP). In further embodiments, AuNPs comprise from about 0.5% to about 99% of FA on the NP surface and from about 1% to about 95%; about 2% to about 90%; about 5% to about 85%; about 10% to about 80%; about 15% to about 75%; about 20% to about 70%; about 25% to about 65%; about 30% to about 60%; about 35% to about 55%; or about 40% to about 50%.

In some embodiments, the FA-terminated PEG coated AuNPs of the invention comprise different numbers of FA molecules per NP. For example, the number of FA molecules on each NP can be from 1 to 500 including, but not limited to, 2, 5, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 42, 44, 46, 48, 50, 52, 54, 56, 58, 60, 62, 64, 66, 68, 70, 75, 80, 85, 90, 95, 99 and from about 2 to about 490; about 3 to about 480; about 5 to about 470; about 7 to about 460; about 8 to about 450; about 9 to about 440; about 10 to about 430; about 11 to about 430; about 12 to about 420; about 13 to about 410; about 14 to about 400; about 15 to about 390; about 16 to about 380; about 17 to about 370; about 18 to about 360; about 19 to about 350; about 20 to about 340; about 21 to about 330; about 22 to about 320; about 23 to about 3100; about 24 to about 300; about 25 to about 290; about 26 to about 280; about 27 to about 270; about 28 to about 260; about 29 to about 250; about 30 to about 240; about 31 to about 230; about 32 to about 220; about 33 to about 210; about 34 to about 200; about 35 to about 190; about 36 to about 180; about 37 to about 170; about 38 to about 160; about 39 to about 150; about 40 to about 145; about 42 to about 140; about 44 to about 135; about 46 to about 130; about 48 to about 125; about 50 to about 120; about 52 to about 115; about 54 to about 110; about 56 to about 105; about 58 to about 100; about 60 to about 95; about 62 to about 90; about 64 to about 85; about 66 to about 80; about 68 to about 75; or about 70 to about 72.

In preferred embodiments, the FA-terminated, PEG-coated AuNPs of the invention comprise 8, 16, or 32 FA molecules on each NP.

In further preferred embodiments, the FA-terminated, PEG-coated AuNPs of the invention comprise 32 FA molecules on each NP. In the most preferred embodiments, the NPs of the invention are Au$_3$—PEG$_{500}$-FA$_{32}$ NPs.

Also provided are methods of using the dual targeting and therapeutic compositions of the invention to treat renal tubule-mediated diseases including, but not limited to, renal fibrosis.

In specific embodiments, several applications of the compositions of the invention are administered at specific time intervals. In preferred embodiments, a first and at least one second dose of the composition of the invention are administered with a time interval of no more than 48 hours between the first and second dose. For example, the time interval between administration of a first and a second dose can be about 0.5 hour to about 48 hours; about 2 hours to about 47 hours; about 2 hours to about 46 hours; about 3 hours to about 45 hours; about 4 hours to about 44 hours; 5 hour to about 42 hours; about 6 hour to about 41 hours; about 7 hours to about 40 hours; about 8 hours to about 39 hours; about 9 hours to about 38 hours; 10 hours to about 37 hours; about 11 hours to about 36 hours; about 12 hours to about 35 hours; about 13 hours to about 34 hours; about 14 hours to about 33 hours; about 15 hours to about 32 hours; about 16 hours to about 31 hours; about 17 hours to about 30 hours; about 18 hours to about 29 hours; about 19 hours to about 28 hours; about 20 hour to about 27 hours; about 21 hour to about 26 hours; about 22 hours to about 25 hours; and about 23 hours to about 24 hours.

In further preferred embodiments, a first and a second dose of the composition of the invention are administered with a time interval of at least 21 days between the first and second dose. For example, the time interval between administration of a first and a second dose can be about 21 days; 22 days; 23 days; 24 days; 25 days; 26 days; 27 days; 28 days; 29 days; 30 days; 31 days; 32 days; 33 days; 34 days; 35 days; 36 days; 37 days; 38 days; 39 days; or 40 days and any time interval between 21 days and 40 days.

In further embodiments; multiple doses of the compositions of the invention are administered wherein a first dose is administered and at least one further dose is administered no more than 48 hours after said first dose and/or at least 21 days after said first dose.

In some embodiments, after administration of a first dose, at least one further dose is administered once month, once a week, bi-weekly, daily, or two to four times daily.

In some embodiments, a first dose is administered at the same concentration as at least one second dose. In some embodiments a first dose is administered at a different concentration from at least one second dose. In preferred embodiments, a first dose is administered at a lower concentration than at least one second dose.

Advantageously, the FA-terminated, PEG-coated AuNPs of the invention constitute minimalist nanoparticles because they combine the use of FA for targeting renal tubule cells by FA attachment to and uptake by FA receptors on the surface of renal tubule cells and treatment of kidney fibrosis by FA present intracellular in renal tubule cells. The filtration in the glomeruli of subjects suffering from kidney fibrosis of the FA-terminated PEG coated AuNPs of the invention and the selective binding and uptake of the FA-terminated PEG coated AuNPs through FA receptors highly expressed on renal tubule cells of subjects with kidney fibrosis allows a selective and highly efficient targeting of the FA-terminated PEG coated AuNPs of the invention to renal tubule cells. Further, the release of FA from the FA-terminated, PEG-coated AuNPs of the invention leads to a high intracellular FA concentration and causes an anti-fibrotic effect in the kidneys of treated subjects. Without wanting to be bound by theory, the anti-fibrotic effect of the FA-terminated PEG coated AuNPs of the invention involves a downregulation of FA receptors on renal tubule cells and a downregulation of the expression and cytosolic location of and β-catenins in renal tubule cells. Furthermore, the FA-terminated PEG coated AuNPs of the invention inhibit the expression of type I collagen and α-SMA in the kidney and inhibit kidney infiltration by T cells.

The term "treatment" or any grammatical variation thereof (e.g., treat, treating, and treatment etc.), as used herein, includes but is not limited to, ameliorating or alleviating a symptom of a disease or condition, reducing, suppressing, inhibiting, lessening, or affecting the progression, severity, and/or scope of a condition.

The term "subject," as used herein, describes an organism, including mammals such as primates, to which treatment with the compositions according to the subject invention can be provided. Mammalian species that can benefit from the disclosed methods of treatment include, but are not limited to, apes, chimpanzees, orangutans, humans, monkeys; and domesticated animals such as dogs, cats, horses, cattle, pigs, sheep, goats, chickens, mice, rats, guinea pigs, and hamsters.

The term "effective amount," as used herein, refers to an amount that is capable of treating or ameliorating a disease or condition or otherwise capable of producing an intended therapeutic effect. In an embodiment, an effective amount is an amount that is useful for treating or ameliorating kidney fibrosis. In an embodiment, an effective amount enables an inhibition or reduction of kidney fibrosis in a subject. Effective dosages and schedules for administering the therapeutic agents and compositions described herein can be determined empirically, and making such determinations is routine to one of ordinary skill in the art.

The skilled artisan will understand that the dosage of the compositions of the instant invention varies, depending upon, for example, the route of administration, the particular nanoparticle to be used in the composition, other drugs being administered, and the age, condition, gender and seriousness of the disease in the subject as described above. An effective dose of a nanoparticle composition of the invention generally ranges between about 1 µg/kg of body weight and 100 mg/kg of body weight. Examples of such dosage ranges include, but are not limited to, about 1.5 µg/kg to about 90 mg/kg; about 2 µg/kg to about 80 mg/kg; about 5 µg/kg to about 70 mg/kg; about 7.5 µg/kg to about 65 mg/kg; about 10 µg/kg to about 60 mg/kg; about 12.5 µg/kg to about 55 mg/kg; about 15 µg/kg to about 50 mg/kg; about 17.5 µg/kg to about 45 mg/kg; about 20 µg/kg to about 40 mg/kg; about 22.5 µg/kg to about 35 mg/kg; about 25 µg/kg to about 30 mg/kg; about 27.5 µg/kg to about 25 mg/kg; about 30 µg/kg to about 20 mg/kg; about 32.5 µg/kg to about 18 mg/kg; about 35 µg/kg to about 17 mg/kg; about 37.5 µg/kg to about 16 mg/kg; about 40 µg/kg to about 15 mg/kg; about 42.5 µg/kg to about 14 mg/kg; about 45 µg/kg to about 13 mg/kg; about 47.5 µg/kg to about 12 mg/kg; about 50 µg/kg to about 11 mg/kg; about 52.5 µg/kg to about 10 mg/kg; about 55 µg/kg to about 9 mg/kg; about 57.5 µg/kg to about 8 mg/kg; about 60 µg/kg to about 7 mg/kg; about 62.5 µg/kg to about 6 mg/kg; about 65 µg/kg to about 5 mg/kg; about 67.5 µg/kg to about 4 mg/kg; about 70 µg/kg to about 3 mg/kg; about 72.5 µg/kg to about 2 mg/kg; about 75 µg/kg to about 1 mg/kg; about 77.5 µg/kg to about 800 µg/kg; about 80 µg/kg to about 700 µg/kg; about 82.5 µg/kg to about 600 µg/kg; about 85 µg/kg to about 500 µg/kg; about 87.5 µg/kg to about 400 µg/kg; about 90 µg/kg to about 300 µg/kg; about 92.5 µg/kg to about 200 µg/kg; about 95 µg/kg to about 100 µg/kg.

In preferred embodiments, FA-terminated, PEG-coated AuNPs of the invention are administered at a dose of between 50 µg/kg and 200 µg/kg. In more preferred embodiments, FA-terminated, PEG-coated AuNPs of the invention are administered at a dose of between 75 µg/kg and 150 µg/kg. In most preferred embodiments, FA-terminated, PEG-coated AuNPs of the invention are administered at a dose of between 100 µg/kg and 120 µg/kg.

In some embodiments, the therapeutically effective amount of a nanoparticle composition of the invention can be administered through intravenous, oral, rectal, bronchial, nasal, topical, buccal, sub-lingual, transdermal, vaginal, intramuscular, intraperitoneal, intra-arterial, intracerebral, intraocular administration or in a form suitable for administration by inhalation or insufflation, including powders and liquid aerosol administration, or by sustained release systems such as semipermeable matrices of solid hydrophobic polymers containing the nanoparticles of the invention. Administration may be also by way of other carriers or vehicles such as patches, micelles, liposomes, vesicles, implants (e.g. microimplants), synthetic polymers, microspheres, nanoparticles, and the like.

In some embodiments, the nanoparticle compositions of the instant invention may be formulated for parenteral administration e.g., by injection, for example, bolus injection or continuous infusion. In addition, the nanoparticle compositions may be presented in unit dose form in ampoules, pre-filled syringes, and small volume infusion or in multi-dose containers with or without an added preservative. The nanoparticle compositions may be in forms of suspensions, solutions, or emulsions in oily or aqueous vehicles. The composition may further contain formulation agents such as suspending, stabilizing and/or dispersing agents. In further embodiments, the active ingredients of the compositions according to the instant invention may be in powder form, obtained by aseptic isolation of sterile solid or by lyophilization from solution for constitution with a suitable vehicle, e.g. sterile, pyrogen-free water, before use.

MATERIALS AND METHODS

Preparation of Nanoparticles (NPs)

Preparation of $Au_2$-$PEG_{200}$ NPs and $Au_2$—$PEG_{200}$-FA NPs

Polyethylene glycol (PEG)-coated AuNPs of 2 nm in core diameter were synthesized as described previously[23]. Tetrachloroauric acid ($HAuCl_4$; 0.02 mmol) and methoxy- and thiol-terminated PEG ($mPEG_{200}$-SH; 0.06 mmol, BiochemPEG) were dissolved in 7 mL of methanol/acetic acid 6:1 (v/v). Sodium borohydride (0.4 mmol, Sigma) in 2 mL of Nanopure water was added dropwise with rapid stirring. After 2 h of continuous stirring, a dark brown solution was formed, and the solvent was removed under vacuum at 40° C. by using a rotary evaporator (R215, Buchi). The residues were dissolved in 5 mL of water. Then, the mixture was transferred to a 5-8 kDa molecular weight cut off membrane and dialyzed against Nanopure water for a minimum of three times over 72 h at room temperature.

To prepare folic acid (FA)-terminated, PEG-coated AuNPs of 2 nm in core diameter ($Au_{-2}$-$PEG_{200}$-FA NPs), the same procedures as described above was followed except for substituting $mPEG_{200}$-SH with FA-$PEG_{200}$-SH (BiochemPEG). The purified NPs were not soluble in water probably because $PEG_{200}$ (MW: ~200 Da) was too short to solubilize FA (MW: 441 Da).

Figure 8A:
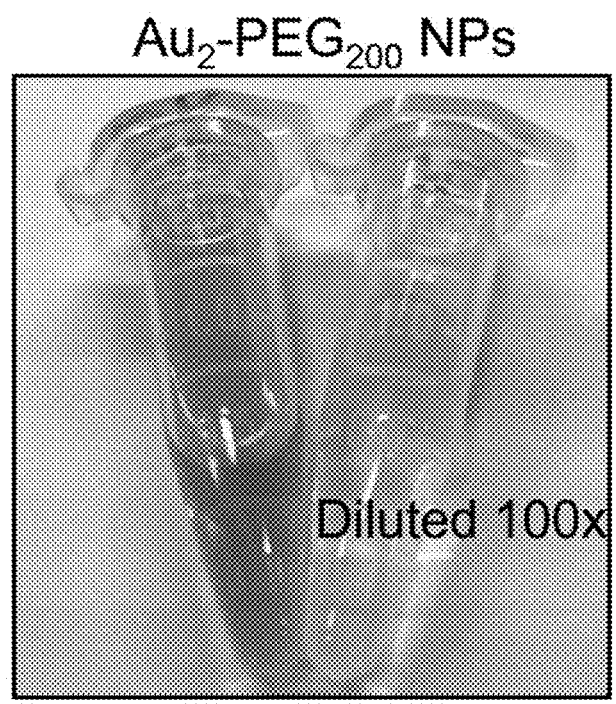
FIG. 8A shows the appearance of $Au_2$-$PEG_{200}$ NPs.
Figure 8B:
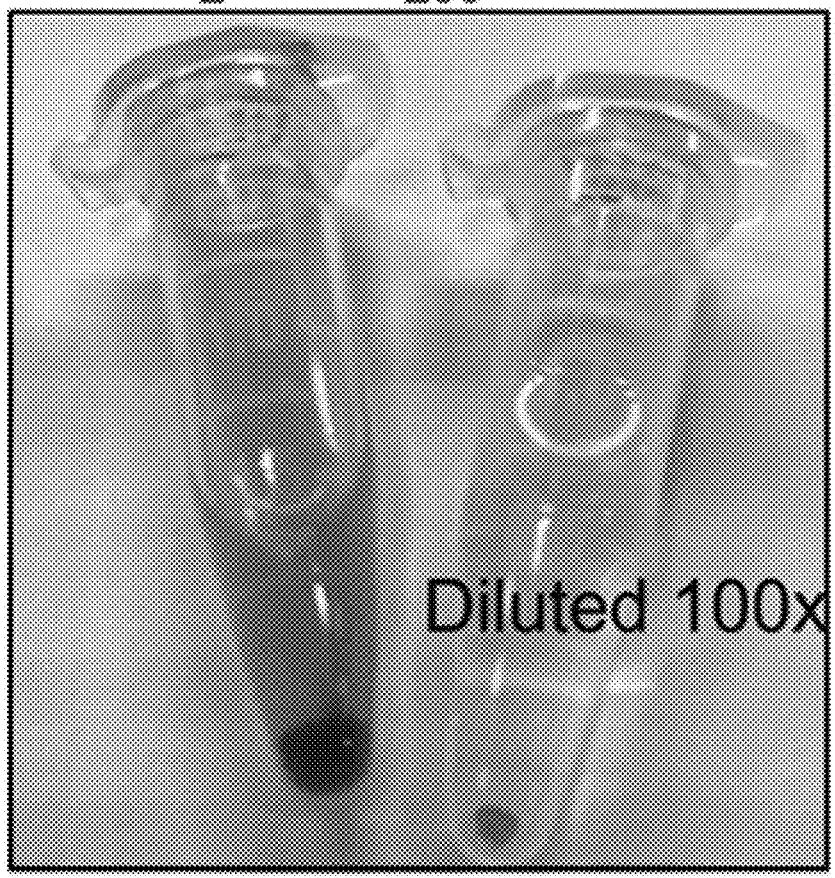
FIG. 8B shows the appearance of $Au_2$-$PEG_{200}$-FA NPs that are not soluble in water.

To prepare folic acid (FA)-terminated, PEG-coated AuNPs of 2 nm in core diameter ($Au_2$—$PEG_{200}$-FA NPs), we followed the same procedures as described for the preparation of $Au_2$-$PEG_{200}$ NPs, except for substituting $mPEG_{200}$-SH with FA-$PEG_{200}$-SH (BiochemPEG). Polyethylene glycol (PEG)-coated AuNPs of 2 nm in size were synthesized as described previously[23]. Tetrachloroauric acid (HAuCl4; 0.02 mmol) and FA-$PEG_{200}$-SH (0.06 mmol) were dissolved in 7 mL of methanol/acetic acid 6:1 (v/v). Sodium borohydride ($NaBH_4$; 0.4 mmol, Sigma) in 2 mL of Nanopure water was added dropwise with rapid stirring. After 2 h of continuous stirring, a dark brown solution was formed, and the solvent was removed under vacuum at 40° C. using a rotary evaporator (R215, Buchi). The residues were dissolved in 5 mL of water. Then, the mixture was transferred to a 5-8 kDa molecular weight cut off membrane and dialyzed against Nanopure water for a minimum of three times over 72 h at room temperature (RT). Since the purified $Au_2$-$PEG_{200}$-FA NPs were not soluble in water (FIGS. 8A-8B), further characterization of these NPs was not performed.

Preparation of $Au_3$-$PEG_{500}$NPs, $Au_5$-$PEG_{1000}$ NPs, and $Au_5$-$PEG_{5000}$ NPs The 3 nm AuNPs were synthesized as described previously[24]. 150 mL of freshly prepared sodium citrate (2.2 mM) containing 0.1 mL of tannic acid (2.5 mM, Sigma) and 1 mL of potassium carbonate ($K_2CO_3$, 150 mM) was heated in a three-necked round bottom flask under vigorous stirring. When the temperature reached 70° C., 1 mL of $HAuCl_4$ (25 mM) was injected and the reaction mixture was stirred for 5 min. The resultant 3 nm AuNPs solution was stored at 4° C.

To synthesize 5 nm AuNPs, the product solution of 3 nm AuNPs was diluted by removing 55 mL of Au seeds and adding 55 mL of sodium citrate (2.2 mM). When the temperature of the solution reached 70° C., two injections of 0.5 mL of $HAuCl_4$ (25 mM) were added at a time interval of 10 min. After 10 min, the reaction was completed, and the resultant 5 nm AuNPs solution was stored at 4° C.

Citrate-capped AuNPs were functionalized with thiolated PEG ($mPEG_{500}$-SH, BiochemPEG; $mPEG_{1000}$-SH and $mPEG_{5000}$-SH, JenKem Technology) at a concentration of 10 PEG molecules per $nm^2$ of NP surface under stirring for 2 h. Excess free PEG was removed by three rounds of centrifugation. The NPs were purified by using centrifugal filters with a membrane size cutoff of 50 kDa (Merck Millipore) and concentrated by centrifugation at 6000 rpm for 6 min.

Preparation of $Au_3$-$PEG_{500}$-FA NPs and $Au_5$—$PEG_{1000}$-FA NPs

To prepare FA-terminated, PEG-coated AuNPs of 3 nm in core diameter ($Au_3$—$PEG_{500}$-FA NPs), we followed the same procedures as described above except for substituting $mPEG_{500}$-SH with FA-$PEG_{500}$-SH (BiochemPEG). To prepare FA-terminated, PEG-coated AuNPs of 5 nm in core diameter ($Au_5$—$PEG_{1000}$-FA NPs), we followed the same procedures as described above except for substituting $mPEG_{1000}$-SH with FA-$PEG_{1000}$-SH (BiochemPEG).

Preparation of $Au_{20}$-$PEG_{5000}$NPs

The synthesis protocol follows a seed-mediated growth method as described previously[25]. For the AuNP seed, 150 mL of freshly prepared sodium citrate (2.2 mM, Alfa Aesar) was heated in a three-necked round-bottomed flask under vigorous stirring. Upon the commencement of boiling, 1 mL of $HAuCl_4$ (25 mM, Sigma) was injected, resulting in seed NPs of ~8 nm in size. Immediately afterward, the reaction was cooled until the temperature of the AuNPs solution reached 90° C. Then 1 mL of $HAuCl_4$ solution (25 mM) was injected. After 30 min, this process of cooling down and the injection of $HAuCl_4$ solution (25 mM) was repeated twice. After that, 55 mL of the mixture was removed, and the remaining mixture was diluted by adding 53 mL of Nanopure water and 2 mL of sodium citrate (60 mM). The size of the AuNPs was monitored by using UV-vis spectroscopy. The cycle of 1) dilution, 2) injection of sodium citrate, and 3) addition of three doses of $HAuCl_4$ solution was repeated until the UV-vis spectra of the resultant AuNPs exhibited localized a surface plasmon resonance (LSPR) peak at 523 nm for ~20 nm AuNPs.

Citrate-capped AuNPs were functionalized with $mPEG_{5000}$-SH at a concentration of 10 PEG molecules per $nm^2$ of NP surface under stirring for 2 h. Excess free PEG was removed by three rounds of centrifugation. $Au_{20}$-$PEG_{5000}$ NPs were centrifuged at 15,000 rpm for 30 min.

Physicochemical Characterization of NPs

The concentration of $Au_{20}$ NPs was determined by UV-vis-NIR spectrophotometry (Agilent Cary 5000) based on the Beer-Lambert's law. The molar extinction coefficient of 20 nm is $5.41 \times 10^8$ $M^{-1}cm^{-1}$[26]. The final concentration of AuNPs that were smaller than 5 nm ($Au_2$ NPs, $Au_3$ NPs, and $Au_5$ NPs) was determined by inductive coupled-plasma mass spectrometry (ICP-MS) (Agilent 7900) with reference to a standard curve of known gold concentration in parts per billion (ppb). The morphology of NPs was visualized by TEM at a voltage of 100 kV (Hitachi H7700). The average physical diameter of the NPs was measured by the ImageJ software, with at least 100 measurements taken for each type of NP. The hydrodynamic diameters and zeta potential of NPs were measured by the DelsaMax PRO dynamic light scattering (DLS) analyzer (Beckman Coulter). Reported DLS data represent the values from three independent measurements. To test for colloidal stability, the NP solutions were mixed with equal volumes of 1) PBS (0.01M), 2) 10% fetal bovine serum (FBS) in PBS, 3) 50% FBS in PBS, and incubated at 37° C. After 24 h of incubation, the AuNPs solutions were analyzed using UV-vis spectrometry and DLS. Reported DLS values represent mean±SD from three independent measurements.

Preparation of FAM-PEG-SH

Two molar excess of FAM-NHS ester (18.94 mg, Lumiprobe) was dissolved in 100 μL of DMSO (J&K Scientific). Ten mg of $NH_2$—$PEG_{500}$-SH (BiochemPEG) was dissolved 900 μL of conjugation buffer (0.1M sodium bicarbonate solution, pH 8.3-8.5). Then the NHS ester solution was added to the solution of $NH_2$—$PEG_{500}$-SH, and vortexed at RT for 4 h. The FAM-PEG-SH conjugate was purified using dialysis against Nanopure water in a 1000 Da dialysis bag (Spectrum laboratories Inc.) for 3 d. Then the FAM-PEG-SH solution was freeze dried and stored at −20° C. for storage.

10 mg of $H_2N$-$PEG_y$-SH (y=200, 500, 1000, or 5000 Da; Biochempeg) was dissolved in 900 μL of conjugation buffer (0.1 M sodium bicarbonate solution, pH 8.3-8.5). Then, two molar excess of N-hydroxysuccinimide ester of fluorescein (FAM-NHS; Lumiprobe) was dissolved in 100 μL of DMSO (J&K Scientific). The two solutions were combined, and the resulting 1 mL of reaction mixture was vortexed at RT for 4 h. The FAM-$PEG_y$-SH conjugate was purified using dialysis against Nanopure water in a 1000 Da dialysis bag (Spectrum Laboratories) for 3 d. Finally, the FAM-$PEG_y$-SH solution was freeze dried and stored at −20° C.

Preparation of FAM-Conjugated $Au_2$-$PEG_{200}$NPs

A mixture of FAM-$PEG_{200}$-SH and unlabeled mPEG200-SH (Biochempeg) at a mole ratio of 1:49 was used for the synthesis of FAM-conjugated $Au_2$-$PEG_{200}$ NPs. $HAuCl_4$ (0.02 mmol), $mPEG_{200}$-SH (0.0588 mmol), and FAM-$PEG_{200}$-SH (0.0012 mmol) were dissolved in 7 mL of a 6:1 mixture of methanol/acetic acid (v/v). Next, 2 mL of 0.2 M $NaBH_4$ (0.4 mmol in Nanopure water) was added dropwise to the reaction mixture with rapid stirring. After 2 h, a dark brown solution was formed, and the solvent was removed under vacuum at 40° C. using a rotary evaporator (R215, Buchi). After dissolving the residues in 5 mL of Nanpoure water, the mixture was transferred to a 5-8 kDa molecular weight cut off membrane and dialyzed against Nanopure water for a minimum of three times over 72 h at RT. The concentration of NPs was then determined by ICP-MS.

Preparation of FAM-Conjugated $Au_3$-$PEG_{500}$, $Au_5$—$PEG_{1000}$, $Au_5$—$PEG_{5000}$, and $Au_{20}$—$PEG_{5000}$ NPs A mixture of FAM-$PEG_y$-SH and unlabeled $mPEG_y$-SH at a mole ratio of 0.2:9.8 was reacted with citrate-capped $Au_x$ NPs (x=3, 5, and 20 nm) at a total concentration of 10 PEG molecules per nm² of NP surface under stirring for 2 h. The resultant NPs were washed by centrifugation for five times to ensure complete removal of the unconjugated PEG strands. The concentration of NPs was then determined by ICP-MS.

Displacement of PEG Strands from the AuNP Surface 0.1 mL of dithiothreitol (DTT; Sigma) solution (1.0 M in 0.18 M phosphate buffer, pH=8) was added to 0.1 mL of FAM-conjugated $Au_x$-$PEG_y$ NPs (~5 µg of Au for $Au_{20}$ NPs and ~40 µg of Au for $Au_2$, $Au_3$, and $Au_5$ NPs) to displace the conjugated PEG strands from the AuNP surface. The mixture was swirled overnight to allow for complete displacement of the PEG strands and aggregation of the AuNPs. After centrifugation at 15,000 rpm for 30 min, 150 µL of the supernatant solution was pipetted into a 96-well microplate to measure the FAM fluorescence signals in a Multiskan GO UV-absorbance microplate reader (Thermo Fisher Scientific). The excitation wavelength and emission wavelength of FAM was 495 nm and 520 nm, respectively. The concentration of FAM-PEG-SH strands was calculated with reference to a standard curve and multiplied by 50 to account for the FAM-$PEG_y$-SH to m$PEG_y$-SH loading ratio (0.2:9.8).

Quantification of FA Loading for $Au_3$-$PEG_{500}$-$FA_z$ NPs

Preparation of FAM-Conjugated $Au_3$-$PEG_{500}$-$FA_z$ NPs

To prepare FAM-conjugated $Au_3$-$PEG_{500}$-$FA_{32}$ NPs, we followed the same synthesis procedures as described for preparing $Au_3$-$PEG_{500}$ NPs above, except for substituting m$PEG_{500}$-SH with FA-PEG500-SH (BiochemPEG). That is, a mixture of FAM-$PEG_{500}$-SH and unlabeled FA-$PEG_{500}$-SH at a mole ratio of 0.2:9.8 was reacted with citrate-capped $Au_3$ NPs, keeping a total concentration of 10 PEG molecules per nm² of NP surface.

To prepare FAM-conjugated $Au_3$-$PEG_{500}$-$FA_{16}$ NPs, a mixture of FAM-$PEG_{500}$-SH, unlabeled FA-$PEG_{500}$-SH, and unlabeled m$PEG_{500}$-SH at a mole ratio of 0.1:4.9:5 was reacted with citrate-capped $Au_3$ NPs, keeping a total concentration of 10 PEG molecules per nm² of NP surface.

To prepare FAM-conjugated $Au_3$-$PEG_{500}$-$FA_8$ NPs, a mixture of FAM-$PEG_{500}$-SH, unlabeled FA-$PEG_{500}$-SH, and unlabeled m$PEG_{500}$-SH at a mole ratio of 0.25:2.25:7.5 was reacted with citrate-capped $Au_3$ NPs, keeping a total concentration of 10 PEG molecules per nm² of NP surface.

For FAM-conjugated $Au_3$-$PEG_{500}$-$FA_z$ NPs of all FA loadings, the resultant NPs were washed by centrifugation for five times to ensure complete removal of the unconjugated PEG strands. The concentration of NPs was then determined by ICP-MS.

Displacement of PEG Strands from the AuNP Surface

We followed the same procedures as described for displacing the PEG strands from $Au_3$-$PEG_{500}$ NPs above. That is, 0.1 mL of dithiothreitol (DTT; Sigma) solution (1.0 M in 0.18 M phosphate buffer, pH=8) was added to 0.1 mL of FAM-conjugated $Au_3$-$PEG_{500}$-$FA_z$ NPs (~40 µg of Au) to displace the conjugated PEG strands from the AuNP surface. The number of FA-$PEG_{500}$-SH on each AuNP was calculated by multiplying by the FAM-$PEG_{500}$-SH: $PEG_{500}$-SH ratio loaded to each AuNP.

Quantification of the Loading of PEG Strands

Quantification of Loading of PEG Strands on $Au_3$-$PEG_{500}$ NPs, $Au_5$—$PEG_{1000}$ NPs, and $Au_5$-$PEG_{5000}$ NPs The loading of PEG strands on the AuNPs was quantified using a fluorophore-based method[27]. In brief, a mixture of FAM-PEG-SH and unlabeled mPEG-SH (with a mole ratio of 1:49) was reacted with citrate-capped AuNPs at a total concentration of 10 PEG molecules per nm² of NP surface under stirring for 2 h. The resultant NPs were washed by centrifugation for 5 times to ensure complete removal of the unconjugated PEG strands. The concentration of NPs was then determined by ICP-MS. Then, 0.1 mL of dithiothreitol (DTT; Sigma) solution (1.0 M in 0.18 M phosphate buffer, pH=8) was added to 0.1 mL of Au-PEG NPs (2.5 µM) to displace the conjugated PEG strands from the AuNP surface. The mixture was swirled overnight to allow for complete displacement of the PEG strands and aggregation of the AuNPs. After centrifugation at 15,000 rpm for 30 min, the supernatant solution (150 µL) was pipetted into a 96-well microplate reader to measure the FAM fluorescence signals (excitation wavelength=495 nm, emission wavelength=520 nm). The concentration of FAM-PEG-SH strands was calculated with reference to a standard curve. The FA-PEG-SH loading per AuNP was calculated by dividing the concentration of FAM-PEG-SH by the concentration of AuNPs. The total PEG loading per NP was calculated by multiplying the loading of FAM-PEG-SH by 50. Reported data represent mean±SD from four independent experiments.

Quantification of Loading of PEG Strands on $Au_{20}$-$PEG_{5000}$NPs

The procedures were based our previously published report[28]. The density of PEG strands on the surface of AuNPs was determined by thiol depletion via the Ellman's assay. One mL of 2 nM cit-AuNPs was mixed with m$PEG_{5000}$-SH at a concentration of 10 PEG molecules per nm² of NP surface for 1 h under stirring. After centrifuging the NP solution at 12000×g for 15 min, the supernatant was lyophilized and resuspended in 60 µL of Nanopure water. Twenty µL of the concentrated PEG sample were mixed with 100 µL of Ellman's assay buffer [1 mM EDTA (Sigma) in 0.1 mM $Na_2HPO_4$ (Sigma); pH=8]. The resultant PEG sample was mixed with 50 µL of Ellman's detection buffer [0.5 mg/mL of Ellman's reagent (5,5-dithio-bis(2-nitrobenzoic acid)) (JenKem Technology) in the assay buffer]. Citrate-capped Au NPS (Cit-AuNPs) not functionalized with PEG strands were included as negative control. After 10 min of reaction, the absorbance of the reaction mixture was read at 412 nm by a Multiskan GO UV-absorbance microplate reader (Thermo Fisher Scientific). The concentration of PEG was calculated with reference to a standard calibration curve after subtracting the background absorbance of the sample derived from that of the negative control. Reported data represent mean±SD from four independent experiments.

Preparation of Au-PEG-FA NPs with Different FA Loadings

Citrate-capped AuNPs of 3 nm in diameter with different mixing ratios of FA-$PEG_{500}$-SH to m$PEG_{500}$-SH were used keeping the total PEG loading constant at a concentration of 10 PEG molecules per nm² of NP surface. The mixing ratios of m$PEG_{500}$-SH and FA-$PEG_{500}$-SH were 1:0 for Au-PEG NP, 3:1 for Au-PEG-FA¼ NPs (25% of the maximal amount of FA on the NP), 1:1 for Au-PEG-FA½ NPs (50% of the maximal amount of FA on the NP), and 0:1 for Au-PEG-FA NPs (100% of the maximal amount of FA on the NP). The exact loading of the three types of FA-PEG AuNPs was verified by using the fluorophore-based method as mentioned above.

Physicochemical Characterization of NPs

The concentration of $Au_{20}$ NPs was determined by UV-vis-NIR spectrophotometry (Agilent Cary 5000) based on the Beer-Lambert's law. The molar extinction coefficient of 20 nm is $5.41 \times 10^8$ $M^{-1}cm^{-1}$[26]. The final concentration of AuNPs that are smaller than 5 nm ($Au_2$ NPs, $Au_3$ NPs, and $Au_5$ NPs) was determined by inductive coupled-plasma mass spectrometry (ICP-MS) (Agilent 7900) with reference to a standard curve of known gold concentration in parts per billion (ppb). The morphology of NPs was visualized by TEM at a voltage of 100 kV (Hitachi H7700). The average physical diameter of the NPs was measured by the ImageJ software, with at least 100 measurements taken for each type of NP. The hydrodynamic diameters and zeta potential of NPs were measured by the DelsaMax PRO dynamic light scattering (DLS) analyzer (Beckman Coulter). Reported DLS data represent the values from three independent measurements. To test for colloidal stability, the NP solutions were mixed with equal volumes of 1) PBS (0.01M), 2) 10% fetal bovine serum (FBS) in PBS, 3) 50% FBS in PBS, and incubated at 37° C. After 24 h of incubation, the AuNPs solutions were analyzed using UV-vis spectrometry and DLS. Reported DLS values represent mean±SD from three independent measurements.

Animals

All procedures followed the guidelines stipulated by the Animal Experimentation Ethics Committee (AEEC) at The Chinese University of Hong Kong (CUHK). For all animal experiments, male Balb/c mice between 8 and 12 wk of age were used and randomly divided into various treatment groups. All mice were housed in a temperature- and humidity-controlled environment with a 12-h light/dark cycle. For all distribution and efficacy studies, NPs or free FA molecules were formulated in 100 µL of 5% dextrose (D5W; Sigma) for a single intravenous (i.v.) injection using a 29-gauge insulin syringe (Terumo). For all biodistribution and efficacy studies, the sample size (n) indicates biological replicates.

Unilateral Ureteral Obstruction (UUO)

Mouse model of renal fibrosis was induced by the UUO surgery as previously described[12,29]. Mice were anesthetized by an intraperitoneal injection of ketamine (100 mg/kg; Alfasan International B.V.) and xylazine (10 mg/kg; Alfasan International B.V.). The peritoneum was cut along the midline, and the left ureter was isolated and ligated twice by using a 5-0 suture (NingBo Cheng-He Microsurgical Instruments). The bowel was laid back and the peritoneum was closed with suture. The mice were placed under a heating lamp to maintain body temperature until they recovered from anesthesia. For analgesia, three injections of buprenorphine (Temgesic, 0.05 mg/kg) were given to the mice subcutaneously every 12 h after the surgery. To verify the development of fibrosis, the mice were sacrificed by cervical dislocation with anesthesia, and their kidneys were weighted (see FIG. 4) and processed for histological analysis (see FIGS. 5A-5C).

Organ-Level Distribution of NPs

For all types of $Au_x$-$PEG_y$ NPs and $Au_3$—$PEG_{500}$-$FA_{32}$ NPs, equal amounts of Au (100 µg) were injected into each animal. The NP solutions were injected into UUO mice 7 d after UUO surgery and the animal sacrificed for organ collection 24 h post injection (or 8 d after UUO surgery). Tissues were generally weighed and digested with 0.5 mL of aqua regia (3:1 v/v ratio of 38% HCl and 68% $HNO_3$) for 4 d at RT, unless otherwise stated. Whole livers were digested with 4 mL of aqua regia, but 0.3 mL of blood was digested with 1.2 mL of aqua regia for 4 d at RT. The digested samples were diluted to a 2% HCl, 2% $HNO_3$ solution with Nanopure water and then filtered with 0.1 µm acid resistant (cellulose nitrate and cellulose acetate) filter (HINOE) using a 10 mL syringe. Calibration standards of known gold concentration were prepared to convert counts of gold ion to known concentration. ICP-MS was used to measure the gold content in the sample.

Intrarenal Tissue-Level Distribution of NPs

For all types of $Au_x$-$PEG_y$ NPs and $Au_3$—$PEG_{500}$-$FA_{32}$ NPs, equal amounts of Au (100 µg) were injected into each animal. The NP solutions were injected into UUO mice 7 d after UUO surgery and the animal sacrificed for organ collection 24 h post injection (or 8 d after UUO surgery). Glomeruli isolation was performed as described previously with a slight modification.[30] In brief, anesthetized mice were perfused with $8 \times 10^7$ Dynabeads (Thermo Fisher Scientific) diluted in 40 mL of PBS through the heart. Then, the kidneys were removed, minced, and digested in a digestion solution [1 mg/mL collagenase A (Roche), 100 U/mL deoxyribonuclease I (Roche) in Hanks' balanced salt solution (HBSS) (Thermo Fisher Scientific)] at 37° C. for 40 min with gentle agitation. The digested tissue was pressed through a 100 µm cell strainer (BD Falcon) using a flattened pestle, and the cell strainer was then thoroughly washed with 5 mL of ice-cold HBSS. The cell suspension was centrifuged at 200×g for 5 min at 4° C. The first supernatant was transferred to a new tube (labelled "supernatant"), and the cell pellet was resuspended in 2 mL of HBSS. The Dynabeads-containing glomeruli were gathered by a magnetic particle concentrator (Dynal). The second supernatant (including the cells not attracted to the magnet) was carefully pipetted into a separate tube and stored on ice (labelled "tubules+tubulointerstitial cells"). All samples were freeze-dried and digested with aqua regia for ICP-MS measurements, as described in the previous section.

Hepatobiliary Clearance or Renal Clearance of NPs

Mice were injected i.v. with $Au_x$-$PEG_y$ NPs or $Au_x$—$PEG_y$-FA NPs of various NP core sizes and PEG molecular weights (with or without FA) at a constant gold mass of 100 µg. Then, the mice were housed in metabolic cages (Lab products Inc) for the collection of their feces and urine at various time points post-injection. Urine and feces samples were digested with 1.2 mL and 2 mL of aqua regia respectively, for 4 d at RT for ICP-MS measurements.

Alternatively, mice were injected i.v. with $Au_x$-PEGy NPs of various NP core sizes (x in nm) and PEG molecular weights (y in Da) or $Au_3$—$PEG_{500}$-$FA_{32}$ NPs at a constant gold (Au) mass of 100 µg per 100 µL of injection. Then, the mice were housed in metabolic cages (Lab products Inc) for the collection of their feces and urine at various time points post-injection. Urine and feces samples were digested with 1.2 mL and 2 mL of aqua regia respectively, for 4 d at RT for ICP-MS measurements.

Tissues and Paraffin Blocks

Tissues were fixed in 10% buffered formalin (3.7% w/v) for 48 h, then stored in PBS (0.1M, pH 7.5) at 4° C. until tissue dehydration. Fixed tissues were dehydrated in ethanol, cleared in xylene, and embedded in paraffin blocks. Paraffin-embedded tissue sections (4 µm) were cut and mounted on Superfrost Plus™ Adhesion microscope slides (Thermo Scientific).

Silver Enhancement Staining

Paraffin-embedded tissue sections of 4 µm thick were deparaffinized in xylene (5 min×3 times) and rehydrated through a series of ethanol (100%, 90%, 70%; 3 min×2 times at each ethanol concentration), and deionized water (Milli Q) (5 min×5 times). The rehydrated tissue sections were stained by the Silver Enhancement Kit for Light and Electron Microscopy (Ted Pella). The silver enhancement solutions, Solution A (silver salt) and Solution B (initiator), were mixed at a 1:1 ratio immediately before use. A drop of the mixture (~50 µL) was applied to the tissue section for 20 min under normal laboratory lighting. Next, the tissue sections were rinsed with Milli Q water (3 min×3 times), followed by counterstaining with Mayer's Hematoxylin (blue-purple nuclear stain) or methyl green (blue-green nuclear stain) for 10 min (Vector Laboratories). Bright-field images were acquired using the Nikon Eclipse Ni (DS-Ri2) microscope.

Confocal Reflectance Microscopy

Confocal reflectance images of tissue sections overlaid with true color images were obtained by using a Leica SP8 confocal microscope. Reflected light confocal images were produced in the reflectance mode with 20× objectives under 488 nm excitation[31]. True color images were produced by overlaying the red, green, and blue (RGB) channels in the transmitted light imaging mode.

Immunohistochemistry

Mouse kidney tissue—Two slides from each kidney were selected for each set of stains such that two section-containing slides were at least 200 μm away from each other. IHC staining was performed on paraffin sections using the microwave-based antigen retrieval technique[32]. Tissue sections were deparaffinized and rehydrated to water. After placing the slides in citrate buffer (10 mM citric acid, pH 6.0), the slides were heated in the microwave oven for 3 min under high power (~95-100° C.) and for 20 more min under low power. After cooling the slides in the heated solution for 30 min, they were rinsed in distilled water twice and in PBS for 5 min. Next, the slides were blocked with 2.5% normal horse serum (Vector Laboratories) for 2 h and incubated with 60 μL of primary antibodies [1 μg/mL for type I collagen (1310-01; Southern BioTech), 0.048 μg/mL for α-SMA (ab150301; Abcam)) 0.625 μg/mL for folate receptor (ab67422; Abcam), 1.25 μg/mL for CD3 (ab16669; Abcam), 1.25 μg/mL for Wnt5b (ab93134; Abcam), and pre-diluted β-catenin (ab15180; Abcam)] at 4° C. overnight. Slides were then washed in PBS and treated with 3% $H_2O_2$ (Merck Millipore) for 30 min, rinsed again, and incubated with ~50 μL of secondary antibodies (ImmPRESS HRP Polymer detection Kit, Vector Laboratories) for 30 min. The sections were developed sequentially by using 3,3'-diaminobenzidine (DAB) enzyme substrate (ImmPACT™ DAB, Vector Laboratories) for 2 min. All slides were counter-stained with Mayer's hematoxylin for 3 min, washed in distilled water, dried in 90% ethanol, and mounted by using xylene-based mounting medium. Bright-field images were acquired using the Nikon Eclipse Ni (DS-Ri2) microscope.

Human kidney tissue—Paraffin sections of human kidney biopsy specimens with a diagnosis of hypertensive nephrosclerosis were used. These specimens were delinked from their clinical data and identifier. IHC analysis of the expression of human folate receptor largely followed the procedures for analyzing the expression of mouse folate receptor, except for using 0.313 μg/mL of primary antibody for folate receptor (ab67422; Abcam).

Cellular-Level Distribution of NPs: TEM

Tissue blocks (~1 mm$^3$) were fixed with glutaraldehyde (2.5% in 0.1 M phosphate buffer, pH=7.4) at room temperature for 2 h, and at 4° C. for overnight. Then tissue blocks were washed stained with osmium tetroxide (1%) at 4° C. for 2 h. The tissue blocks were gradually dehydrated with increasing ethanol gradients and propylene oxide. The tissue blocks were embedded in Epon 812 resins (Electron Microscopy Sciences) and polymerized at 55° C. for 48 h. Ultrathin sections of around 70 nm thick were deposited on 200-mesh copper grids (EMS) and stained with 4% (w/v) uranyl acetate (EMS) in 50% methanol/water) and Reynolds lead citrate (Sigma) for visualization under TEM at 100 kV (Hitachi H7700).

Sample Size Calculation

For efficacy studies, we used Dunnett's test to deduce the required size of each treatment group (N)[49]. Dunnett's test is a multiple comparison procedure that compares the efficacy of each treatment group with the same control group. Here, we tested "H0: All treatment groups are equivalent to the control group" against "H1: There exists one group that is superior to the control group". We compared the treatment groups and the control group in a way that (i) the chance of committing type 1 error is <5% and that (ii) our comparison is of power 80%. Dunnett's formalism states that $p=\sqrt{N}\delta/\sigma$, where p is the correlation coefficient that depends on N. As our studies entail 4 different treatment groups and a control group (i.e., saline), p is 4.46[49]. If the superior treatment group gives an outcome (δ) of 1.5 standard deviation (σ) better than the control group, the required N is $(4.46/1.5)^2=8.84\approx9$.

Efficacy Study

A single dose of $Au_3$-$PEG_{500}$ NPs, $Au_3$—$PEG_{500}$-FA NPs, free FA (formulated in 0.1 mL of D5W), or saline was injected into UUO mice with established renal fibrosis (7 d after UUO surgery) via the tail vein. FA was dissolved in sterile BioPerformance Certified DMSO (Sigma) and formulated in D5W prior to injection. The final concentration of DMSO was less than 1%. $Au_3$-$PEG_{500}$-FA NPs formulated in D5W was injected i.v. at a dose of 0.12 mg-FA/kg-mouse (or equivalently 2.5 mg-Au/kg-mouse). $Au_3$—$PEG_{500}$ NPs were injected i.v. as a vehicle only control at a dosage of 2.5 mg-Au/kg-mouse. Saline was injected i.v. as a negative control. Captopril (TCI), an ACE inhibitor, was injected intraperitoneally (i.p) at a dose of 5 mg/kg daily beginning on Day 7 after UUO surgery for 7 days[46]. Mice in all groups were sacrificed on Day 14 after UUO surgery (7 days post injection), with n=9 per group.

Treated mice were anesthetized and sacrificed by cervical dislocation 7 d post-injection. For blood collection, mice were anesthetized, and blood was collected into EDTA tubes (Becton Dickinson) via cardiac puncture. The kidneys were dissected, and the ureters were removed before weighing. The remaining kidney tissues were fixed in 10% buffered formalin for histology analysis.

Measurement of Anti-Fibrosis Efficacy

On Day 14 post-UUO surgery, mice were euthanized to harvest the UUO kidney for evaluation of kidney morphology and for quantification of the expression levels of collagen I, α-SMA, and CD3-positive cells in tissue sections as revealed by IHC staining. The major measurable outcome was the expression level of collagen I, as quantified by the percentage area of IHC staining in the kidney sections. Images were taken at the cortex area of the kidney. The percentage area of IHC staining was quantified using at least 8 images from each tissue sections, and the averaged values were displayed using stacked bar chart with scatter plot points. Then serial sections from the same kidney were stained with H&E for the analysis of tissue morphology by light microscopy.

Data Processing and Analysis

Comparison of equivalence between multiple treatment groups and the untreated control group was computed by the Dunnett's test and one-way analysis of variance (ANOVA) using the SPSS software. All results in this work are biological replicates (unless specified). For One-Way ANOVA, Tukey's post hoc test (with 95% confidence level) was used for multiple comparisons when the result was significant (p<0.05). Normality of sampling distribution of means was validated by Kolmogorov-Smirnov test. There are no outliers outside 3 standard deviations. Homogeneity of variance was validated by Levene's test.

Toxicity Test

Liver, heart, and spleen samples were fixed in 10% buffered formalin for 48 h and then stored in PBS at 4° C. Paraffin-embedded tissue sections of 4 μm thick were stained with hematoxylin and eosin for the tissue morphology by light microscopy. Blood, collected via an intracardiac puncture, was stored in a plain tube for biochemistry tests and in EDTA-coated tubes (Becton Dickinson) for hematology analysis. The blood samples were kept on ice and later sent to PathLab (Hong Kong) for analysis on the same day.

Endotoxin Level

The procedures were based on our previously published report[50]. The endotoxin level of NPs was measured by the Pierce LAL Chromogenic Endotoxin Quantification Kit (Thermo Fisher Scientific) per the manufacturer's instructions. 50 μL of each standard or supernatant of NPs were transferred to a 96-well plate that was prewarmed to 37° C. 50 μL of the LAL reagent was added to each well, and the plate was incubated at 37° C. for 10 min. 100 μL of chromogenic substrate solution (prewarmed to 37° C.) was added to each well, and the plate was incubated at 37° C. for 6 more minutes. 100 μL of 25% acetic acid was added to each well. Absorbance at 405 nm was measured by a Multiskan GO UV-absorbance microplate reader (Thermo Fisher Scientific). Endotoxin levels were calculated based on a calibrated standard curve.

Transcriptomic Analysis

UUO mice were i.v. injected with $Au_3$-$PEG_{500}$-FA NPs (i.e., 50 mg-Au/kg-mouse) or free (i.e., 0.12 mg-FA/kg-mouse) on Day 7 after UUO surgery, at the same dosage used for the efficacy studies. An untreated group of UUO mice was also included as control. On Day 9 after UUO surgery (i.e., 48 h post-injection), the mice were sacrificed and the UUO kidneys were harvested. After cutting the UUO kidneys in half using a scalpel, one set of the halved kidneys was fixed in buffered formalin while the other set was snap frozen in liquid nitrogen and stored at −80° C. The formalin-fixed samples were dehydrated as mentioned above and embedded in paraffin blocks to generate tissue sections for validating the RNA-seq data. The frozen samples were sent to Beijing Genomics Institute (BGI) for RNA extraction, RNA library construction, and bioinformatic analysis. A total of 9 samples were sequenced using the BGISEQ platform, with ~4.57 Gb generated per sample. The average mapping ratio with reference genome is 94.33%. Differential expressed genes (DEGs) detection, gene ontology analysis of DEG, and other analysis based on gene expression were performed by BGI. Further analysis of the DEGs was performed by filtering the list of DEGs with a FPKM threshold of 2 for at least 6 out of the 9 UUO samples tested. GO terms, and DEGs with corrected p values (Q values) of 0.05 or less were considered significantly enriched.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1—Description of the Unilateral Urethral Obstruction (UUO) Model and Disease Stages In the UUO model, the left ureter in Balb/c mice was permanently obstructed by ligation with a suture (FIGS. 1A, 1B, and 1C). This resulted in dilatation of the ureter together with reduced renal blood flow and glomerular filtration, and the establishment of renal fibrosis by Day 7 post-surgery[1]. FIG. 2 shows the gross anatomy of the contralateral (CL) kidney and the UUO kidney. The ureter of the UUO kidney was dilated due to the accumulation of urine. The UUO kidney looked paler than the CL kidney, possibly because the UUO kidney may have received less blood flow than the CL kidney.

IHC images revealed a stronger expression of α-SMA and type I collagen in the UUO kidneys when compared with the CL kidney (FIG. 3). The tubulointerstitium was outlined by the positive staining patterns of α-SMA in the UUO kidney, and smooth muscle cells lining the blood vessel walls (arrows) can also be detected in the CL kidney. The prominent expression of α-SMA+ cells and type I collagen in the UUO kidney indicates the presence of renal fibrosis.

Figure 4:
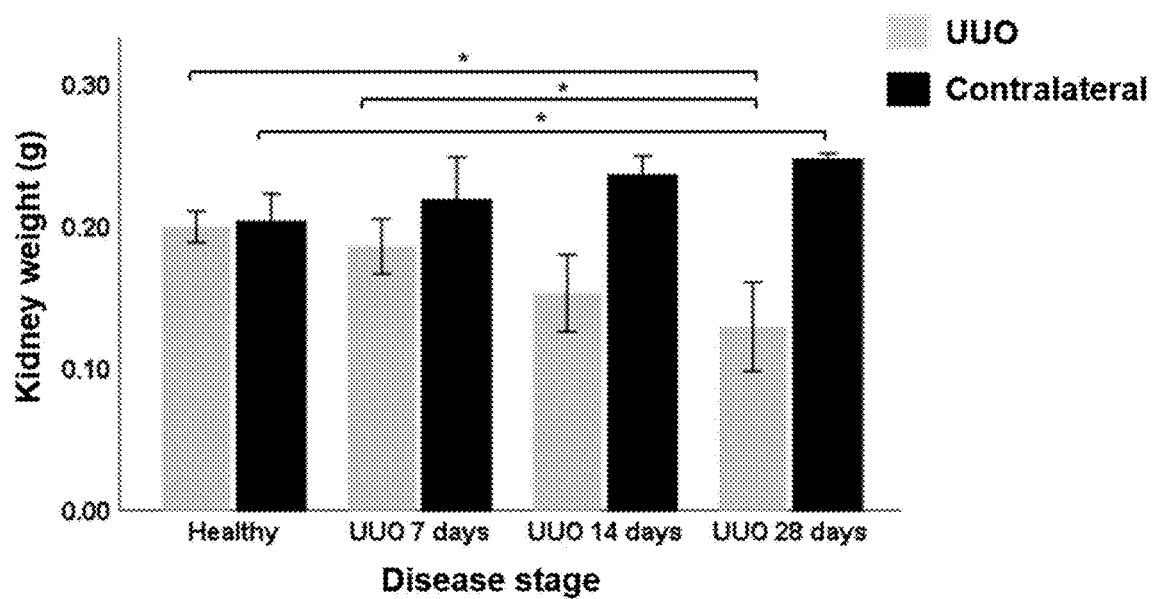
FIG. 4 shows the kidney weight (g) normalized to body weight of each mouse at sacrifice, and the resulting ratio was multiplied by 25 to adjust all weights to a relative one for a 25-gram mouse. (*) denotes $p \leq 0.05$. Error bar denotes ±1 standard deviation, with n=4.
Figure 5A:
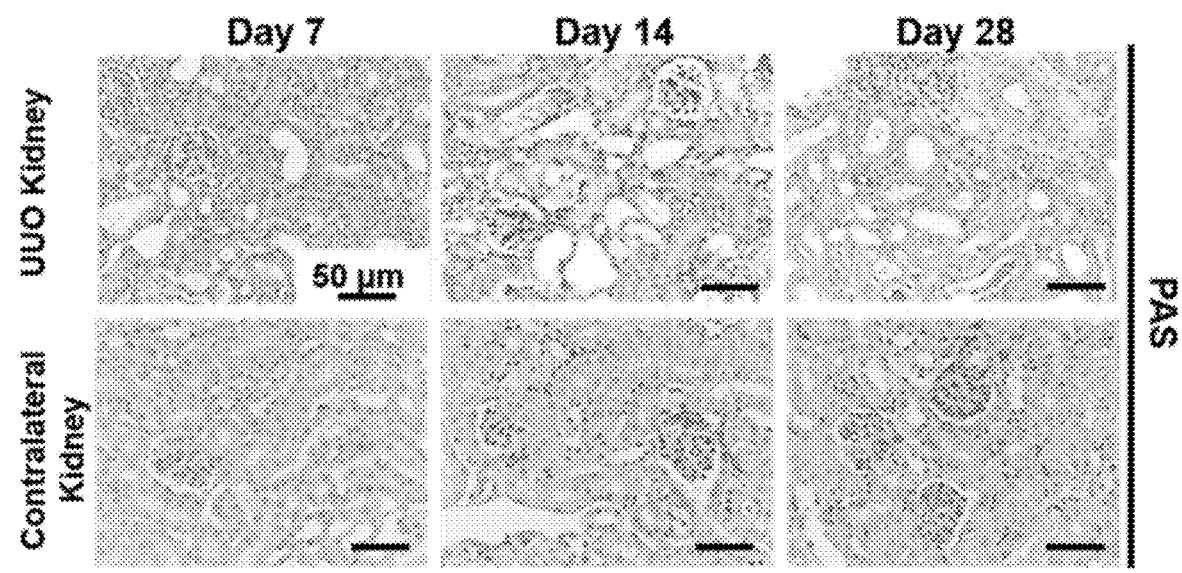
FIG. 5A shows PAS staining of UUO kidneys and contralateral kidneys at days 7, 14, and 28 post UUO surgery.
Figure 5B:
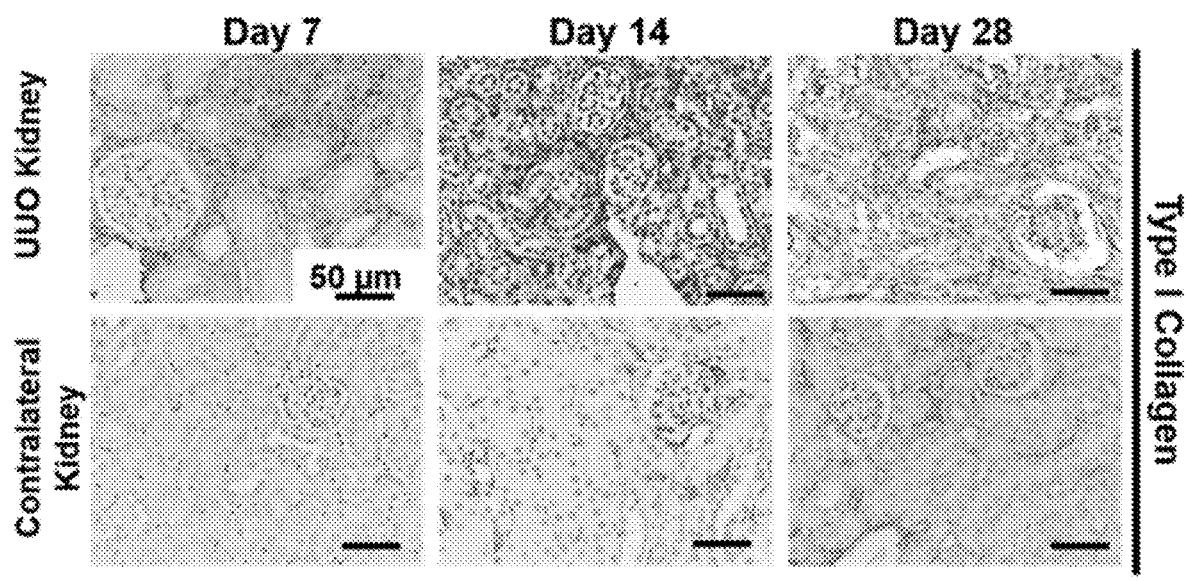
FIG. 5B shows Type I collagen staining of UUO kidneys and contralateral kidneys at days 7, 14, and 28 post UUO surgery.
Figure 5C:
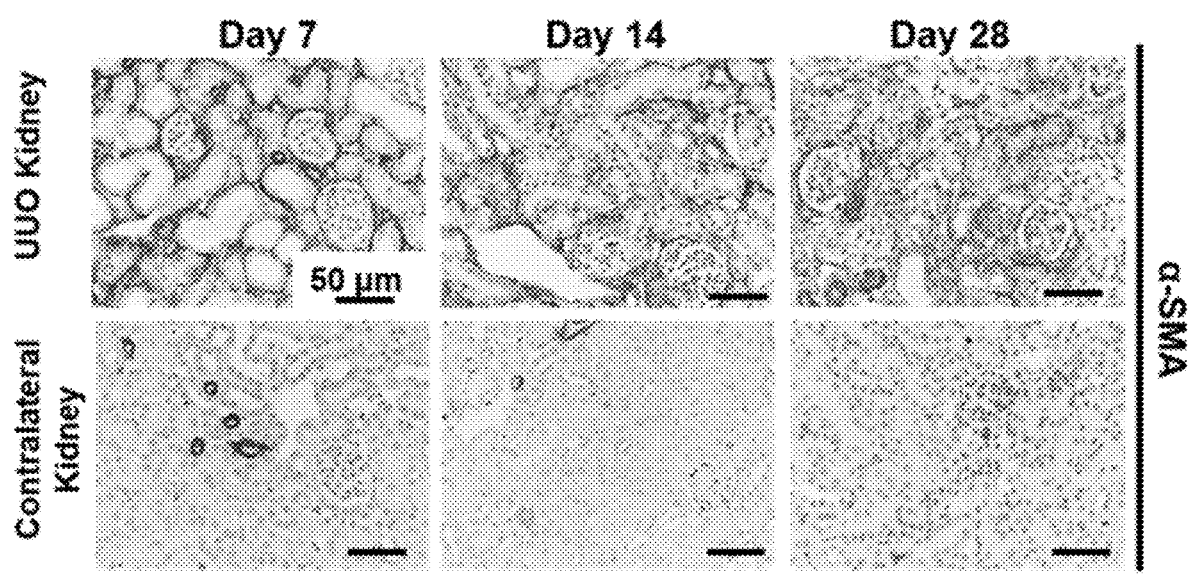
FIG. 5C shows α-SMA staining of UUO kidneys and contralateral kidneys at days 7, 14, and 28 post UUO surgery.
Figure 6A:
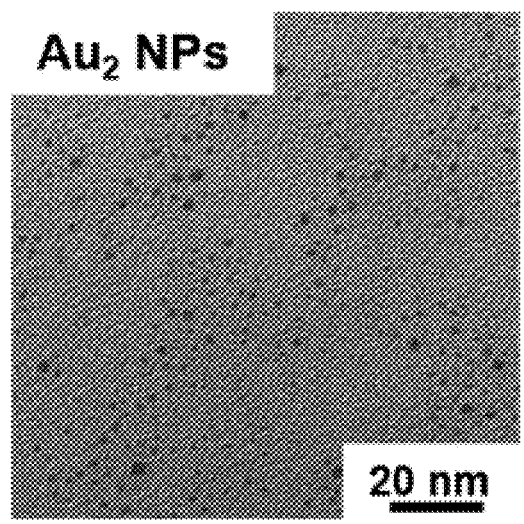
FIG. 6A shows TEM images of AuNPs with a diameter of ~2 nm as synthesized with SH-$PEG_{0.2k}$.
Figure 6B:
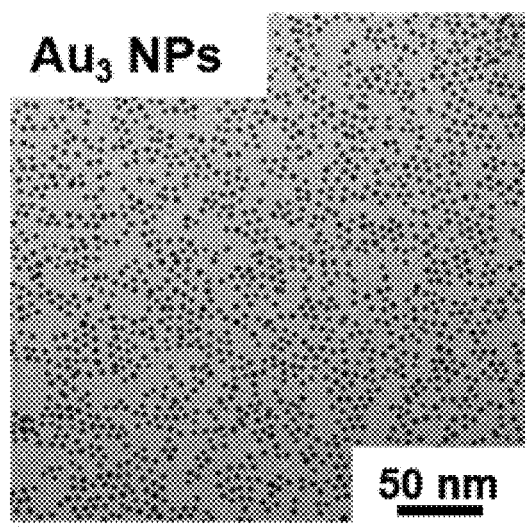
FIG. 6B shows TEM images of AuNPs with a diameter of ~3 nm as-synthesized via reduction of $HAuCl_4$ by sodium citrate and tannic acid.
Figure 6C:
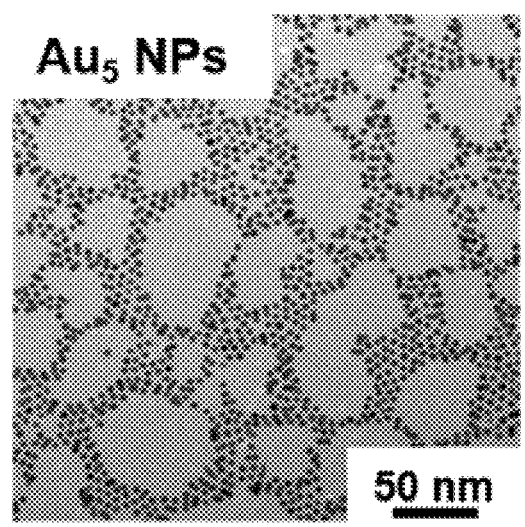
FIG. 6C shows TEM images of AuNPs with a diameter of ~5 nm as synthesized via reduction of $HAuCl_4$ by sodium citrate and tannic acid.
Figure 6D:
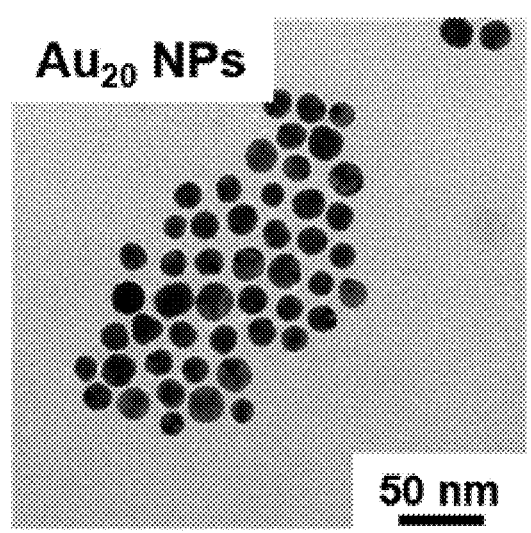
FIG. 6D shows TEM images of AuNPs with a diameter of ~20 nm as synthesized via the reduction of $HAuCl_4$ by sodium citrate.
Figure 7A:
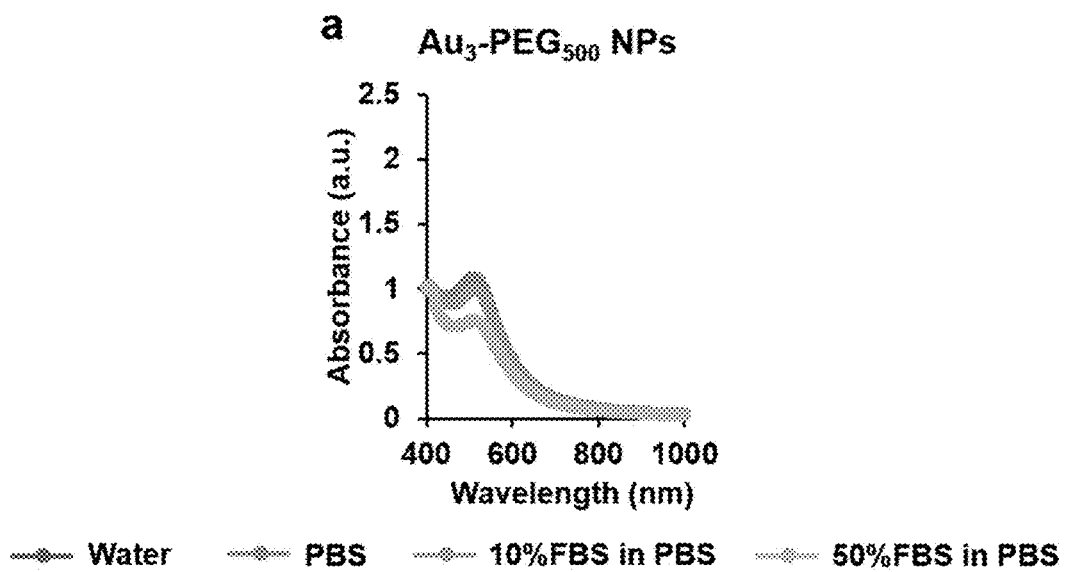
FIG. 7A shows UV-Vis spectra of $Au_3$-$PEG_{500}$ NPs after incubation in PBS, PBS supplemented with 10% FBS, or 50% FBS at 37° C. for 24 h.
Figure 7B:
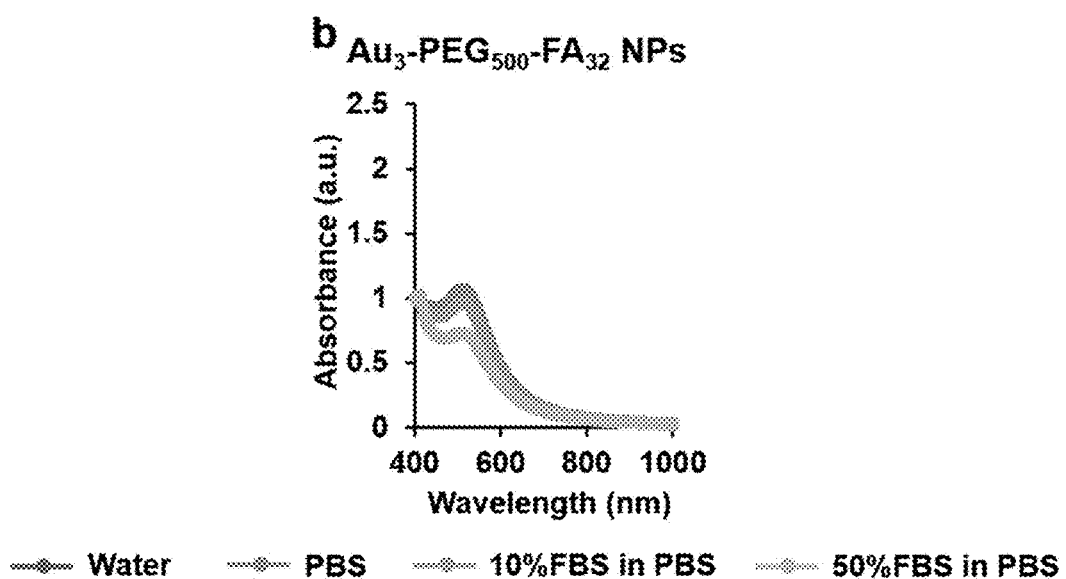
FIG. 7B shows UV-Vis spectra of $Au_3$-$PEG_{500}$-FA NPs after incubation in PBS, PBS supplemented with 10% FBS, or 50% FBS at 37° C. for 24 h.
Figure 7C:
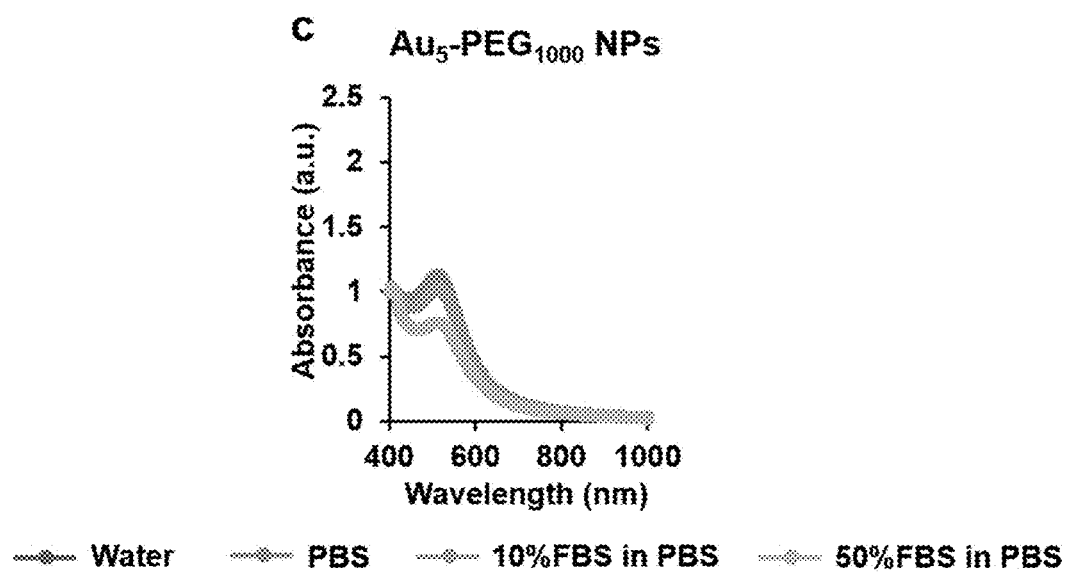
FIG. 7C shows UV-Vis spectra of $Au_5$-$PEG_{1000}$ NPs after incubation in PBS, PBS supplemented with 10% FBS, or 50% FBS at 37° C. for 24 h.
Figure 7D:
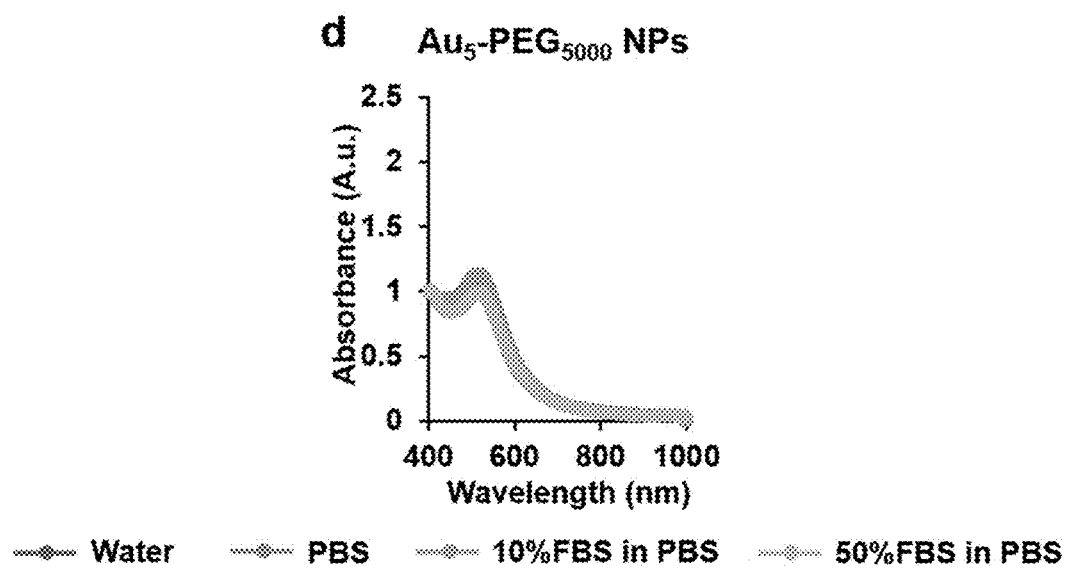
FIG. 7D shows UV-Vis spectra of $Au_5PEG_{5000}$ NPs after incubation in PBS, PBS supplemented with 10% FBS, or 50% FBS at 37° C. for 24 h.
Figure 7E:
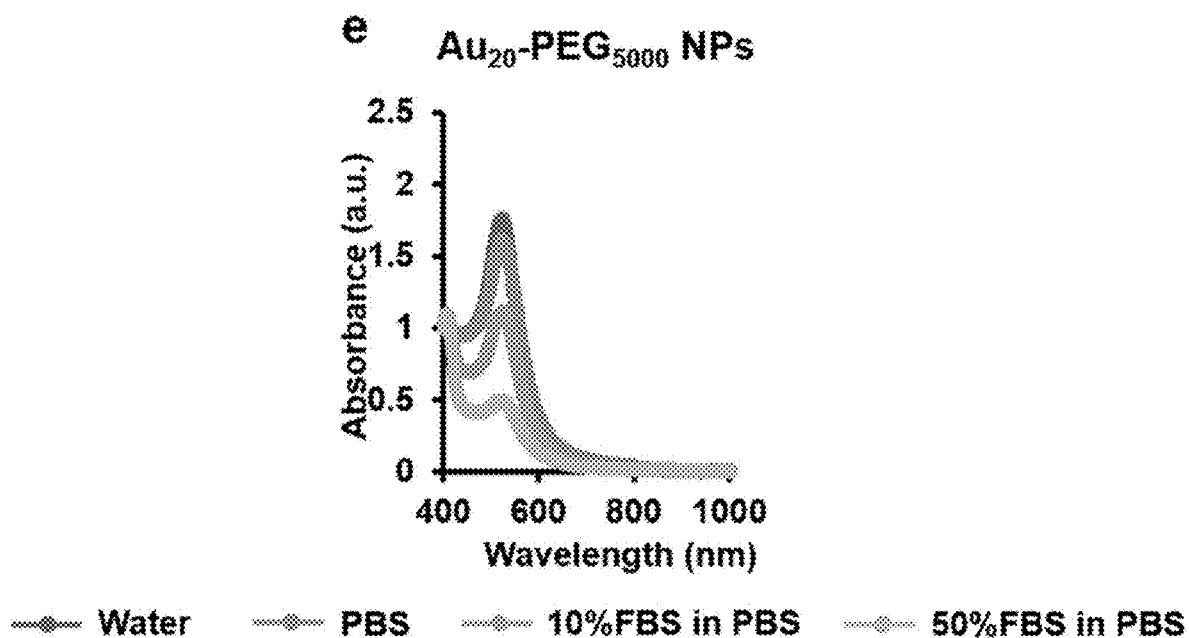
FIG. 7E shows UV-Vis spectra of $Au_{20}PEG_{5000}$ NPs after incubation in PBS, PBS supplemented with 10% FBS, or 50% FBS at 37° C. for 24 h. All spectra are normalized to the absorbance value at 400 nm.

Furthermore, the severity of renal injury and renal fibrosis were assessed on Day 7, Day 14, and Day 28 post surgery. Data showed that as the disease progressed, the weight of the UUO kidney decreased, while the weight of the CL kidney increased (FIG. 4). The reduction of UUO kidney weight was due to the loss of kidney tissue mass followed by tubular injury and cell death[1]. The increase in weights of the CL kidney was in response to the functional renal compensatory changes caused by the UUO surgery[1,2]. In addition, PAS staining and IHC staining of the kidney sections showed progressive degeneration of the renal tubules. Starting from Day 7 after UUO surgery, dilatation of collecting ducts was evident. After 7 days of obstruction, the tubular epithelial cells were flattened and lost their cuboidal shape (FIG. 5A). On Day 14 and Day 28 after UUO surgery, less intact tubule segments were observed from the tissue sections. In the CL kidneys, the deposition of type I collagen was only evident on Day 28 after UUO surgery (FIG. 5B), maybe due to the increased burden in response to loss of function of the UUO kidney. In addition, α-SMA expression in the CL kidneys was restricted to the wall of the arterioles (FIG. 5C). These results were consistent with the reported outcome of UUO surgery[1,3,4] and confirmed the development of the established animal model with CKD.

Example 2—Characterization of AuNPs

TEM images reveal the morphologies AuNPs obtained after different growth steps (FIGS. 6A, 6B, 6C, and 6D) and confirm the size and shape uniformity of AuNPs of all sizes. The physical size of the $Au_2$-$PEG_{200}$ NPs, $Au_3$ NPs, $Au_5$ NPs and $Au_{20}$ NPs are 2.29±0.57 nm, 3.29±0.28 nm, 4.8±0.6 nm, and 18.9±2.7 nm respectively.

In order to prevent non-specific protein adsorption and particle aggregation in serum[51], thiolated polyethylene glycol (PEG) strands were covalently attached to the surface of AuNPs to form $Au_x$—$PEG_y$ NPs. The change of hydrodynamic sizes measured by DLS validated the conjugation of PEG strands onto the $Au_x$ NPs (Table 1 Diameters, Surface and Loading Density of NPs).

TABLE 1

Diameters, surface charges, and loading density of the NPs

| Sample | Physical diameter (nm)[a] | Hydrodynamic diameter in water at RT (nm)[b] | ζ-potential in 1 mM KCl at RT (mV)[c] | No. of PEG strands/particle | No. of PEG strands/nm² |
|---|---|---|---|---|---|
| $Au_3$ NPs | 3.3 ± 0.3 | 3.9 ± 1.3 (0.01 ± 0.0) | −1.5 ± 0.1 | N.A. | N.A. |
| $Au_5$ NPs | 4.8 ± 0.6 | 6.1 ± 0.2 (0.03 ± 0.0) | −6.4 ± 0.4 | N.A. | N.A. |

TABLE 1-continued

Diameters, surface charges, and loading density of the NPs

| Sample | Physical diameter (nm)[a] | Hydrodynamic diameter in water at RT (nm)[b] | ζ-potential in 1 mM KCl at RT (mV)[c] | No. of PEG strands/ particle | No. of PEG strands/ nm² |
|---|---|---|---|---|---|
| Au$_{20}$ NPs | 18.9 ± 2.7 | 22.1 ± 0.7 (0.2 ± 0.0) | −14.3 ± 0.2 | N.A. | N.A. |
| Au$_2$—PEG$_{200}$ NPs | 2.3 ± 0.6 | 3.1 ± 1.0 (0.1 ± 0.1) | −2.8 ± 1.7 | 164 ± 6.5 | 13 ± 0.5 |
| Au$_3$—PEG$_{500}$ NPs | 3.5 ± 0.3 | 9.6 ± 0.2 (0.0 ± 0.0) | −2.0 ± 2.5 | 81 ± 7.8 | 2.3 ± 0.2 |
| Au$_3$—PEG$_{500}$—FA NPs | 3.5 ± 0.5 | 9.1 ± 1.4 (0.1 ± 0.0) | −8.4 ± 1.4 | 32 ± 6.3 | 0.9 ± 0.2 |
| Au$_5$—PEG$_{1000}$ NPs | 4.8 ± 0.6 | 11.5 ± 1.8 (0.0 ± 0.0) | −1.2 ± 2.9 | 225 ± 12 | 2.9 ± 0.1 |
| Au$_5$—PEG$_{5000}$ NPs | 5.3 0.8 | 23.8 ± 0.9 (0.0 ± 0.0) | −1.2 ± 0.5 | 90 ± 29 | 1.1 ± 0.4 |
| Au$_{20}$—PEG$_{5000}$ NPs | 19.7 ± 2.0 | 46.7 ± 0.8 (0.2 ± 0.0) | −2.6 ± 0.7 | 2794 ± 365 | 2.2 ± 0.3 |

[a]Physical diameters were measured by TEM. At least 20 NPs were counted. [b,c]Hydrodynamic diameter and ζ-potential were measured by dynamic light scattering (DLS) at room temperature (RT). Numbers in parentheses refer to the polydispersity index (PDI). All reported data represent mean ± SD from three independent measurements.

Furthermore, we confirmed the colloidal stability of Au$_x$-PEG$_y$ NPs in phosphate-buffered saline (PBS), 10% fetal bovine serum (FBS) in PBS, and 50% FBS in PBS. UV-vis spectrophotometry data confirm that the LSPR peaks of Au$_x$-PEG$_y$ NPs do not change drastically after incubation in PBS or FBS containing PBS at 37° C. for 24 h (FIGS. 7A-7E). The absence of absorbance peaks around the 1000 nm region from the UV-Vis spectrum indicates that the NPs did not aggregate. By DLS measurements, the hydrodynamic sizes of Au$_x$-PEG$_y$ NPs remain consistent before and after the exposure to salt- and serum-containing medium at 37° C. for 24 h. We did not include 100% FBS in the stability test because a high concentration of serum proteins causes intense light scattering and interferes with DLS measurement. All data considered, we confirm the synthesis of AuNPs of different core sizes and that the Au$_x$-PEG$_y$ NPs are stable in serum. (Note that the LSPR peak of Au$_2$-PEG$_{200}$ NPs is not detectable by UV-vis spectrophotometry.) Visual inspection of Au$_2$-PEG$_{200}$ NPs (FIG. 8A) and Au$_2$—PEG$_{200}$-FA NPs (FIG. 8B) showed that Au$_2$-PEG$_{200}$-FA NPs were not soluble in water.

TABLE 2

Hydrodynamic Diameters of NPs incubated in PBS, 10% FBS, and 50% FBS

| Sample | Hydrodynamic diameters (nm) at RT[a] | | | |
|---|---|---|---|---|
| | water | PBS | 10% FBS in PBS | 50% FBS in PBS |
| Au$_3$—PEG$_{500}$ NPs | 9.6 ± 0.2 (0.0 ± 0.0) | 10.7 ± 1.7 (0.0 ± 0.0) | 10.4 ± 1.3 (0.2 ± 0.1) | 12.3 ± 1.3 (0.6 ± 0.1) |
| Au$_3$—PEG$_{500}$—FA$_{32}$ NPs | 9.1 ± 1.4 (0.1 ± 0.0) | 10.5 ± 0.8 (0.1 ± 0.0) | 9.4 ± 3.3 (0.2 ± 0.1) | 12.1 ± 1.6 (0.5 ± 0.1) |
| Au$_5$—PEG$_{1000}$ NPs | 11.5 ± 1.8 (0.0 ± 0.0) | 10.1 ± 1.9 (0.1 ± 0.0) | 10.9 ± 1.3 (0.6 ± 0.0) | 14.2 ± 3.8 (0.6 ± 0.0) |
| Au$_5$—PEG$_{5000}$ NPs | 20.8 ± 0.9 (0.0 ± 0.0) | 21.0 ± 2.5 (0.3 ± 0.1) | 20.3 ± 3.3 (0.3 ± 0.1) | 25.6 ± 2.3 (0.5 ± 0.1) |
| Au$_{20}$—PEG$_{5000}$ NPs | 46.7 ± 0.8 (0.2 ± 0.0) | 47.1 ± 1.3 (0.2 ± 0.0) | 47.7 ± 3.5 (0.6 ± 0.0) | 48.1 ± 5.8 (0.6 ± 0.0) |

[a]Hydrodynamic diameters were measured by dynamic light scattering. Numbers in parentheses refer to the polydispersity index (PDI). All reported data represent mean ± SD from three independent measurements. RT = room temperature.
(Note that Au$_2$—PEG$_{200}$ NPs are too small to be detected by DLS for measuring their hydrodynamic diameter.)

Example 3—Organ Level Distribution of NPs in UUO Mice

Figure 10A:
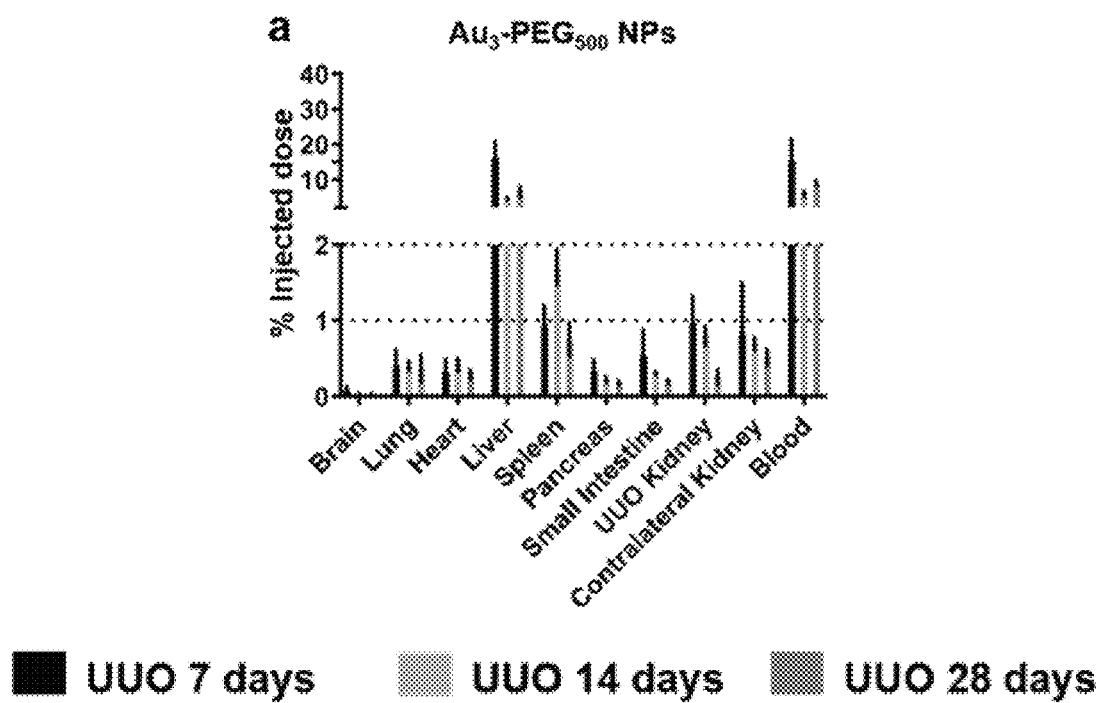
FIG. 10A shows the distribution of $Au_3$-$PEG_{500}$ NPs 24 h post-tail vein injection in mice that have undergone UUO 7, 14, and 28 days before NP injection.
Figure 10B:
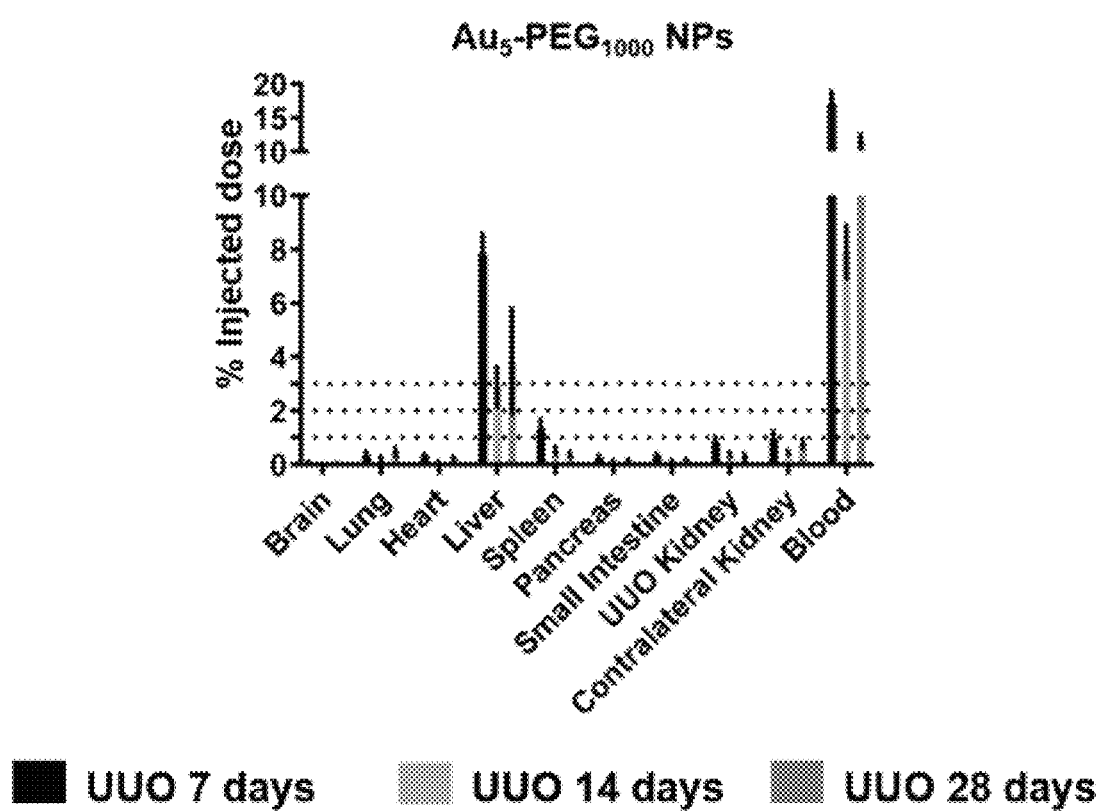
FIG. 10B shows the distribution of $Au_5$-$PEG_{1000}$ NPs 24 h post-tail vein injection in mice that have undergone UUO 7, 14, and 28 days before NP injection.
Figure 10C:
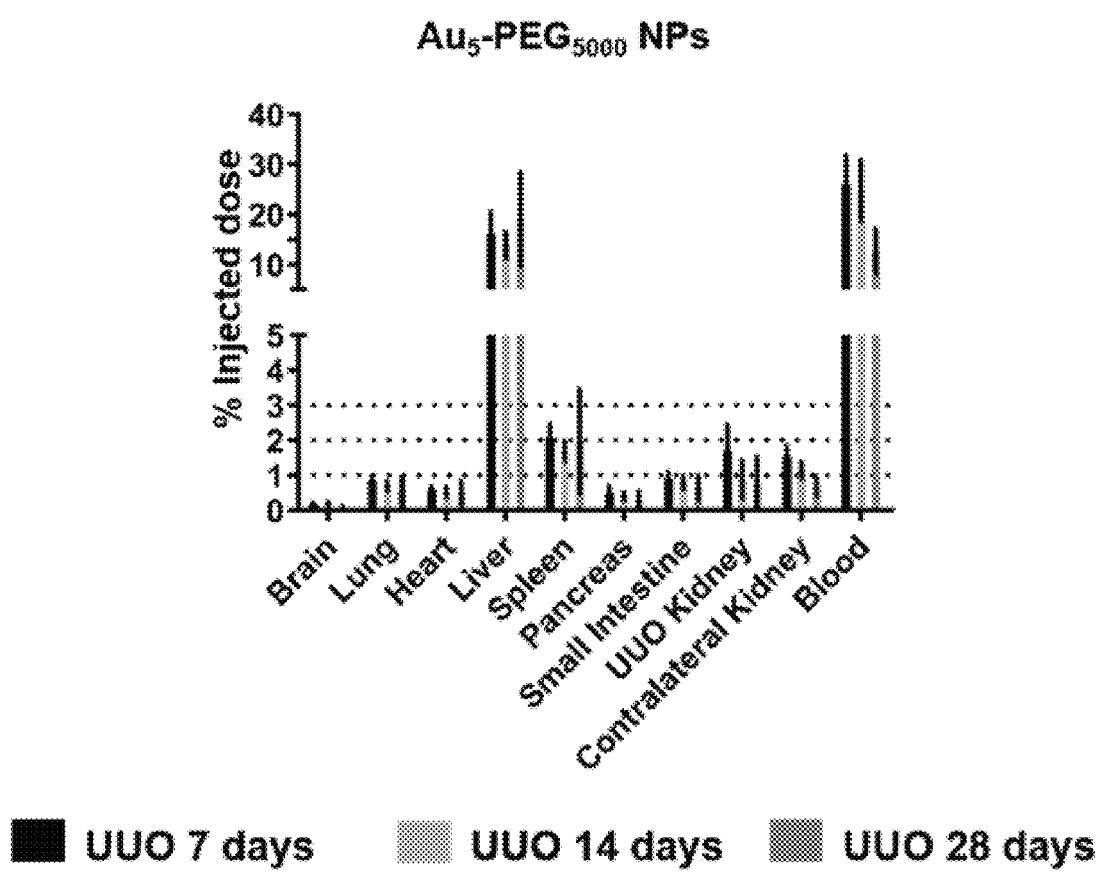
FIG. 10C shows the distribution of $Au_5$-$PEG_{5000}$ NPs 24 h post-tail vein injection in mice that have undergone UUO 7, 14, and 28 days before NP injection.
Figure 10D:
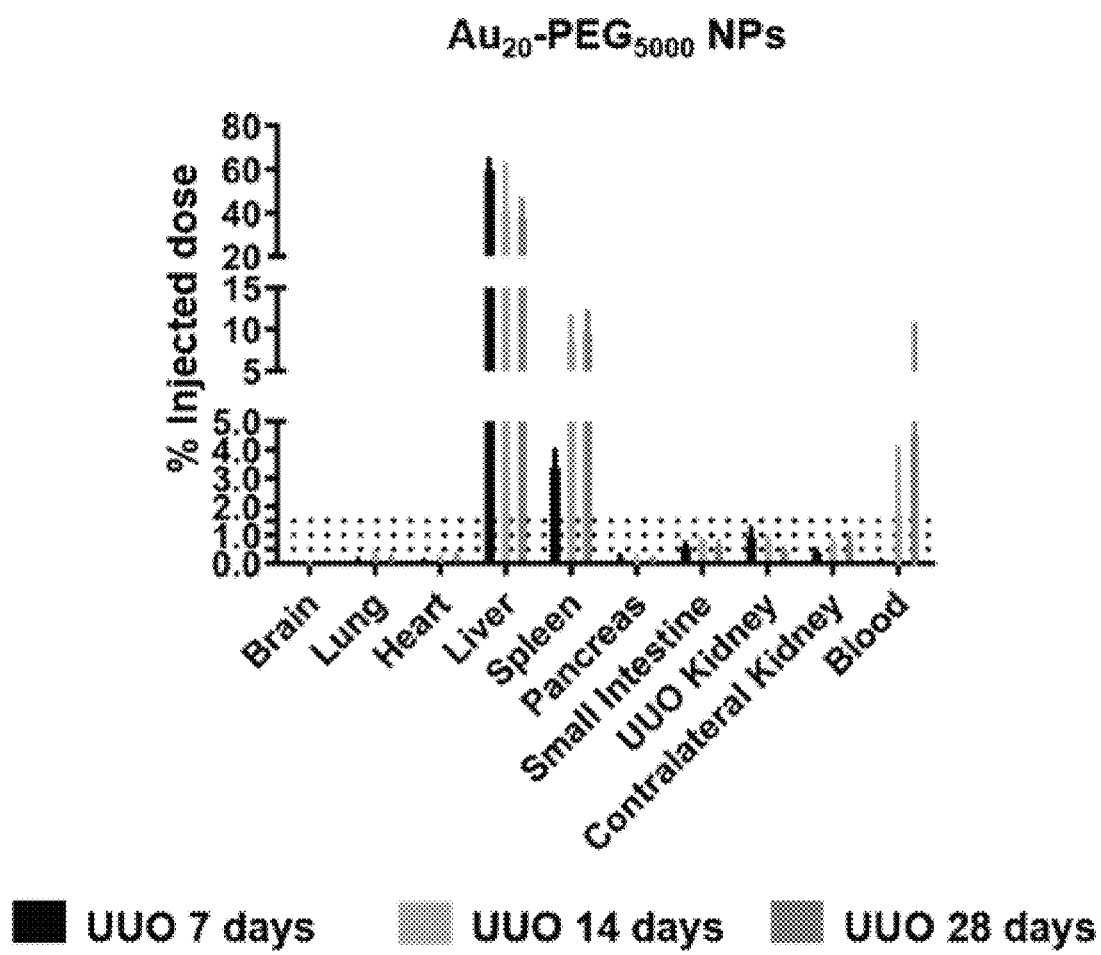
FIG. 10D shows the distribution of $Au_{20}$-$PEG_{5000}$ NPs 24 h post-tail vein injection in mice that have undergone UUO 7, 14, and 28 days before NP injection.

The aim of this experiment is to evaluate the effect of particle size and disease stage on NPs distribution in UUO mice. In this experiment, the different disease stages are characterized by the number of days of kidney obstruction, namely, the three different disease stages are UUO Day 7, UUO Day 14, and UUO Day 28. Mice were injected with 100 μg of Au$_3$-PEG$_{500}$ NPs, Au$_5$-PEG$_{1000}$ NPs, Au$_5$—PEG$_{5000}$ NPs, and Au$_{20}$PEG$_{5000}$ NPs and sacrificed 24 h after NPs injection. Then the organs (brain, lung, heart, liver, spleen, pancreas, small intestine and kidneys) and blood were extracted for the detection of bulk gold content using ICP-MS. The amount of gold in each organ is normalized to the percent of injected dose (% ID). Overall, majority of the NPs accumulate in the liver after an i.v. injection irrespective of NP size and disease stage (FIGS. 10A, 10B, 10C, and 10D). Surprisingly, the accumulation of Au$_3$-PEG$_{500}$ NPs, Au$_5$-PEG$_{1000}$ NPs and Au$_{20}$-PEG$_{5000}$ NPs in the liver was affected by the disease stage of the UUO kidney (FIGS. 10A, 10B, and 10D). For example, the accumulation of Au$_{20}$-PEG$_{5000}$ NPs in the liver dropped from 59.6±4.8% ID on UUO Day 7 to 39.4±8.2% ID on UUO Day 28 (p<0.0001).

Example 4—Effects of Disease Stage on NP Distribution in the Kidneys in UUO Mice In general, in the UUO kidney, the accumulation of Au$_x$-PEG$_y$ NPs was the highest if the NPs were injected on Day 7 post-surgery. However, as the disease progressed to Day 28, the accumulation of Au$_x$-PEG$_y$ NPs in the UUO kidney 24 h post-injection decreased dramatically. For example, a 6-fold (p=0.018) decrease in Au$_5$-PEG$_{5000}$ NPs accumulation in the UUO kidney was observed when the NPs were injected on UUO Day 28 (0.2±0.0% ID) as compared to UUO Day 7 (1.3±0.2% ID) (FIG. 10C). The accumulation of NPs in the kidneys for Au$_{20}$-PEG$_{5000}$ NPs in UUO kidney were 0.9±0.4% ID for UUO Day 7, 0.8±0.1% ID for UUO Day 14, and 0.4±0.1% ID for UUO Day 28 (FIG. 10D).

The observed pattern of NP accumulation in different disease stages could be due to the loss of kidney mass as the disease progressed. However, this concept does not apply to the CL kidney, as the pathological changes in the CL kidneys were minimal for all disease stages. Yet, as the disease progressed, a decrease in delivery to the CL kidneys of UUO mice injected with Au$_5$-PEG$_{5000}$ NPs was observed, with a 6.5-fold (p=0.004) decrease in NP accumulation when the NPs were injected on UUO Day 28 (0.2±0.0% ID) as compared to UUO Day 7 (1.4±0.4% ID) (FIG. 10C). Surprisingly, a positive correlation was observed between disease stage and $Au_{20}$-$PEG_{5000}$ NPs accumulation in the CL kidney (FIG. 10D). The accumulation of $Au_{20}$-$PEG_{5000}$ NPs in CL kidney were 0.4±0.1% ID for UUO Day 7, 0.7±0.0% ID for UUO Day 14, and 1.0±0.2% ID for UUO Day 28 (p=0.002 when compared with UUO Day 7). These data confirmed that the same NPs when injected into UUO mice at different disease stages showed different distribution patterns.

Example 5—Organ and Tissue Distribution

Because disease stage appeared to affect the delivery of AuNPs to the kidneys, the studies were focussed on one disease stage—UUO Day 7, for determining the effects of size and targeting ligands on renal delivery. UUO mice (Day 7 post surgery) were injected with 100 µg of $Au_x$-$PEG_y$ NPs of various NP core diameters (x; in nm) and PEG molecular weights (y; in Da) and sacrificed 24 h after NPs injection. Then the kidneys (FIG. 10E) and blood (FIG. 10G) were extracted for the detection of gold content by inductively coupled plasma mass spectrometry (ICP-MS). Data showed that NPs with a hydrodynamic diameter of ~3.3 nm accumulated in the UUO (1.8±0.76% ID) and contralateral (CL) (3.1±0.42% ID) kidneys more efficiently than larger NPs (FIG. 10E) at the organ level. While the delivery of $Au_3$-$PEG_{500}$, $Au_5$-$PEG_{1000}$, $Au_5$-$PEG_{5000}$, and $Au_{20}$—$PEG_{5000}$ NPs, to the UUO kidneys were not statistically different at the organ level, their distribution at the tissue level as shown by silver enhancement staining (FIG. 10F) demonstrated that NPs with an overall hydrodynamic diameter less than 10 nm efficiently crossed the glomerulus barrier and entered the renal tubule cells. These results demonstrated that even though the AuNPs accumulation at the organ level was numerically similar, their tissue level distribution revealed markedly different results. Interestingly, the clearance of $Au_3$-$PEG_{500}$ NPs was also captured in this image, where the tubule lumens were stained black. The excretion kinetics of AuNPs that have a hydrodynamic diameter smaller than 10 nm ($Au_2$—$PEG_{200}$, 3.1±1.0 nm and $Au_3$—$PEG_{500}$ NPs, 9.6±1.4 nm), and AuNPs that have a hydrodynamic diameter just above 10 nm ($Au_5$-$PEG_{1000}$, 11.5±1.8 nm) were studied. Since $Au_2$-$PEG_{200}$-FA NPs are insoluble in water (FIG. 8B), the rest of the studies focused on $Au_3$-$PEG_{500}$ and $Au_3$—$PEG_{500}$-FA NPs.

Figure 21A:
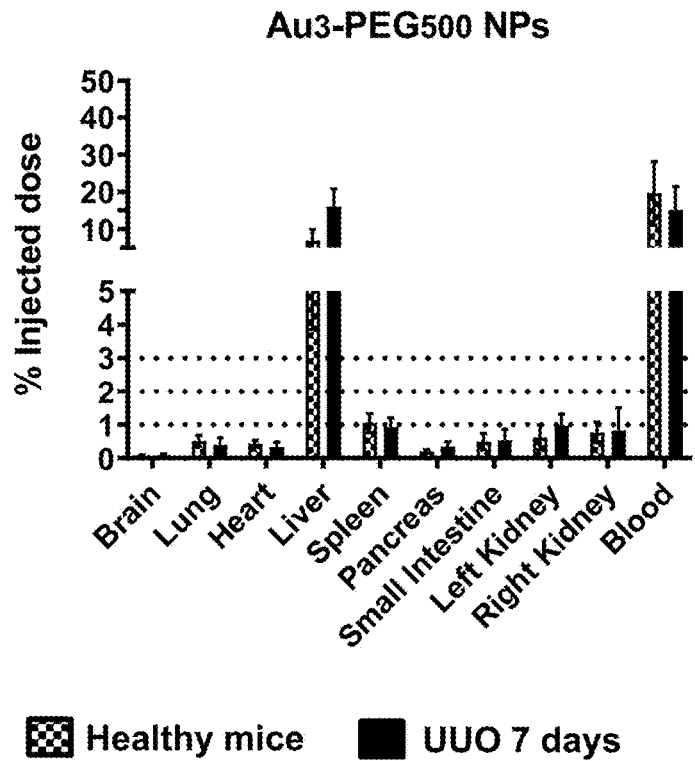
FIG. 21A shows the distribution of Au$_3$-PEG$_{500}$ NPs at organ level 24 h after injection into healthy control mice or UUO mice on day 7 after UUO surgery.
Figure 21B:
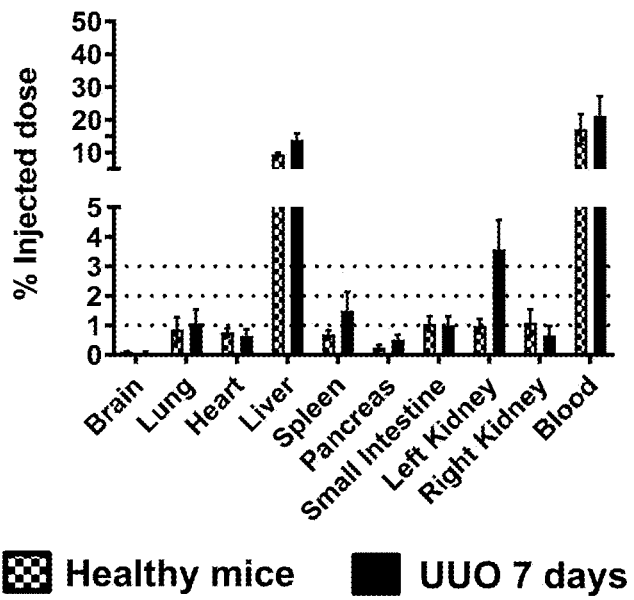
FIG. 21B shows the distribution of AU$_3$-PEG$_{500}$-FA NPs at organ level 24 h after injection into healthy control mice or UUO mice on day 7 after UUO surgery.
Figure 21C:
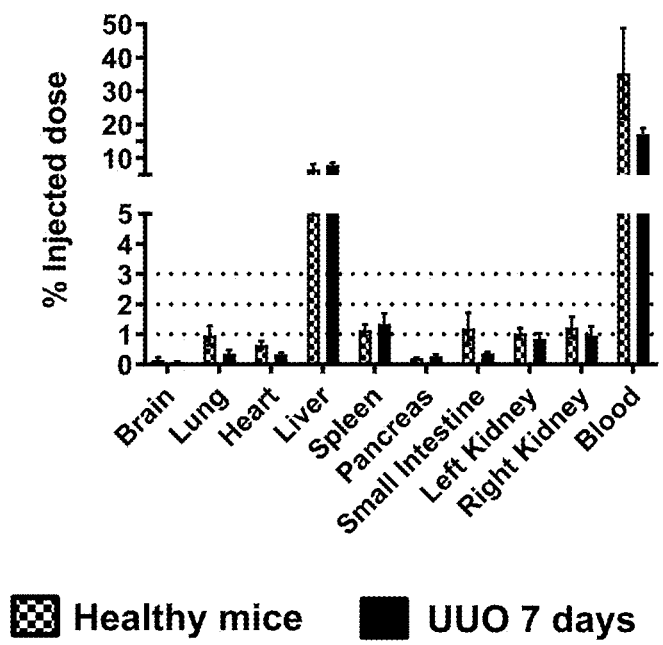
FIG. 21C shows the distribution of Au$_5$-PEG$_{1000}$ NPs at organ level 24 h after injection into healthy control mice or UUO mice on day 7 after UUO surgery.

Further, the organ distribution of $Au_3$-$PEG_{500}$ NPs, $Au_3$—$PEG_{500}$-FA NPs, and $Au_5$-$PEG_{1000}$ NPs was measured in healthy mice and in UUO-treated mice 7 days after surgery (FIGS. 21A, 21B, and 21C).

Example 6—Effect of Particle Size and Disease Stage on Blood Circulation

Twenty-four hours post-injection, blood was withdrawn through cardiac puncture from each mouse to evaluate the gold content in blood by using ICP-MS. The blood concentration of $Au_3$-$PEG_{500}$ NPs, $Au_5$—$PEG_{1000}$ NPs, and $Au_5$-$PEG_{5000}$ NPs, was the highest 24 h post-injection for all disease stages studied, except for $Au_{20}$-$PEG_{5000}$NPs (FIG. 10G). These data indicated that smaller NPs had a more prolonged blood circulation. The statistically significant difference indicated that disease stages significantly affected the blood circulation of the NPs. Therefore, these data indicated that the kidney disease had a systemic impact through the release of different cytokines, and the recruitment of immune cells.

Example 7—Renal and Hepatobiliary Clearance of AuNPs

Figure 12A:
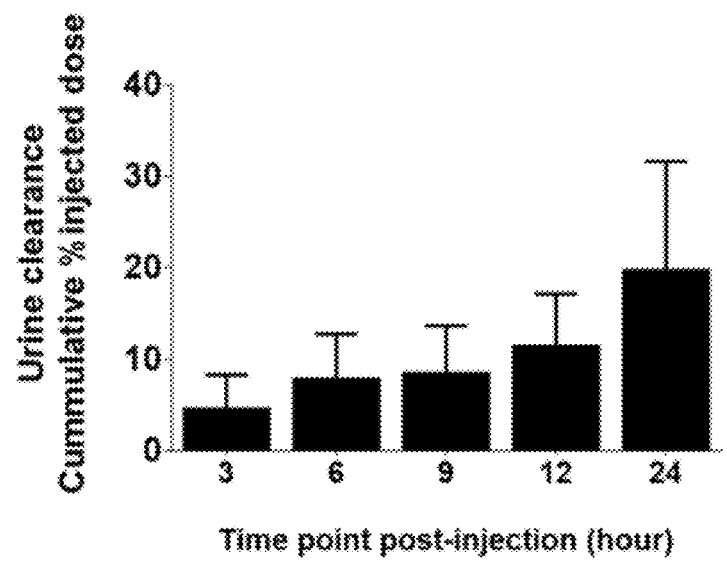
FIG. 12A shows the excretion of $Au_2$-$PEG_{200}$ NPs by renal clearance.
Figure 12B:
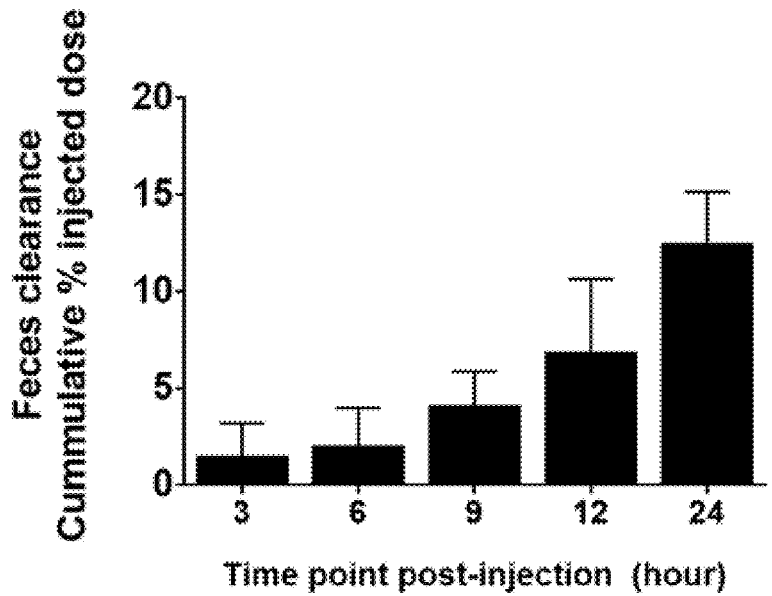
FIG. 12B shows the excretion of $Au_2$-$PEG2_{00}$ NPs by hepatobiliary clearance. Error bar denotes ±1 standard deviation, with n=3.

The excretion kinetics of AuNPs was measured by collecting urine and feces at various time points after NPs injection. The data showed that all the tested NPs could be cleared through the renal clearance and hepatobiliary clearance with various efficiencies. Since the UUO kidneys were ligated, the AuNPs detected from the urine were cleared from the CL kidneys, and the AuNPs detected in the feces were cleared through the liver, into the bile and excreted as feces. The data showed that all three types of NPs were cleared through the renal clearance and hepatobiliary clearance, with $Au_2$-$PEG_{200}$ NPs being cleared the most efficiently (urine: 19.7±11.9% ID; feces: 12.4±2.7% ID) at 24 h after injection (FIGS. 12A and 12B). The detection of $Au_2$-$PEG_{200}$ NPs in the feces in the early time point indicated that ultra-small NPs were rapidly cleared through hepatobiliary system as well. For NPs with a hydrodynamic size >5.5 nm, the hepatobiliary clearance was less than 5% ID at 24 h after injection, which is consistent with the slow hepatobiliary clearance.

Figure 22:
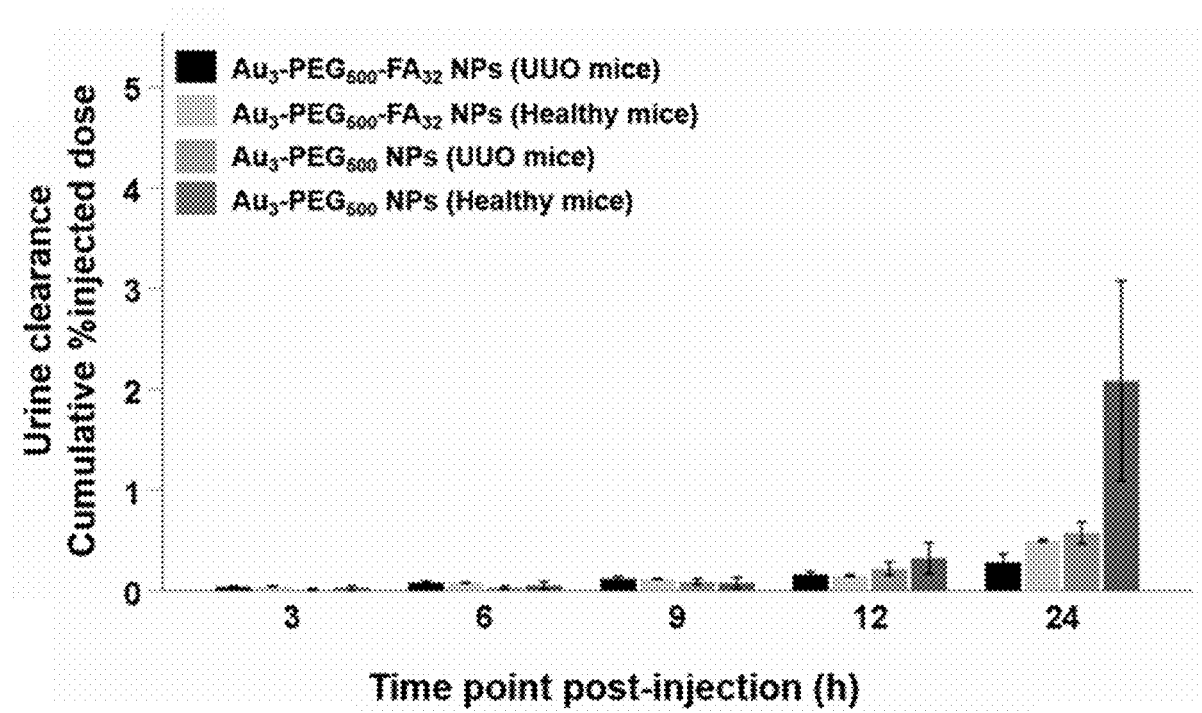
FIG. 22 shows the excretion patterns of Au$_3$-PEG$_{500}$ NPs, and Au$_3$—PEG$_{500}$-FA NPs by renal clearance. Error bar denotes ±1 standard deviation, with n=3.
Figure 23:
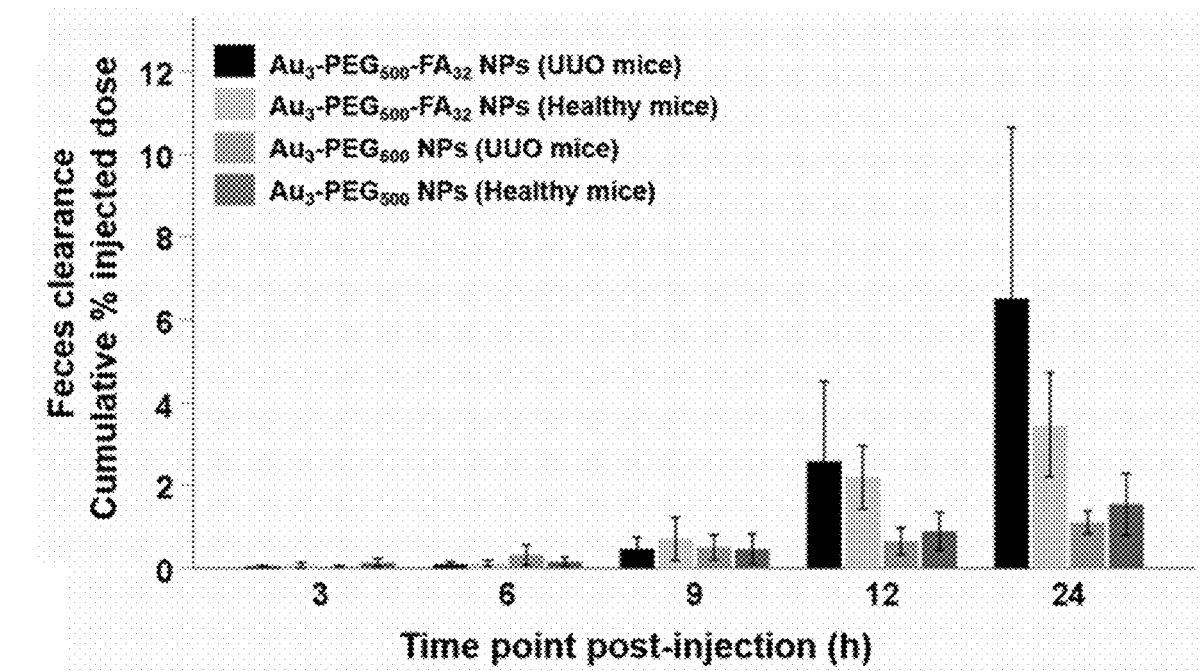
FIG. 23 shows the excretion patterns of Au$_3$-PEG$_{500}$ NPs, and Au$_3$—PEG$_{500}$-FA NPs by the hepatobiliary pathway. N=3, error bar denotes ±1 standard deviation.

The data showed that $Au_3$-$PEG_{500}$-FA NPs (FIG. 22) were excreted by renal clearance because gold was detected in the urine samples 24 h post-injection. For the hepatobiliary clearance of $Au_3$-$PEG_{500}$-FA NPs in UUO mice, the cumulative excreted amount in feces was 7.46±4.6% ID.

These data suggested renal clearable NPs were essential for renal tubule uptake, and the FA surface coating increased the efficiency of cellular uptake.

Example 8—NP Size Affects Passive Delivery to Fibrotic Kidneys

Figure 9A:
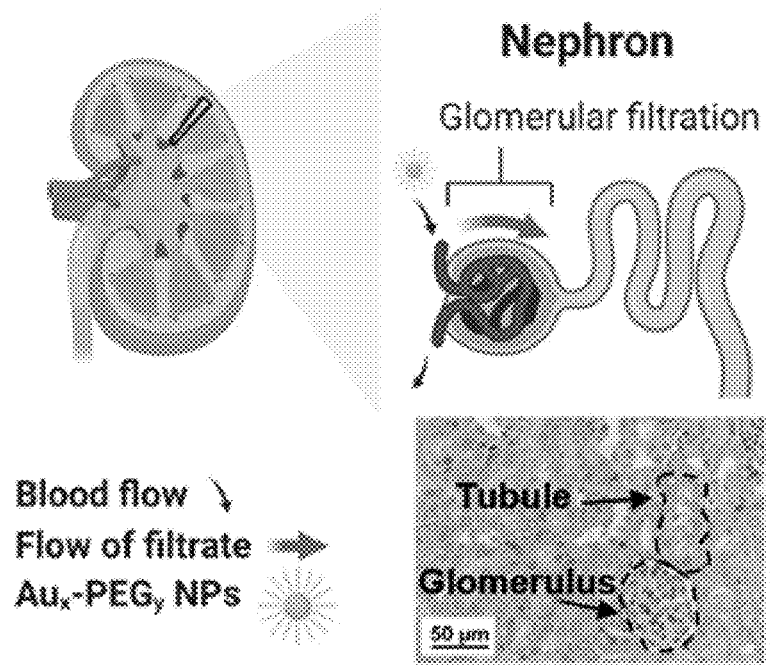
FIG. 9A shows a schematic of a kidney (left) and a nephron (right) with the small black arrows indicating the blood flow and the large red arrow indicating flow of the glomerulum filtrate.
Figure 9B:
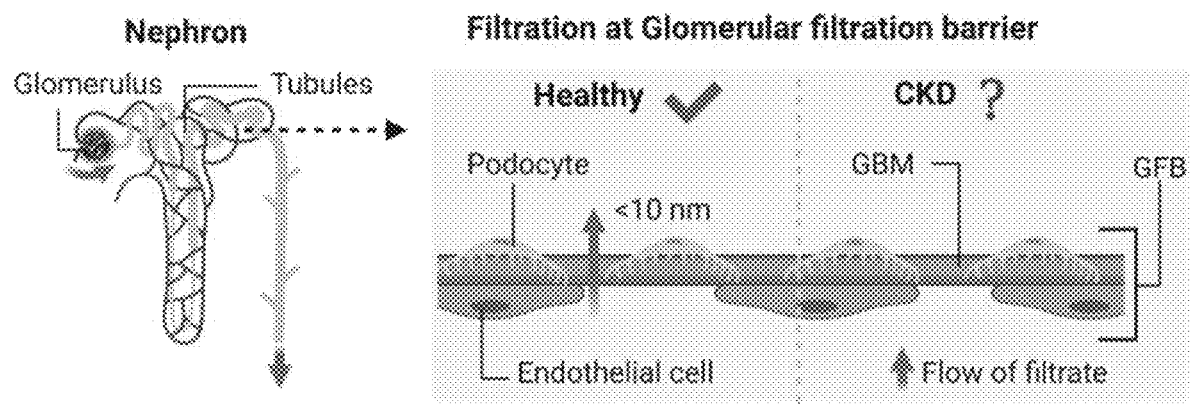
FIG. 9B (left), Schematic showing the filtration unit (glomerulus) and collection of tubules that make up a nephron, the functional unit of the glomerular filtration system.
Figure 9C:
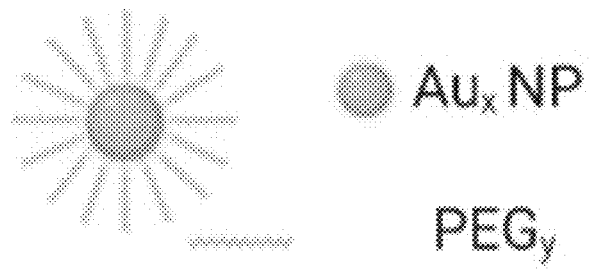
FIG. 9C, Schematic of a polyethylene glycol-coated gold nanoparticle ($Au_x$—$PEG_y$ NP) with tailorable NP core diameter (x; in nm) and PEG molecular weight (y; in Da).
Figure 9D:
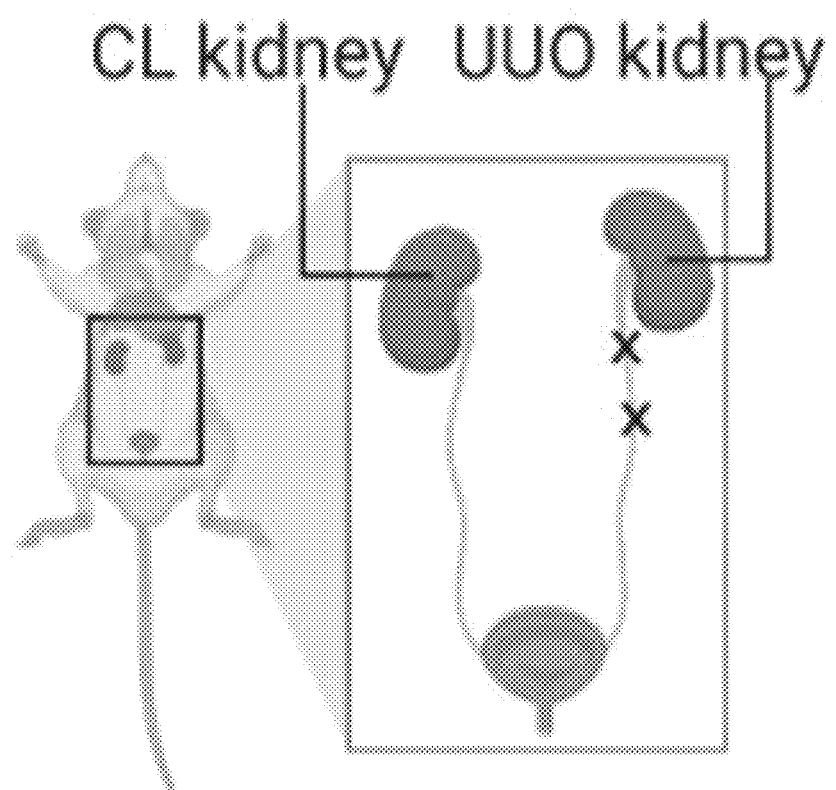
FIG. 9D, Schematic shows complete unilateral ureteral obstruction (UUO) in mice (an animal model for renal fibrosis) is obtained by ligating the left ureter twice with sutures.
Figure 9E:
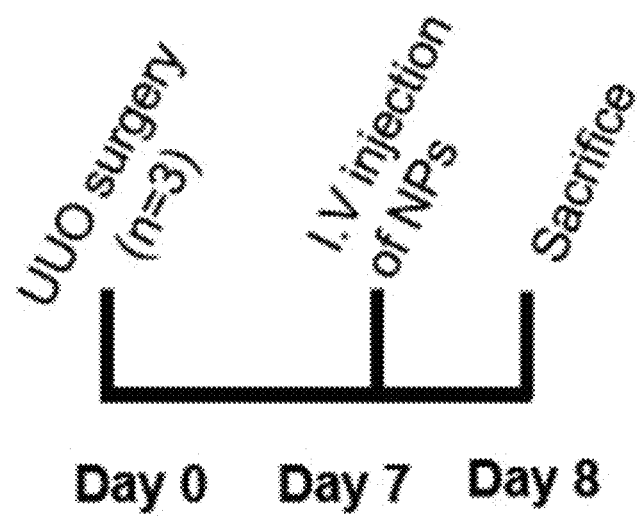
FIG. 9E shows the experimental timeline of the biodistirubtion study. Nanoparticles were intravenously (i.v.) injected 7 days after UUO surgery and sacrificed on Day 8.

To evaluate the size cutoff of NPs for crossing the GFB in UUO mice, we prepared a series of untargeted $Au_x$-$PEG_y$ NPs (FIG. 9C) with various Au core diameters (x in nm) and PEG molecular weights (y in Da) (Table 1, FIGS. 6A-6D, and Table 2). All $Au_x$-$PEG_y$ NPs were colloidally stable when incubated in 50% serum for 24 h (FIGS. 7A-7E). To study the biodistribution of the NPs, we injected the $Au_x$-$PEG_y$ NPs (100 µg in Au mass for all NP sizes studied) into UUO mice (FIG. 9E) on Day 7 post-UUO surgery and sacrificed the animals 24 h thereafter. Seven days is the time required for establishing renal fibrosis in mice.

Figure 10E:
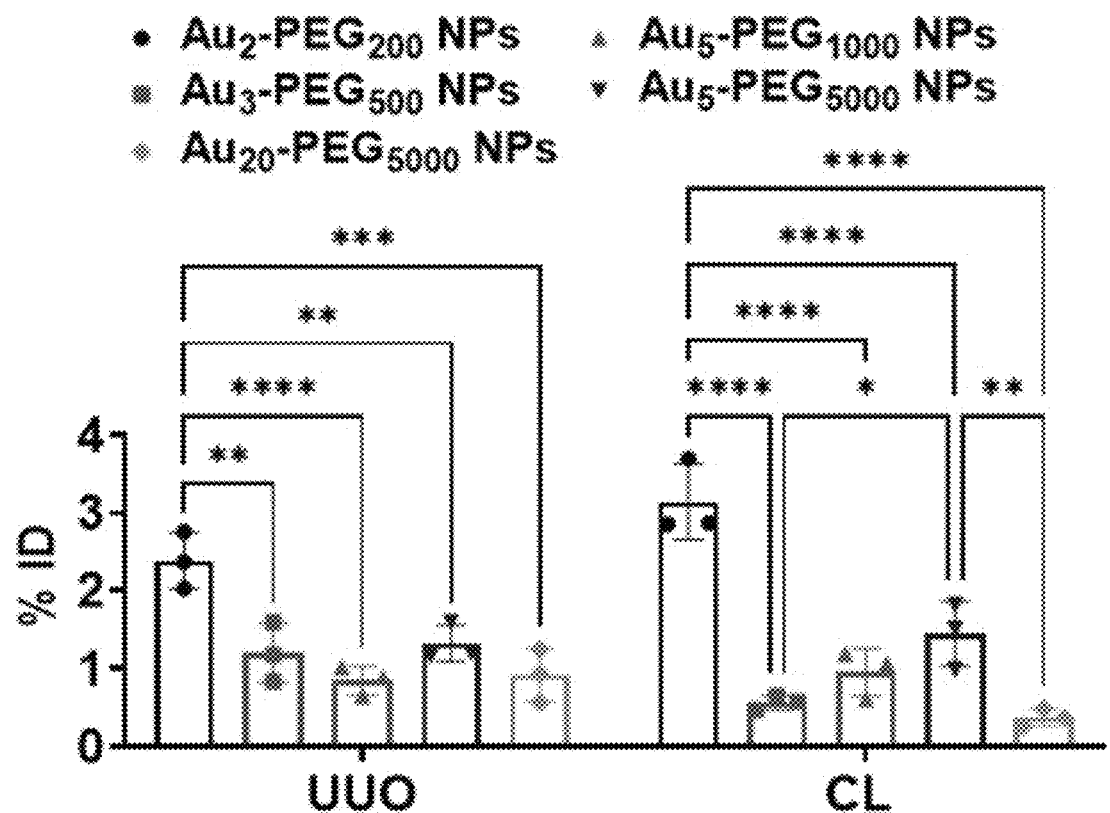
FIG. 10E shows the organ-level distribution of $Au_x$-$PEG_y$ NPs of various NP core diameters (x; in nm) and PEG molecular weights (y; in Da) in the UUO kidney and contralateral (CL) kidney 24 h post-injection. One hundred µg of each type of AuNPs were injected into mice via the tail-vein on Day 7 after the UUO surgery. *=$p \leq 0.05$, =$p \leq 0.001$, *=$p \leq 0.0001$. Error bar denotes standard deviation of 1, with n=3.
Figure 10F:
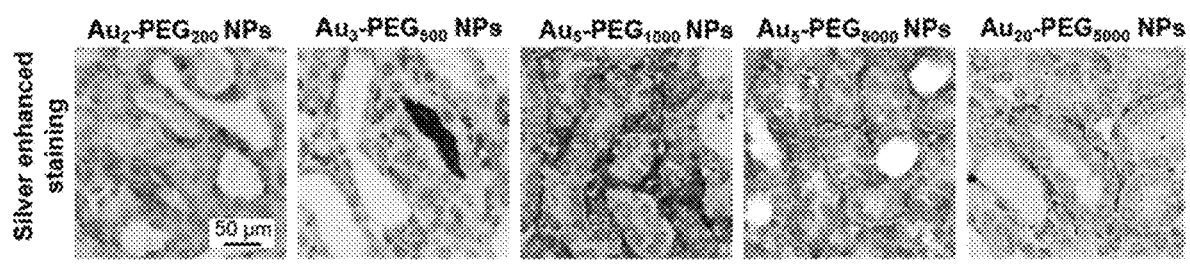
FIG. 10F shows the tissue-level distribution of $Au_x$-$PEG_y$ NPs in the UUO kidney 24 h post-injection, as revealed by silver enhancement staining with yellow/black dots indicating $Au_2$ NPs and black dots indicating AuNPs of larger sizes.
Figure 10G:
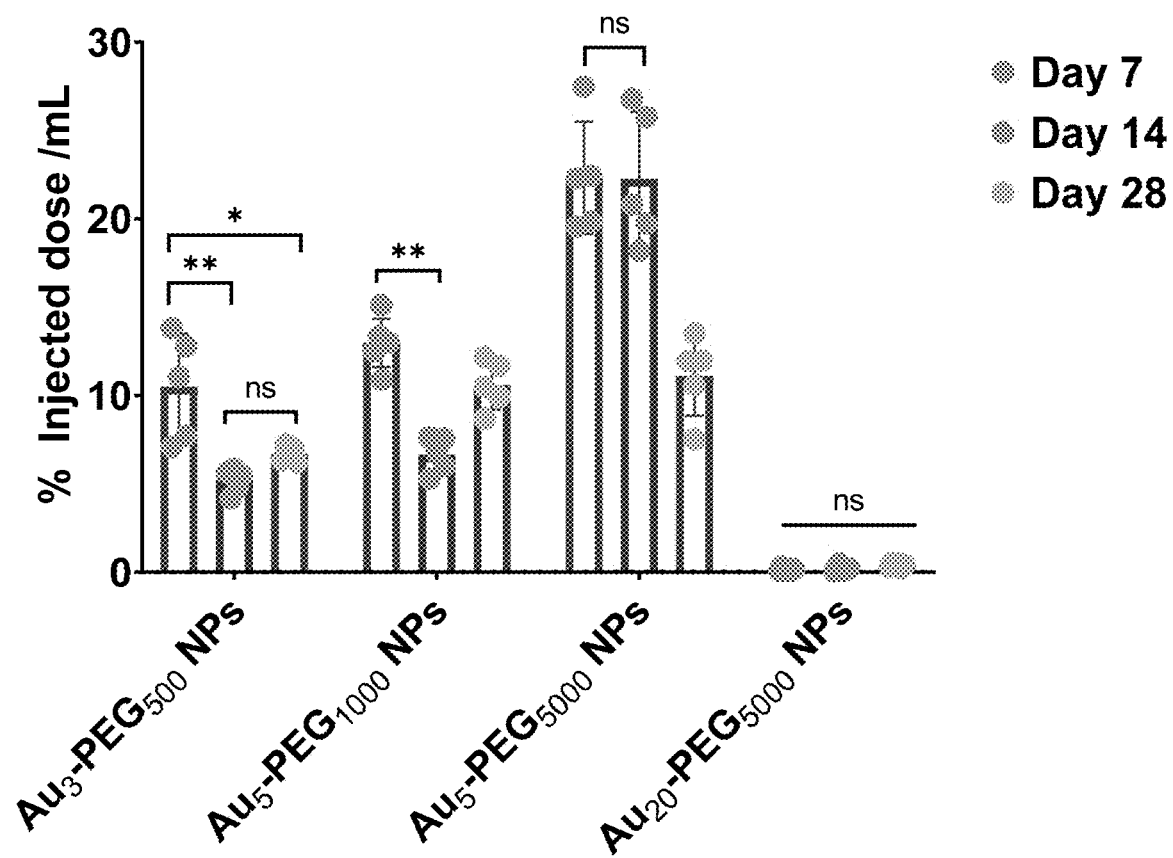
FIG. 10G shows the concentration of $Au_3$-$PEG_{500}$ NPs, $Au_5$—$PEG_{1000}$ NPs, $Au_5$—$PEG_{5000}$ NPs, and $Au_{20}$-$PEG_{5000}$ NPs in blood 24 h after tail vein injection in mice that have undergone UUO 7, 14, ad 28 days before NP injection. The amount of gold was measured by ICP-MS. *=$p \leq 0.05$, =$p \leq 0.001$, *=$p \leq 0.0001$. Error bar denotes standard deviation of 1, with n=3.
Figure 11A:
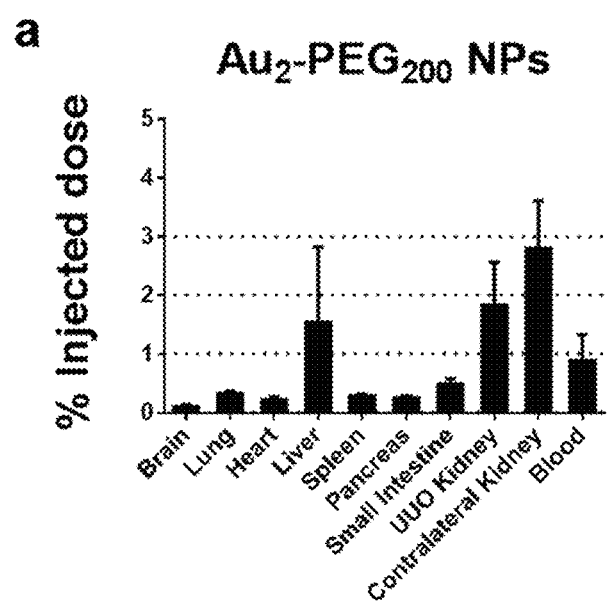
FIGS. 11A-11E Organ-level distribution for FIG. 11A, $Au_2$-$PEG_{200}$ NPs FIG. 11B, $Au_3$-$PEG_{500}$ NPs FIG. 11C, $Au_5$-$PEG_{1000}$ NPs FIG. 11D, $Au_5$—$PEG_{5000}$ NPs, and FIG. 11E, $Au_{20}$-$PEG_{5000}$ NPs. The NPs (100 µg of Au) were injected into UUO mice via the tail vein on Day 7 post-UUO surgery. 24 h post-injection, the mice were sacrificed for organ collection. The bulk gold content was detected using ICP-MS. Error bar denotes ±1 SD. Data are from n=3, across 1 experiment.
Figure 11B:
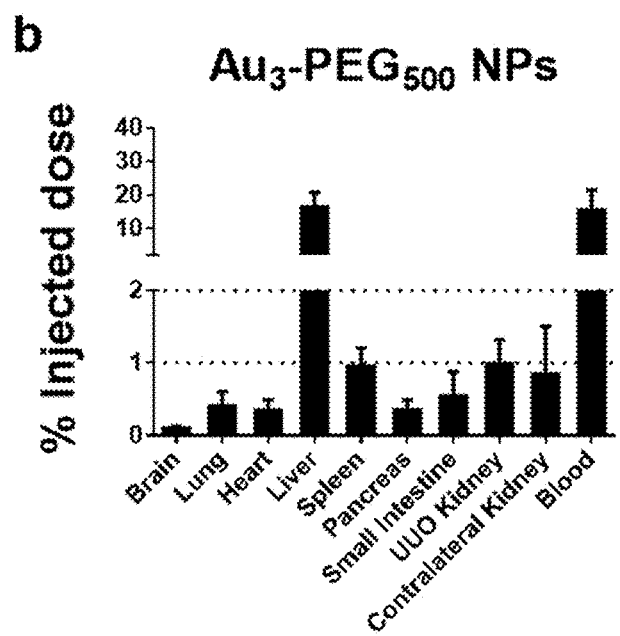
Figure 11C:
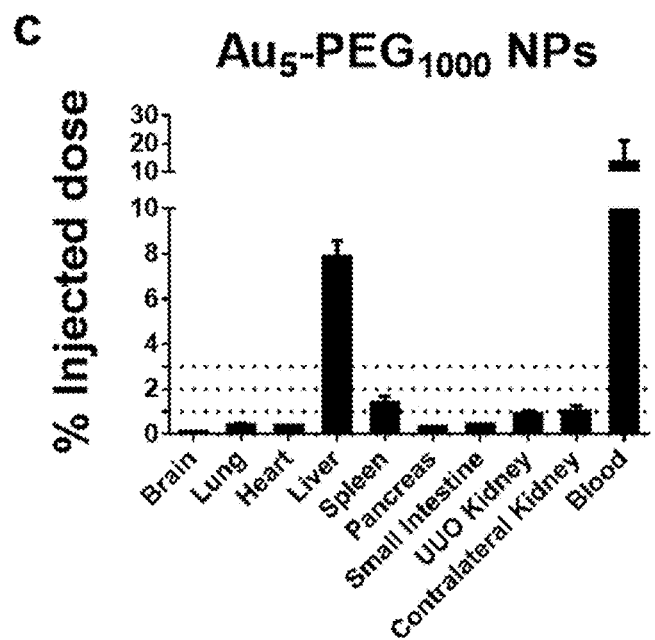
Figure 11D:
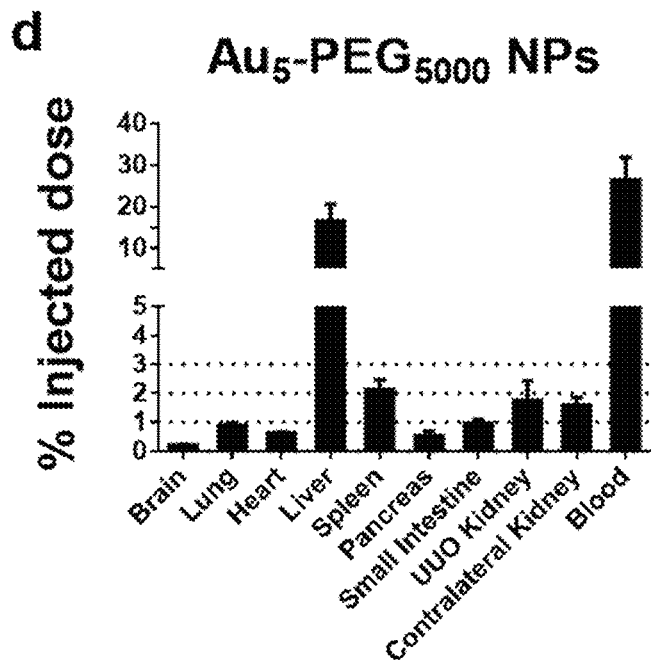
Figure 11E:
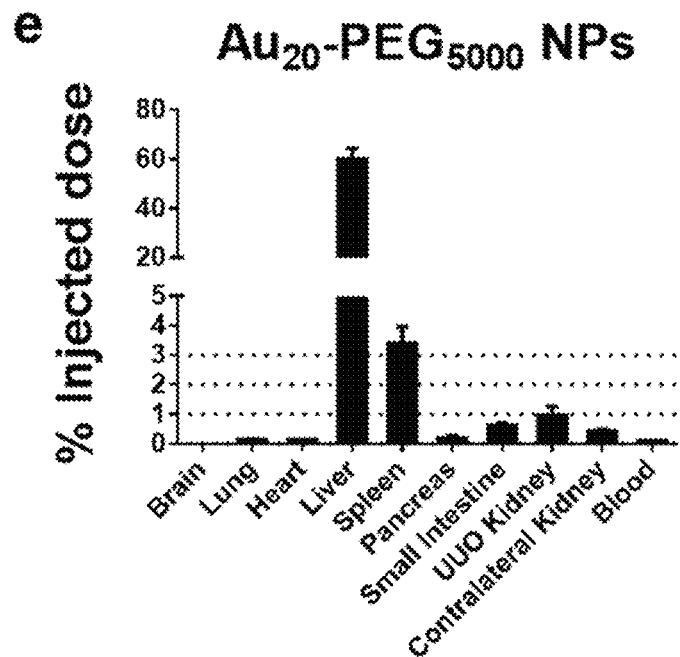

At the organ level, inductively coupled plasma-mass spectrometry (ICP-MS) data show that of the five untargeted NPs, $Au_2$—$PEG_{200}$ accumulated most abundantly in both the UUO (2.3% ID) and CL (3.1% ID) kidneys (FIG. 10E). The accumulation of $Au_3$-$PEG_{500}$, $Au_5$-$PEG_{1000}$, $Au_5$—$PEG_{5000}$, and $Au_{20}$-$PEG_{5000}$ NPs in the UUO and CL kidneys is not statistically different (~1% ID). At the tissue level, silver enhancement staining of the UUO kidney reveal both $Au_2$-$PEG_{200}$ and $Au_3$—$PEG_{500}$ NPs accumulated in the tubule lumen whereas the larger $Au_5$-$PEG_{1000}$, $Au_5$—$PEG_{5000}$ and $Au_{20}$-$PEG_{5000}$ NPs were localized in the interstitial area or blood capillaries surrounding the tubules. Kidney tissues of uninjected mice had no silver stain (FIG. 13G). These results demonstrate that only $Au_2$-$PEG_{200}$ NPs and $Au_3$—$PEG_{500}$ NPs (both <10 nm) can cross the GFB and reach the tubule lumen even though the organ-level accumulation of $Au_3$-$PEG_{500}$, $Au_5$—$PEG_{1000}$, $Au_5$—$PEG_{5000}$ and $Au_{20}$—$PEG_{5000}$ NPs in the UUO kidney is similar. Because $Au_2$-$PEG_{200}$-FA NPs are insoluble in water (FIGS. 8A-8B), we used $Au_3$-$PEG_{500}$ for all subsequent studies. FA is poorly soluble in water under neutral conditions[45] and the molecular weight of FA (441 Da) exceeds that of $PEG_{200}$.

Example 9—$AU_3$-$PEG_{500}$-FA Targets Tubules in Fibrotic Kidney

Figure 13A:
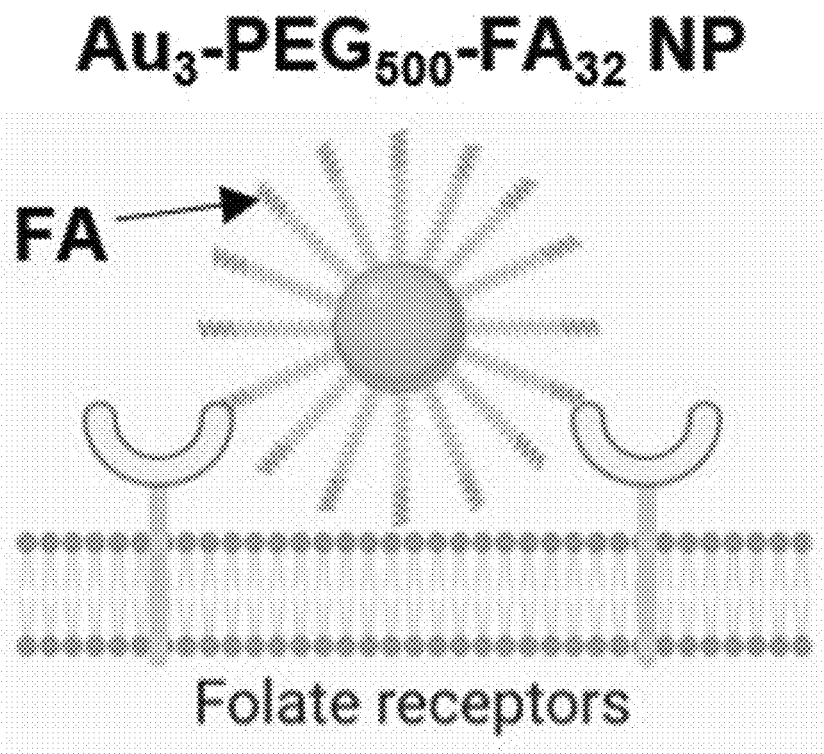
FIGS. 13A-13I $Au_3$-$PEG_{500}$-$FA_{32}$ NPs bind preferentially to folate receptor (FR) in renal tubules of fibrotic kidneys.
Figure 13B:
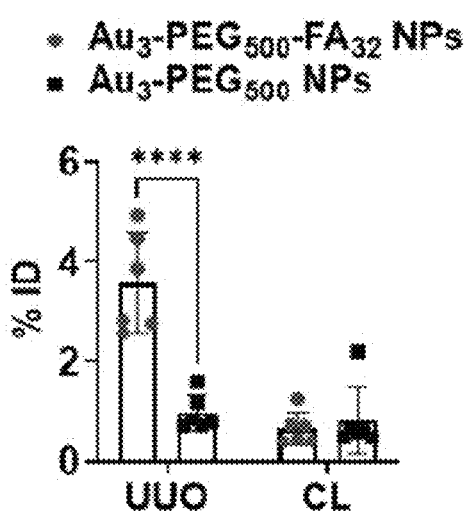
Figure 13C:
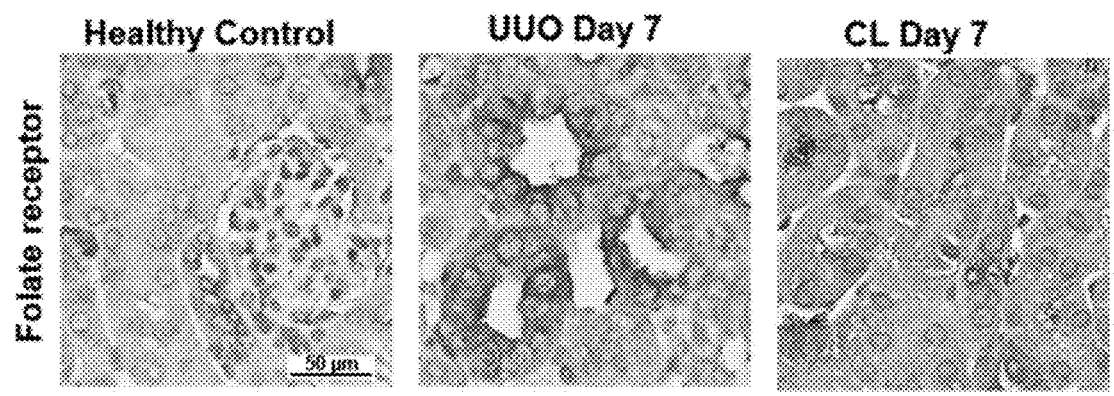
Figure 13D:
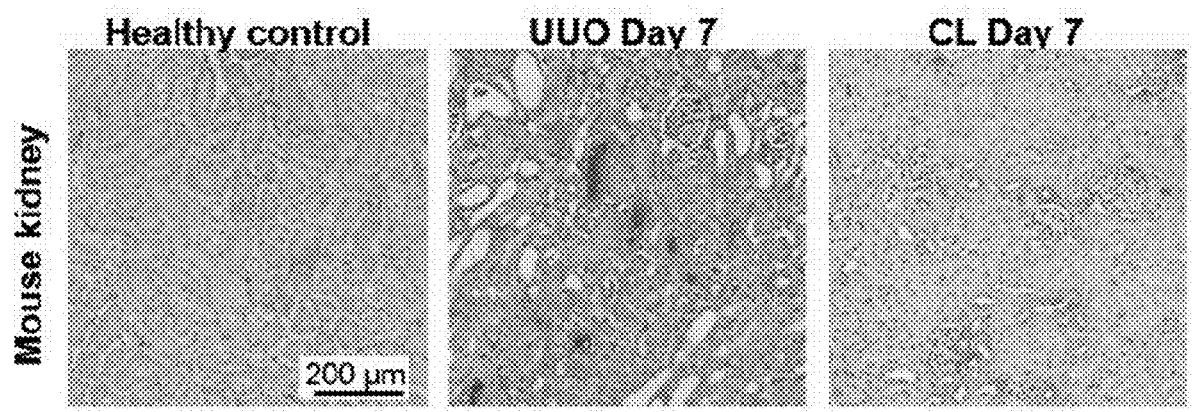
Figure 13E:
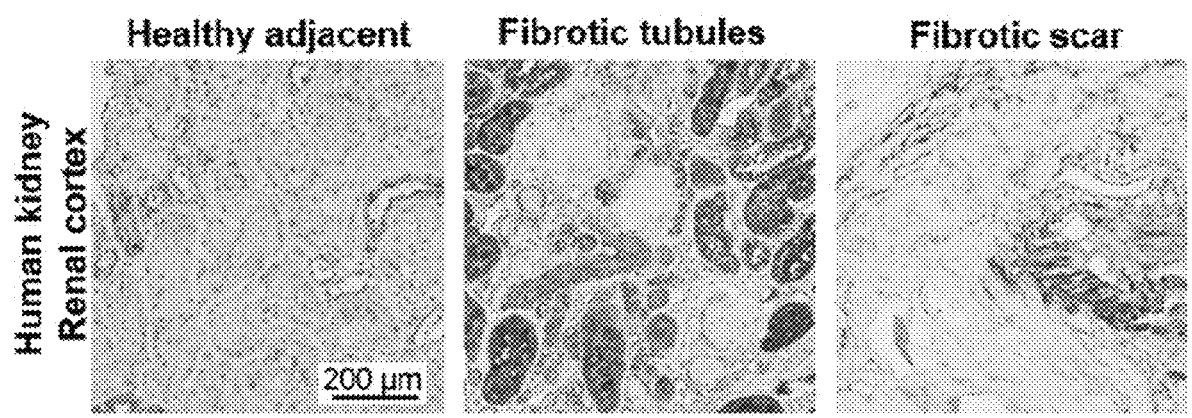

To investigate whether FA-conjugated NPs can be localized to fibrotic renal tubules of UUO mice[40], we intravenously injected the animals with the NPs and examined their accumulation in the UUO and CL kidney tissues (FIG. 13A). ICP-MS data show significantly more targeted $Au_3$-$PEG_{500}$-$FA_{32}$ NPs (3.6% ID) accumulated in the UUO kidney than untargeted $Au_3$-$PEG_{500}$ NPs (1.0% ID), while similar amounts of $Au_3$-$PEG_{500}$ NPs (0.8% ID) and $Au_3$-$PEG_{500}$-$FA_{32}$ NPs (0.7% ID) were seen in the CL kidney (FIG. 13B). Immunohistochemistry (IHC) analysis revealed an elevated local expression of FR on the apical side of selected tubule cells in the UUO kidney, which is distinct from the homogenous expression of FR in the healthy and CL kidneys (FIG. 13D, see FIGS. 11A-11E, FIG. 12A-12B, FIG. 22, FIG. 23, FIGS. 21A-21C) for distribution of NPs in other organs). When kidney biopsies obtained from patients with varying degrees of renal fibrosis were examined, we found that fibrotic tubules had a higher expression of FR than their adjacent healthy tissues (FIG. 13E). These results indicate that the differential expression of FR in healthy and fibrotic renal tubules can be exploited for targeted delivery of FA-tagged NPs.

Figure 13F:
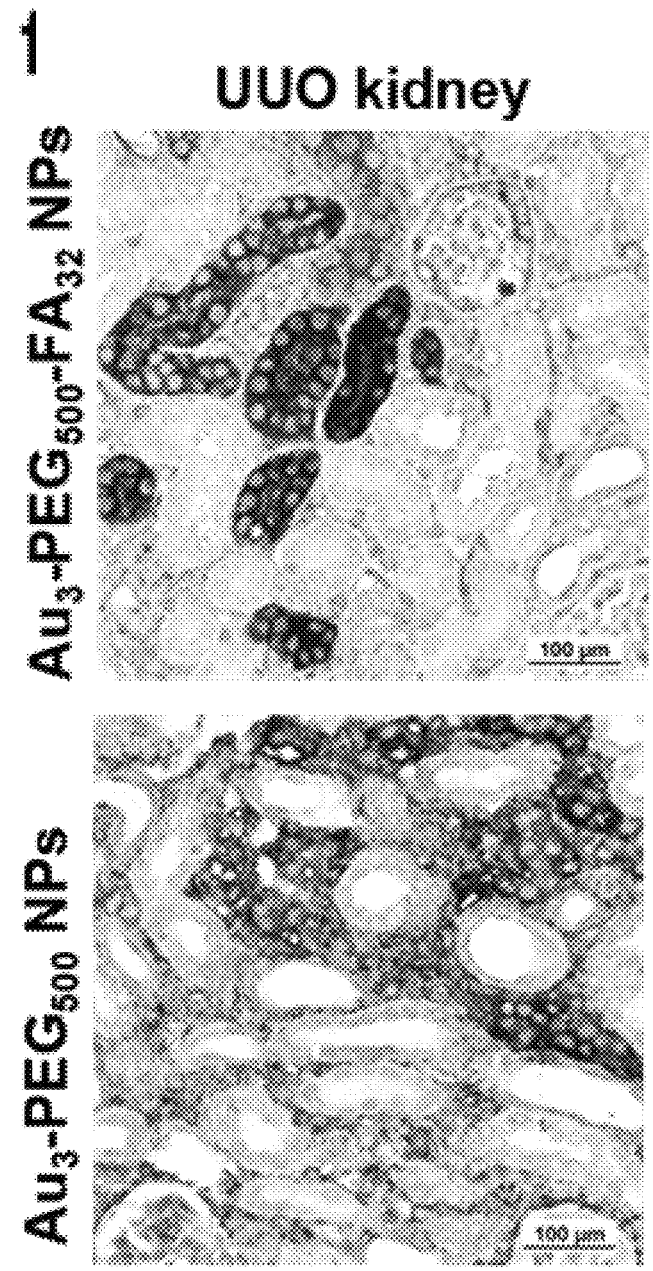
Figure 13G:
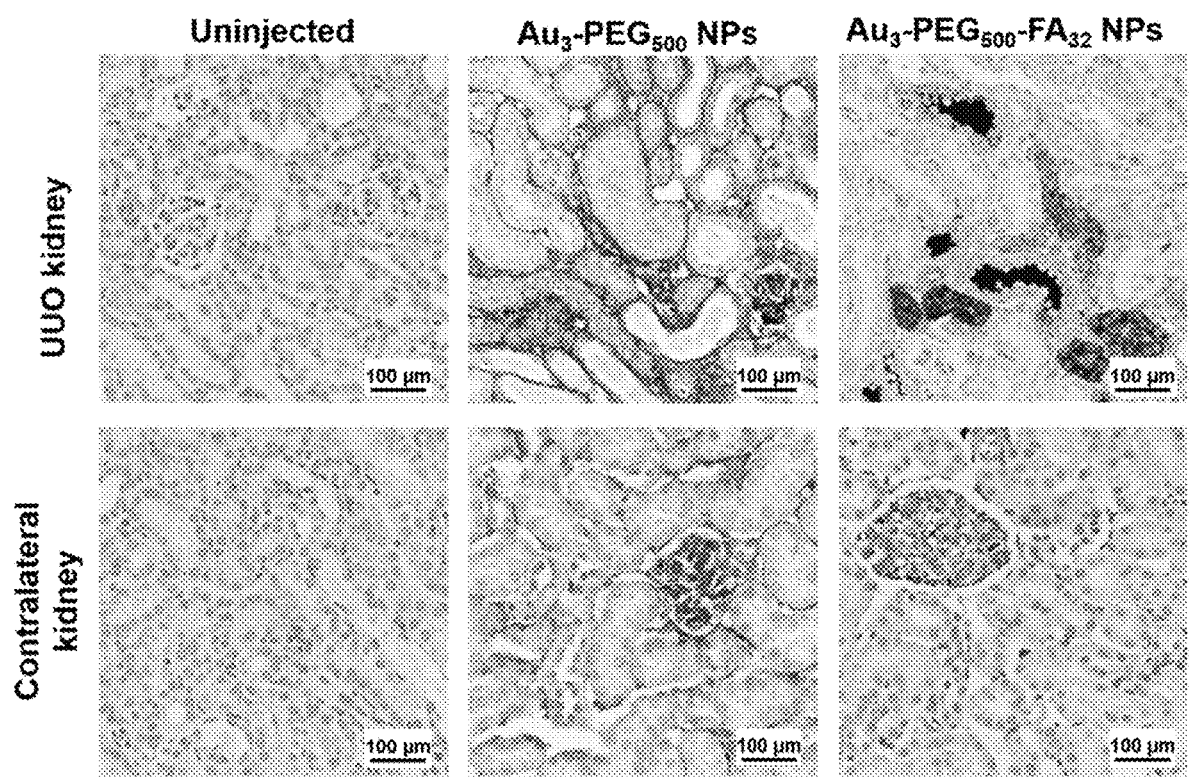
Figure 13H:
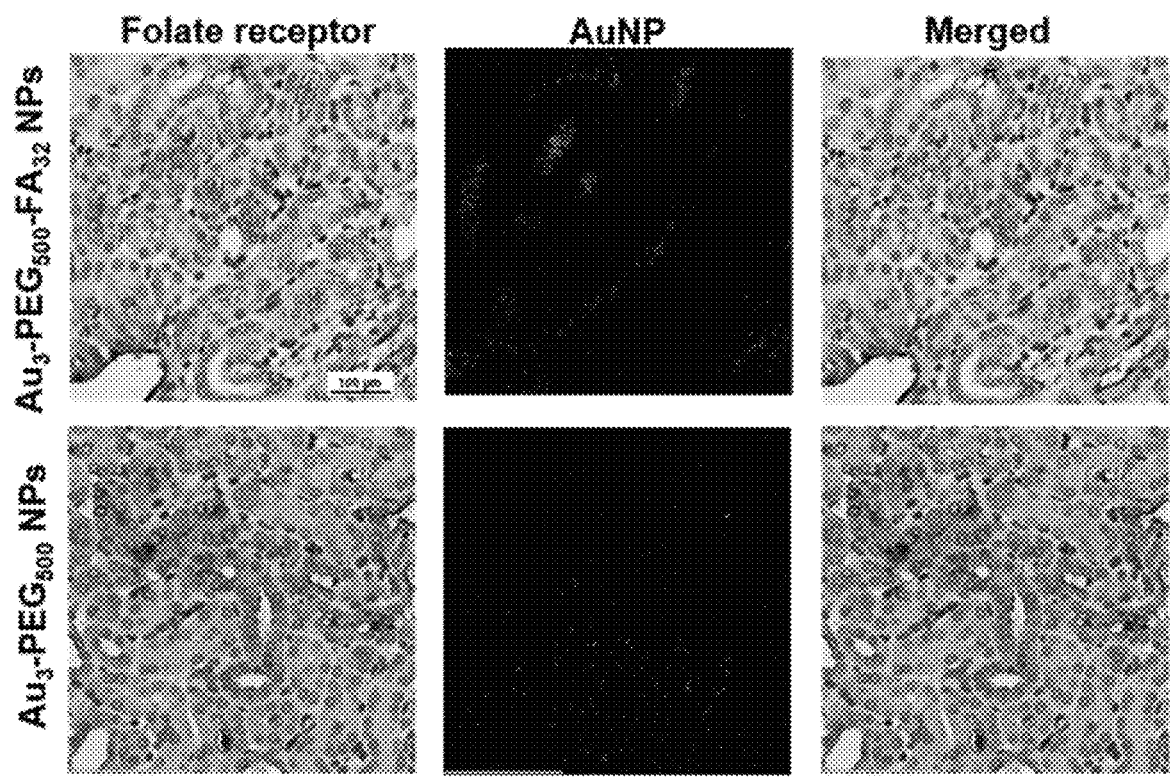

Silver enhancement staining of UUO kidney tissue sections show targeted $Au_3$-$PEG_{500}$-$FA_{32}$ NPs accumulated in some tubule cells while untargeted $Au_3$-$PEG_{500}$ NPs resided outside the tubules (FIG. 13F). Since the pattern of silver-stained NPs in the UUO kidney is consistent with the pattern of elevated local expression of FR in FIG. 13C-D, we investigated whether the elevated expression of FR by some tubules contributes to the increased uptake of $Au_3$-$PEG_{500}$-$FA_{32}$ NPs by the tubules in the UUO kidneys. FR in the UUO kidney section were stained by IHC and the Au cores in the section were imaged by confocal reflectance microscopy. Notably, the Au reflectance signal and FRs on the tubules were localized only for the $Au_3$-$PEG_{500}$-$FA_{32}$ NP sample but not the $Au_3$-$PEG_{500}$ NP sample (FIG. 13H), demonstrating that $Au_3$-$PEG_{500}$-FA NPs bound to FR of the tubules. Transmission electron microscopy (TEM) further confirmed the localization of $Au_3$-$PEG_{500}$-$FA_{32}$ NPs in the cytosol of tubule cells and the presence of both $Au_3$-$PEG_{500}$-$FA_{32}$ and $Au_3$—$PEG_{500}$ NPs in the fibrotic region (FIGS. 17-20). Most of the NPs remained as individual entities without discernible aggregation in the kidney.

Figure 13I:
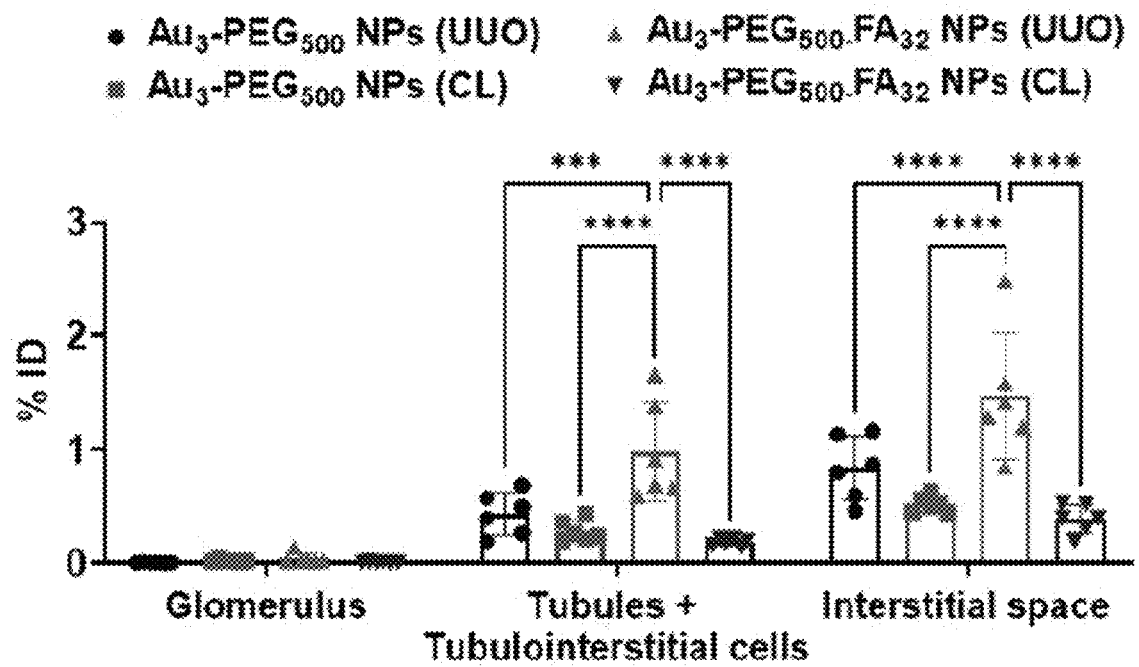
Figure 14:
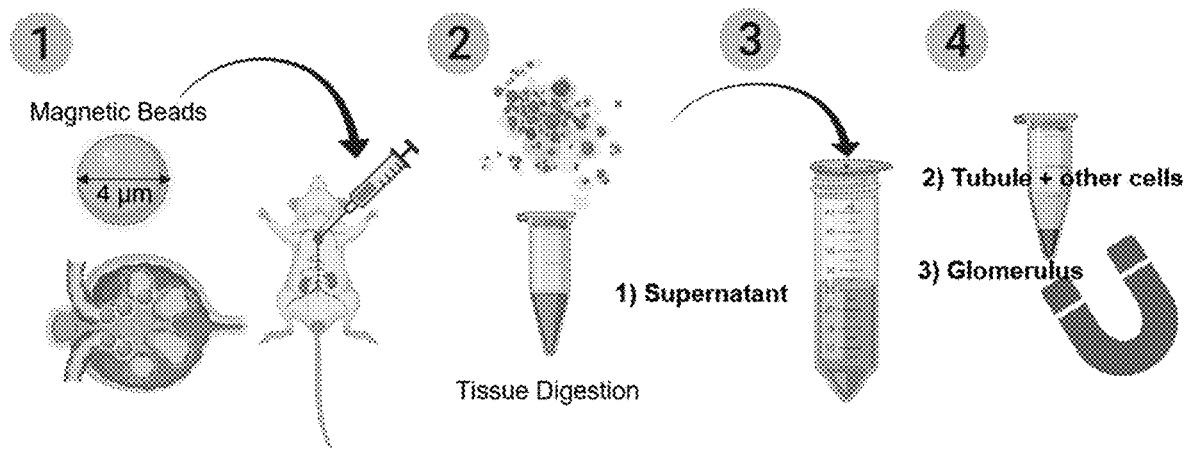
FIG. 14 shows a schematic illustration of the protocol for compartment isolation.
Figure 15A:
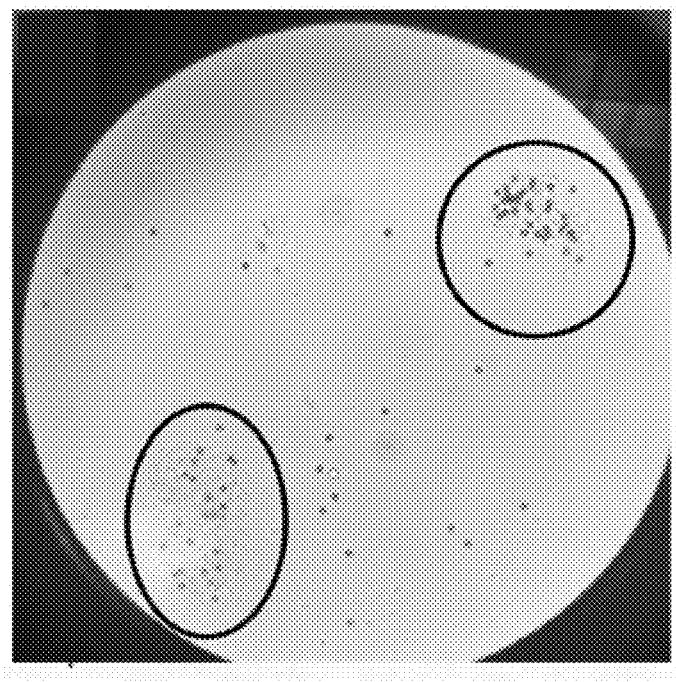
FIG. 15A shows the images of freshly isolated glomerulus prepared using Dynabeads.
Figure 15B:
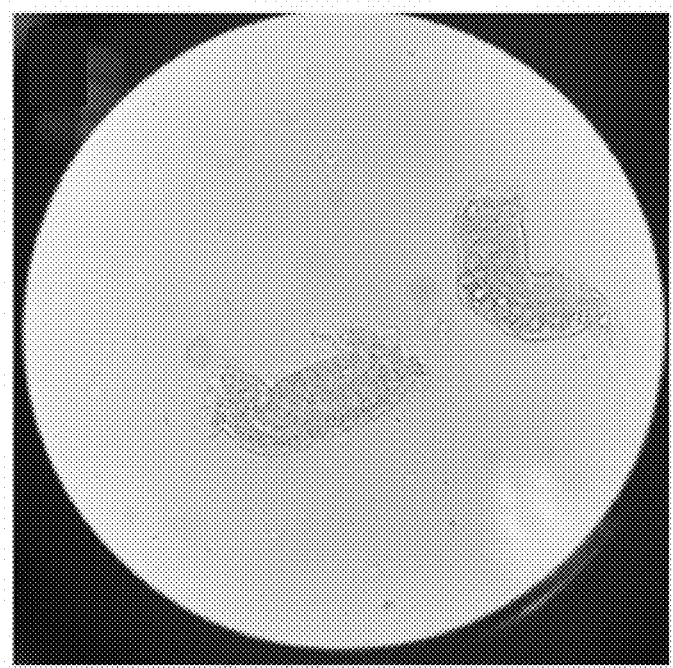
FIG. 15B shows images of freshly isolated tubule segments prepared using Dynabeads.
Figure 15C:
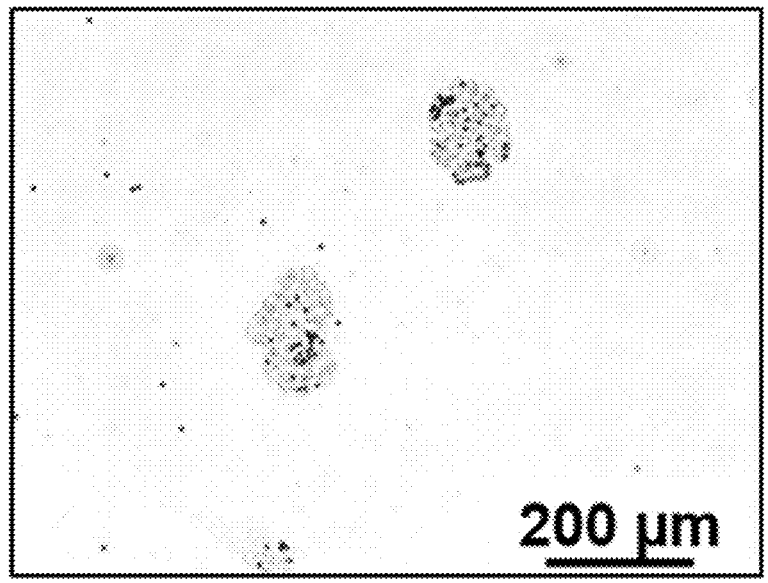
FIG. 15C shows images of formalin-fixed glomeruli.
Figure 15D:
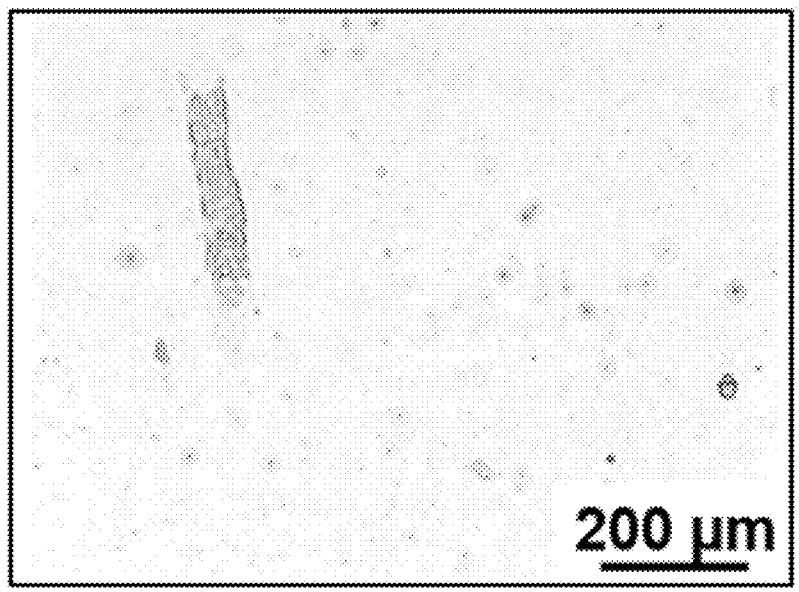
FIG. 15D shows images of formalin-fixed tubule segments.

To quantify the tissue-level distribution of the NPs, we separated the glomeruli, tubules, and tubulointerstitial space from the UUO and CL kidneys (FIGS. 14 and 15A-15D) and measured their respective Au contents using ICP-MS. While significantly more $Au_3$-$PEG_{500}$-$FA_{32}$ NPs accumulated in the tubules and tubulointerstitial cells of the UUO kidney (1.0% ID) than in the CL kidney (0.2% ID), the accumulation of $Au_3$-$PEG_{500}$ NPs in both UUO (0.4% ID) and CL (0.3% ID) kidneys were not significantly different (FIG. 13I). Further, significantly more $Au_3$-$PEG_{500}$-$FA_{32}$ NPs (1.5% ID) than $Au_3$-$PEG_{500}$ NPs (0.8% ID) were detected in the interstitial space of the UUO kidney. Neither untargeted nor targeted NPs accumulated significantly in the glomeruli of UUO and CL kidneys, and accumulation in the CL kidneys is similar for both NP types (FIG. 13I). Together with the silver-staining imaging data, these results demonstrate that targeted $Au_3$-$PEG_{500}$-$FA_{32}$ NPs can be selectively delivered to renal tubules of fibrotic kidneys.

Figure 16:
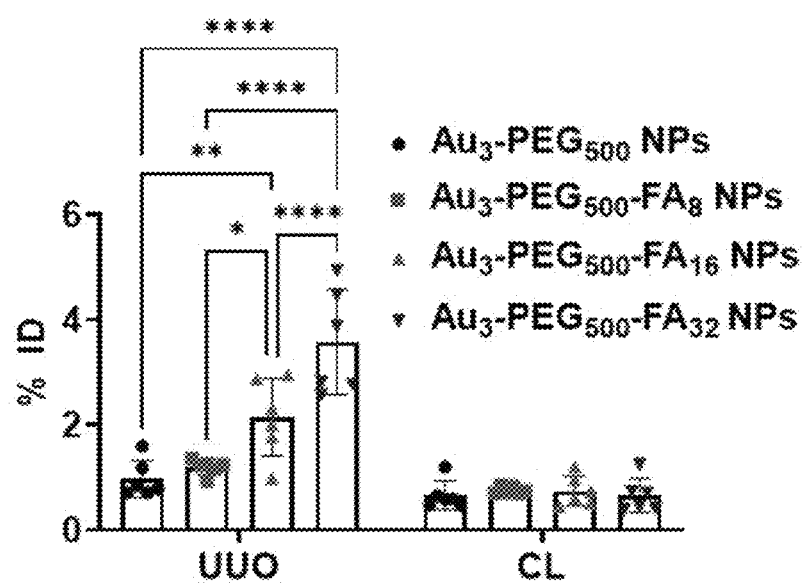
FIG. 16, NP accumulation in UUO kidney increased with higher FA loading (z). Kidneys were harvested 24 h post-injection. Data are from n=3, across 1 experiment. Statistical significance was evaluated using One-Way ANOVA with Tukey's post hoc test for multiple comparison. All p values less than or equal to 0.05 are displayed as * p<0.05,  p<0.01, * p<0.001, ****p<0.0001. P values that are not significant are not displayed. All bars and error bars represent mean±SD.
Figure 17:
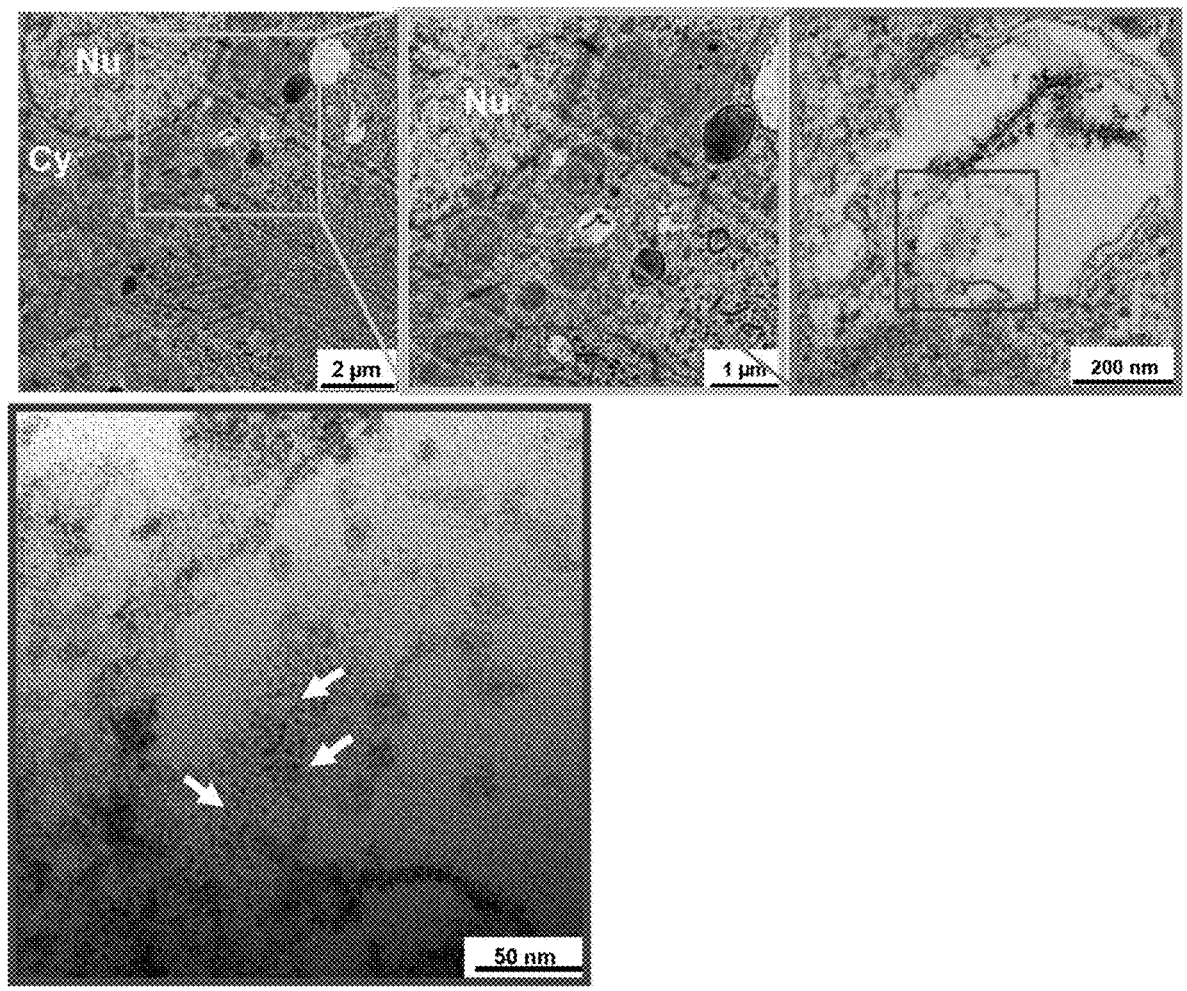
FIG. 17 shows TEM images of Au$_3$-PEG$_{500}$-FA$_{32}$ NPs (white arrows) in the cytosol of tubule cell. Nu=nucleus, Cy=cytosol.
Figure 18:
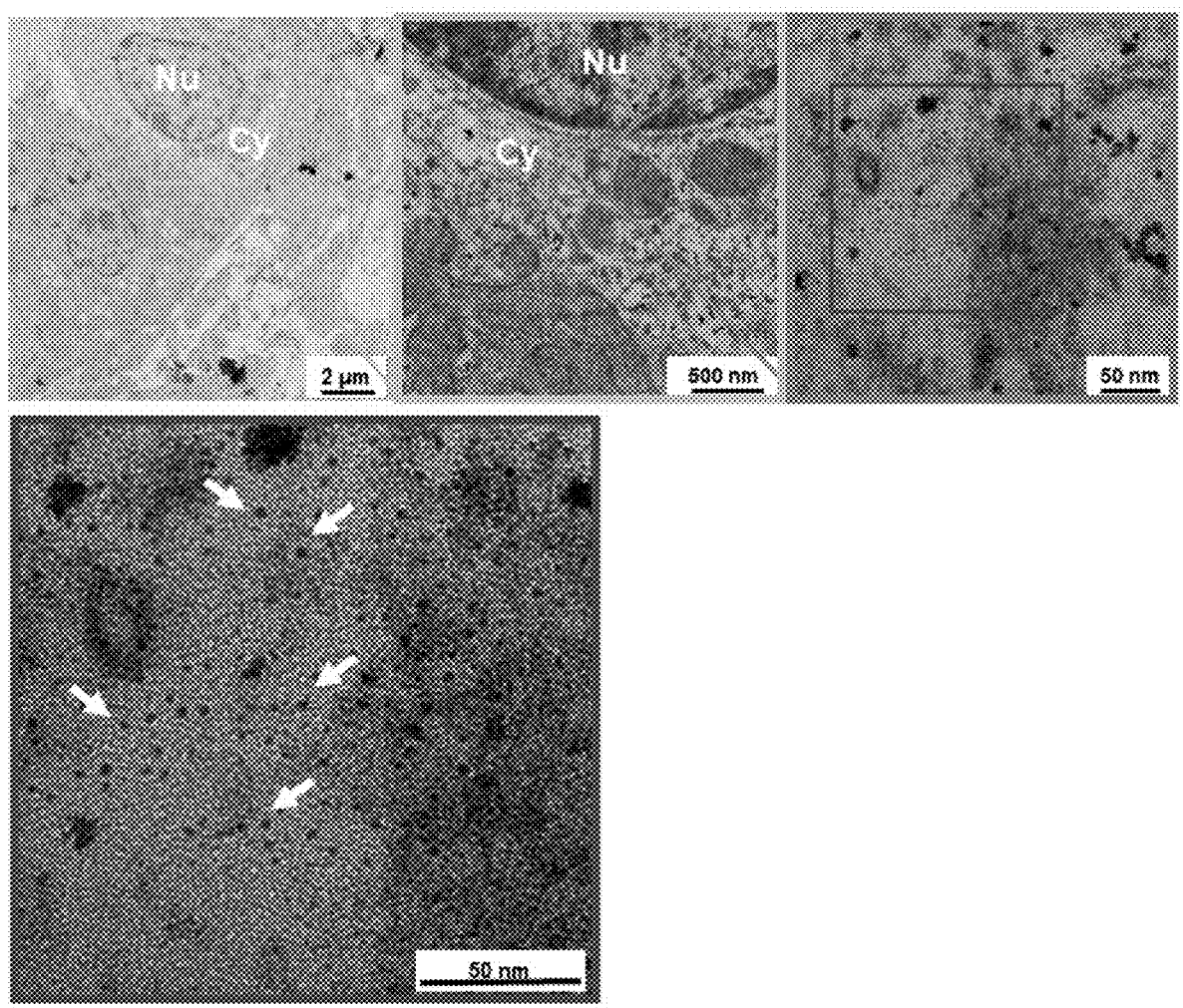
FIG. 18 shows TEM images of Au$_3$-PEG$_{500}$ NPs (white arrows) in the cytosol of tubule cell. Nu=nucleus, Cy=cytosol.
Figure 19:
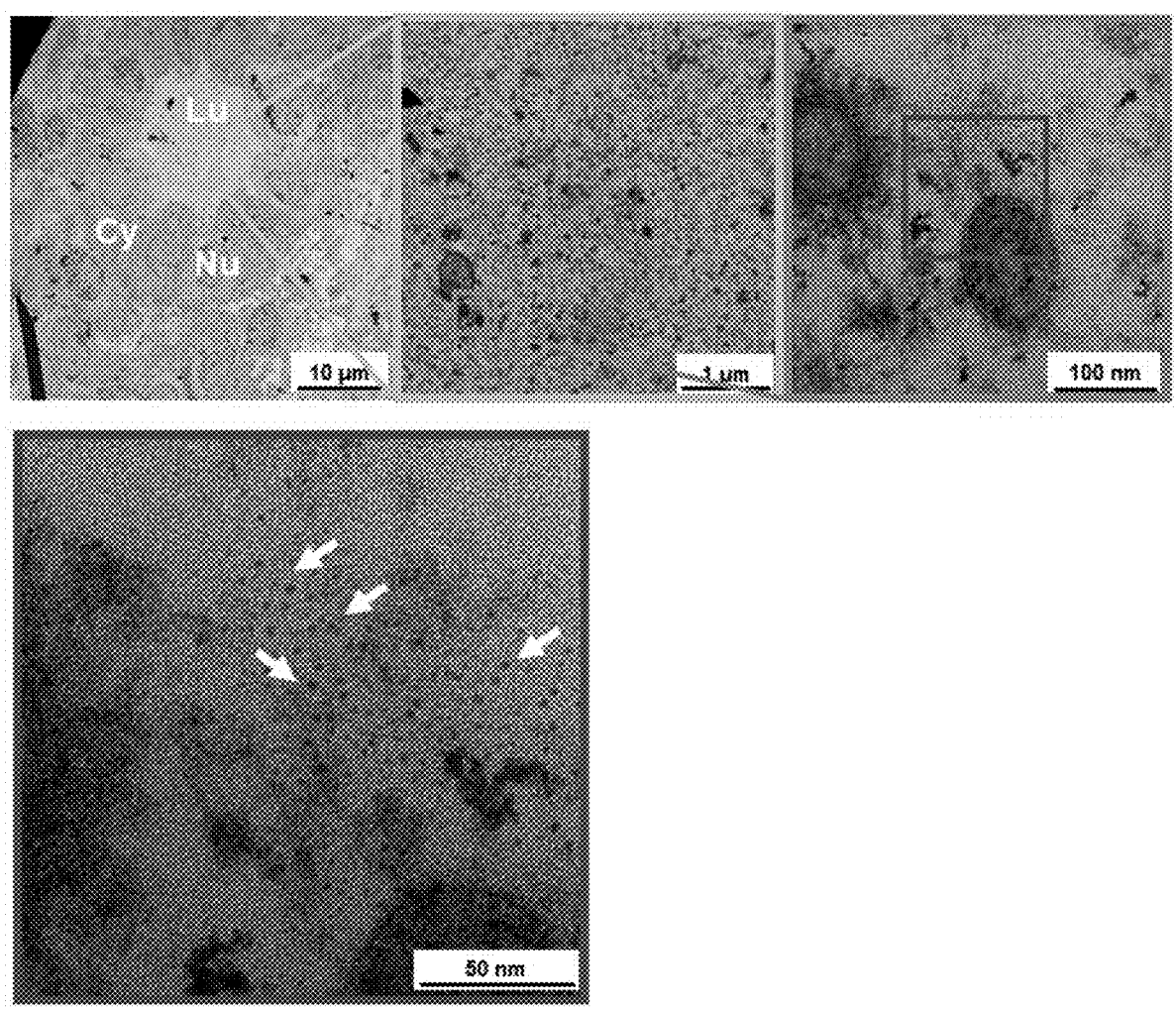
FIG. 19 shows TEM images of Au$_3$-PEG$_{500}$ NPs (white arrows) in the lumen of tubule cells. Nu=nucleus, Cy=cytosol, Lu=tubule lumen.
Figure 20:
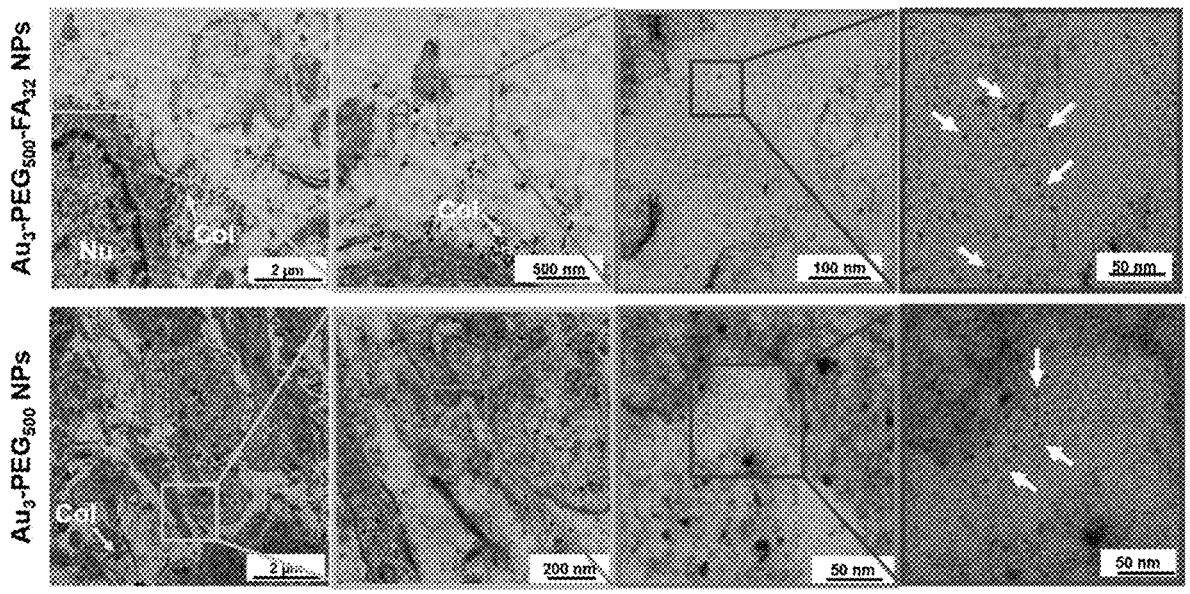
FIG. 20 shows TEM images of AuNPs (white arrows) in the fibrotic area. Nu=nucleus, Col=collagen fiber (yellow arrows).

When different loadings of FA were examined, we found that NP accumulation in the UUO kidney correlated with ligand loading (FIG. 16). The accumulation of $Au_3$-$PEG_{500}$ NPs, $Au_3$—$PEG_{500}$-$FA_8$ NPs, $Au_3$—$PEG_{500}$-$FA_{16}$ NPs, and $Au_3$—$PEG_{500}$-$FA_{32}$ NPs in the UUO kidney were 1.0% ID, 1.2% ID, 2.1% ID, and 3.6% ID, respectively. No such correlation was seen with the CL kidney. Collectively, our data suggest that sub-10 nm and FR-targeting are key design criteria for promoting the delivery of NPs to UUO kidneys.

Example 10—$Au_3$-$PEG_{500}$-$FA_{32}$ NPs Reduce Kidney Degeneration

Figure 24A:
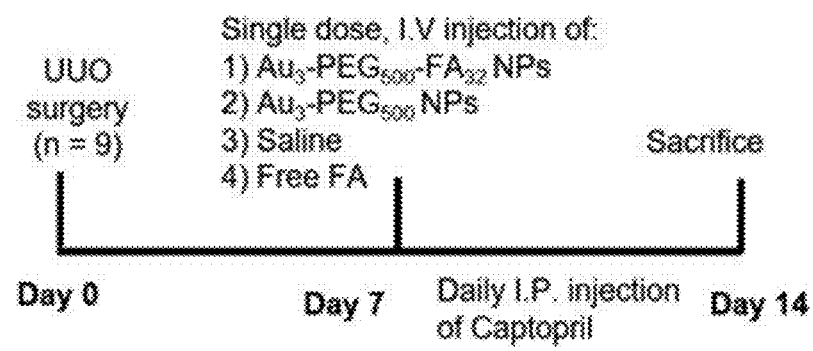
FIGS. 24A-24F Au$_3$-PEG$_{500}$-FA$_{32}$ NPs reduce degeneration of UUO kidney 7 days after treatment.

To investigate whether $Au_3$-$PEG_{500}$-$FA_{32}$ NPs can improve kidney function, we injected a single dose of AuNPs at half of the Au content injected for our biodistribution studies (2.5 mg-Au/kg-mouse) to UUO mice with established renal fibrosis (Day 7 post-UUO surgery). Seven days later (on Day 14 post-UUO surgery) when severe renal fibrosis is expected, the animals were sacrificed, and the organs and tissues were examined (FIGS. 5A-5C). Controls included untargeted $Au_3$-$PEG_{500}$ NPs (2.5 mg-Au/kg-mouse), free FA (0.12 mg-FA/kg-mouse; same FA dosage as $Au_3$-$PEG_{500}$-$FA_{32}$ NPs), saline and Captopril (5 mg-drug/kg-mouse/day)[46], an ACE inhibitor used as a standard drug for treating CKD (FIG. 24A).

Figure 24B:
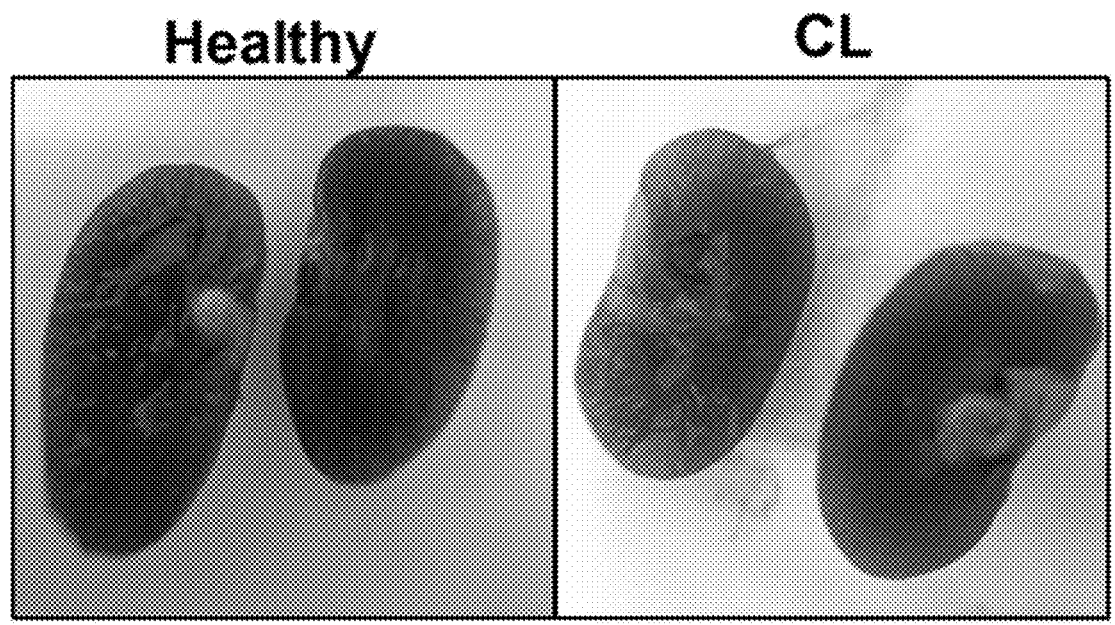
Figure 24C:
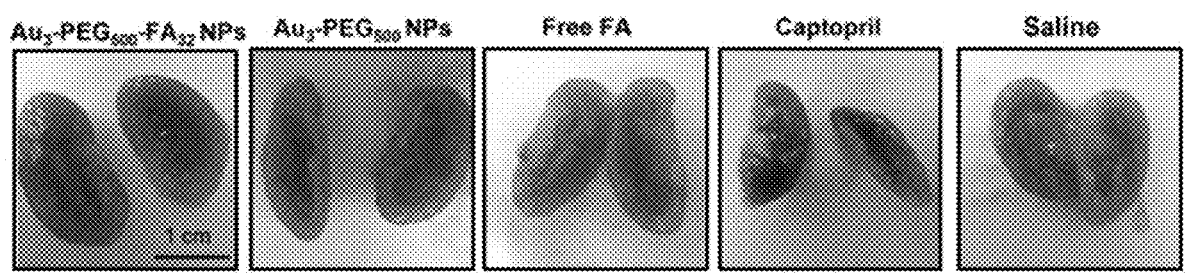
Figure 24D:
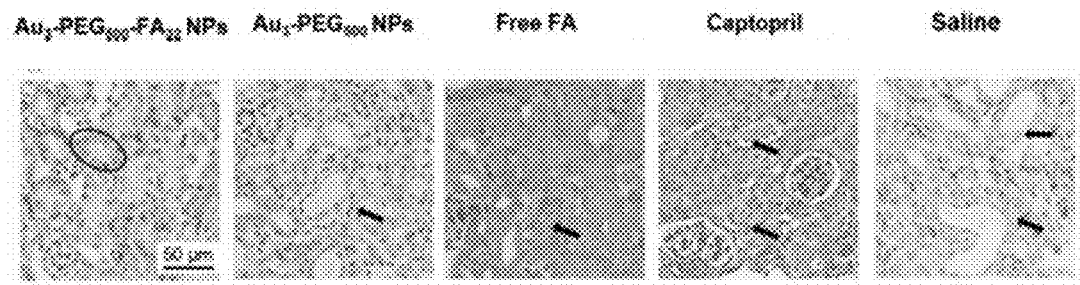
Figure 24E:
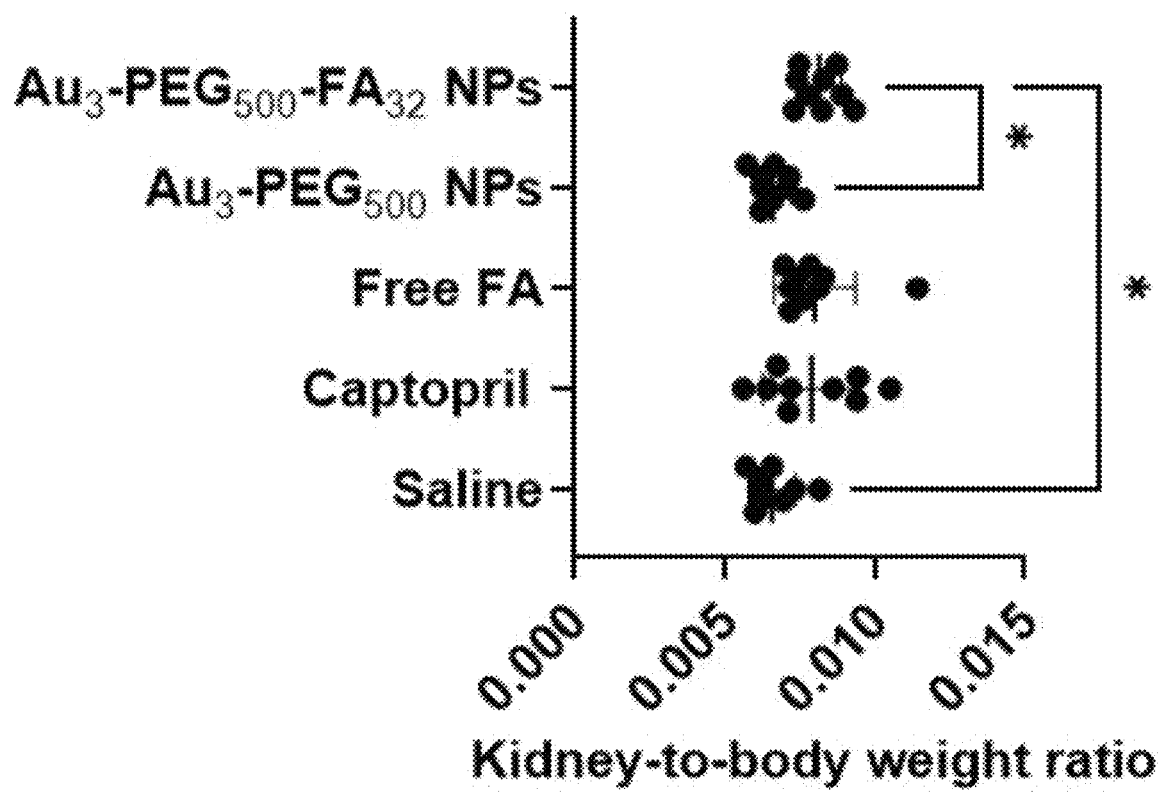
Figure 24F:
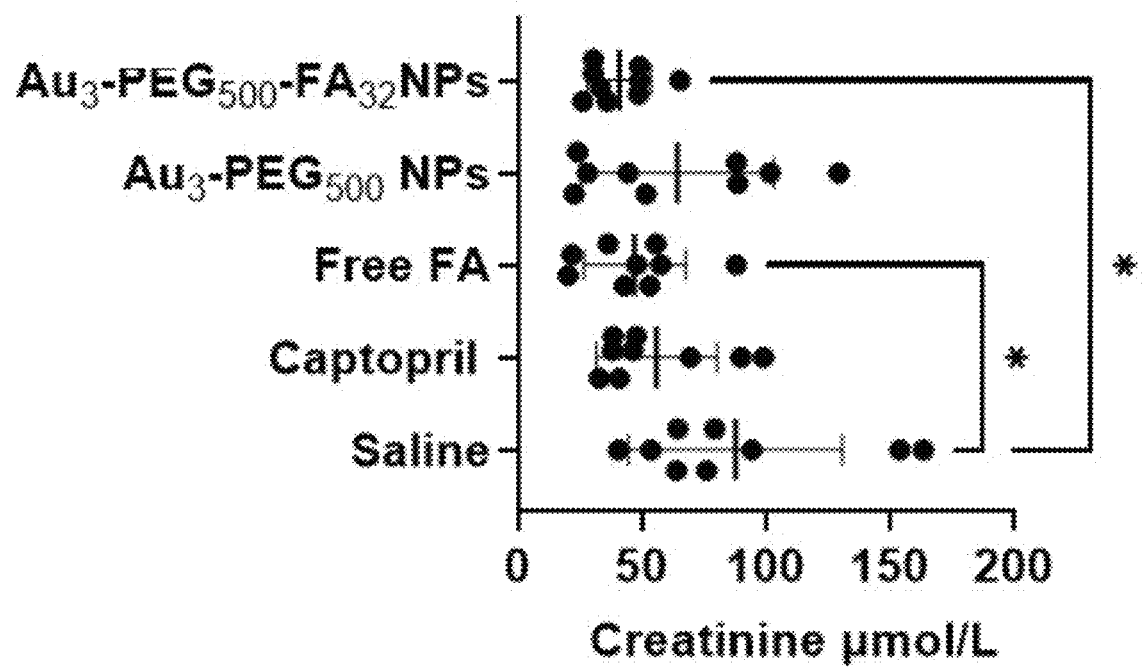

Gross comparison of kidneys from healthy mice and CL kidneys from UUO mice (FIG. 24B) with UUO kidneys show both $Au_3$-$PEG_{500}$-$FA_{32}$ NP and free FA rescued the UUO kidney from tissue degeneration but $Au_3$-$PEG_{500}$ NP, Captopril or saline treatments did not (FIG. 24C). Histological images reveal that animals treated with $Au_3$-$PEG_{500}$-$FA_{32}$ NPs had more intact tubule segments and fewer degenerating tubules in the UUO kidneys than other treatment groups (FIG. 24D). Tissue degeneration was further quantified by measuring the kidney weight of each mouse and normalizing them to the body weight at sacrifice (n=9; FIG. 24E). Mice treated with $Au_3$-$PEG_{500}$-$FA_{32}$ NPs had significantly higher kidney-to-body weight ratio than those treated with saline and $Au_3$—$PEG_{500}$ NPs, suggesting that $Au_3$-$PEG_{500}$-$FA_{32}$ NP treatment could prevent tissue loss arising from CKD. However, we cannot exclude the contribution of edema to the increased kidney weight. Further, compared to the saline-treated group (equivalent to untreated), animals treated with $Au_3$-$PEG_{500}$-$FA_{32}$ NPs and free FA showed significant improvement in the renal clearance of creatinine, a metabolic waste in the blood normally filtered by healthy kidneys (FIG. 24F). Note that the creatinine levels of all groups still fall within the normal level ranger as UUO mice still have one functioning kidney (the CL kidney). Our results demonstrate that $Au_3$-$PEG_{500}$-$FA_{32}$ NPs can effectively reduce tissue degeneration in UUO kidneys.

TABLE 3

Endotoxin level of $Au_3$—$PEG_{500}$ NPs and of $Au_3$—$PEG_{500}$—$FA_{32}$ NPs

| Sample | $Au_3$—$PEG_{500}$ NPs | $Au_3$—$PEG_{500}$—$FA_{32}$ NPs |
|---|---|---|
| Endotoxin level (EU/mL) | 0.01 ± 0.002 | 0.003 ± 0.001 |

All reported data represent mean±1 SD from four biological replicates.

Example 11—$Au_3$-$PEG_{500}$-$FA_{32}$ NPs Treatment Reduces Renal Fibrosis

We further evaluated whether $Au_3$-$PEG_{500}$-$FA_{32}$ NPs can treat renal fibrosis. The primary treatment outcome is the level of type I collagen, the main component of fibrous scar[15]. IHC analysis show that UUO kidneys of mice injected with $Au_3$-$PEG_{500}$-$FA_{32}$ NPs had a significantly lower (5.0%) fractional area of type I collagen than those injected with saline (13.1%; p=0.002) (FIGS. 4A-4B). Importantly, $Au_3$—$PEG_{500}$-$FA_{32}$ NP led to a more significant areal reduction in type I collagen than free FA (p=0.0233). By contrast, the reduction in type I collagen for the $Au_3$-$PEG_{500}$ NP (11.7%), Captopril (13.5%), and free FA (11.2%) treatment groups was not significantly different from the saline group.

Figure 25A:
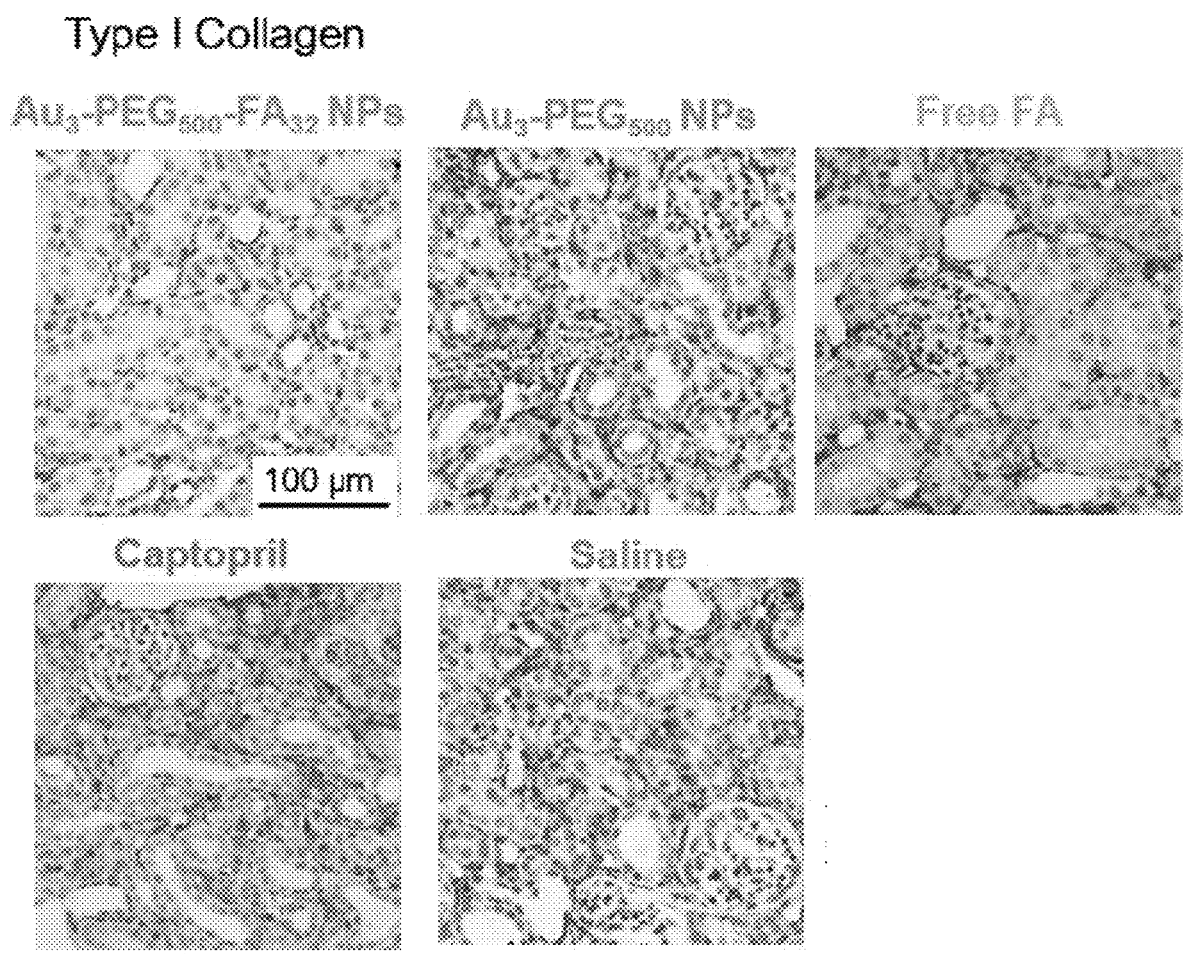
FIGS. 25A-25F Au$_3$-PEG$_{500}$-FA$_{32}$ NPs reduce fibrosis in UUO kidney 7 days after treatment. Representative IHC images and graphs showing the expression of fibrosis markers, interstitial type I collagen (brown) (FIGS. 25A-25B), α-SMA (brown) (FIGS. 25C-25D) and CD3+ cells (brown and black arrows) (FIGS. 25D-25F) in various treatment groups. Representative images from n=2 kidney sections from 9 mice/group. Data are from n=9, across 3 independent experiments. Statistical significance was evaluated using One-Way ANOVA with Tukey's post hoc test for multiple comparison. All p values less than or equal to 0.05 are displayed as * p<0.05,  p<0.01, * p<0.001, ****p<0.0001. P values that are not significant are not displayed. All bars and error bars represent mean±SD.
Figure 25B:
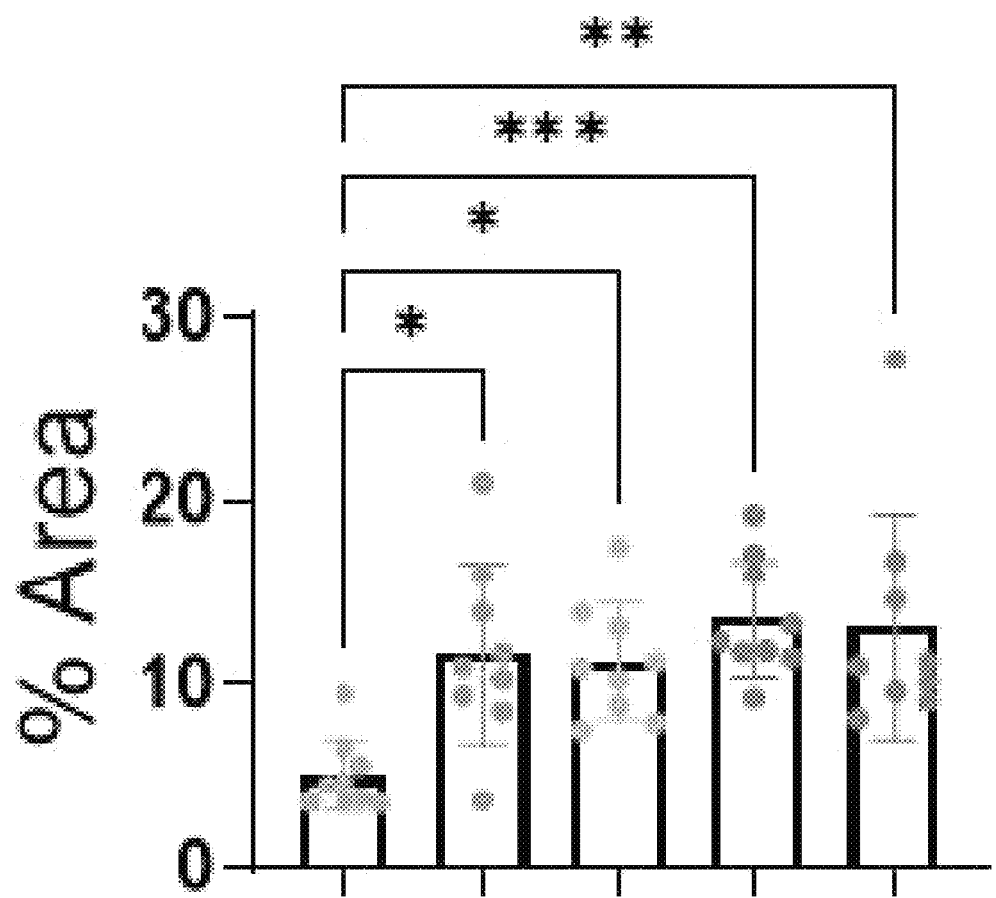
Figure 25C:
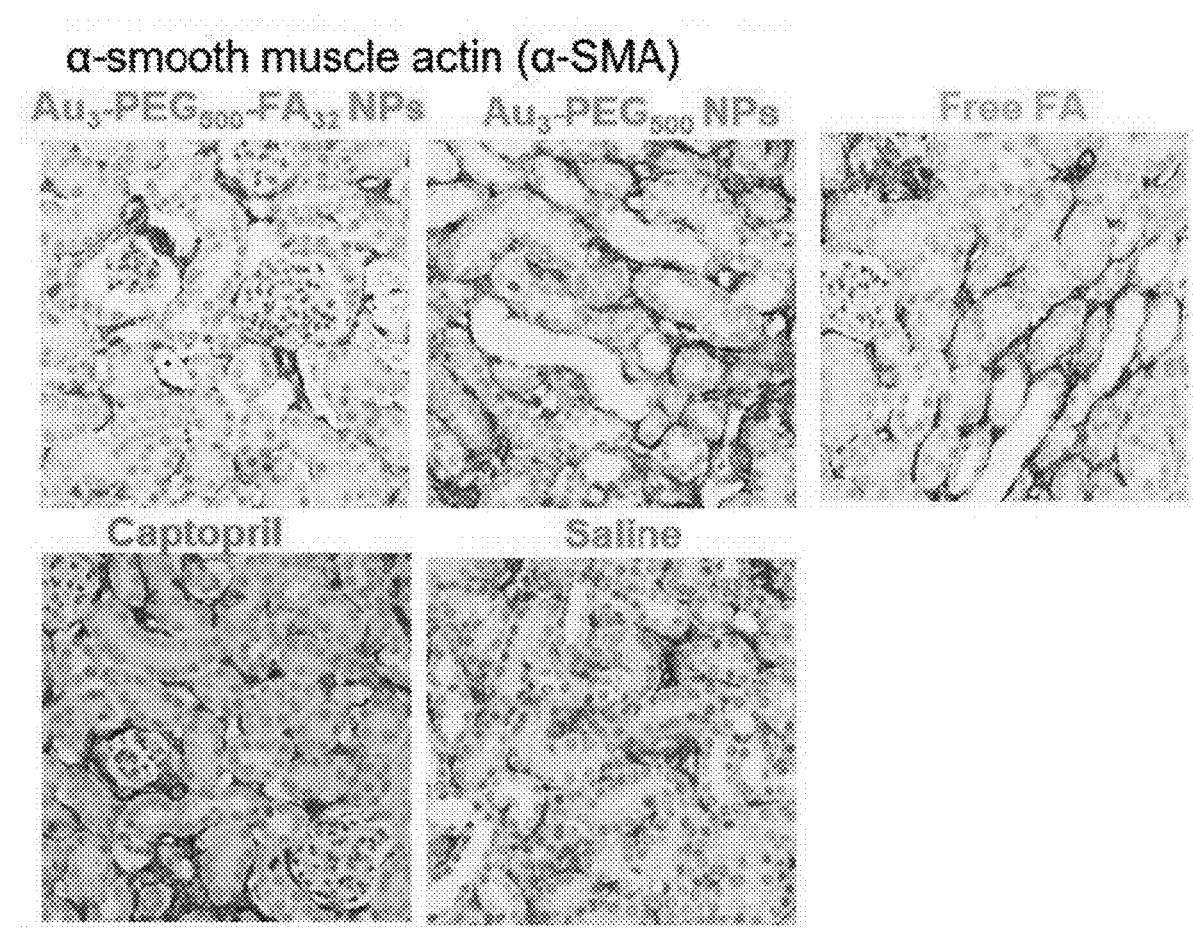
Figure 25D:
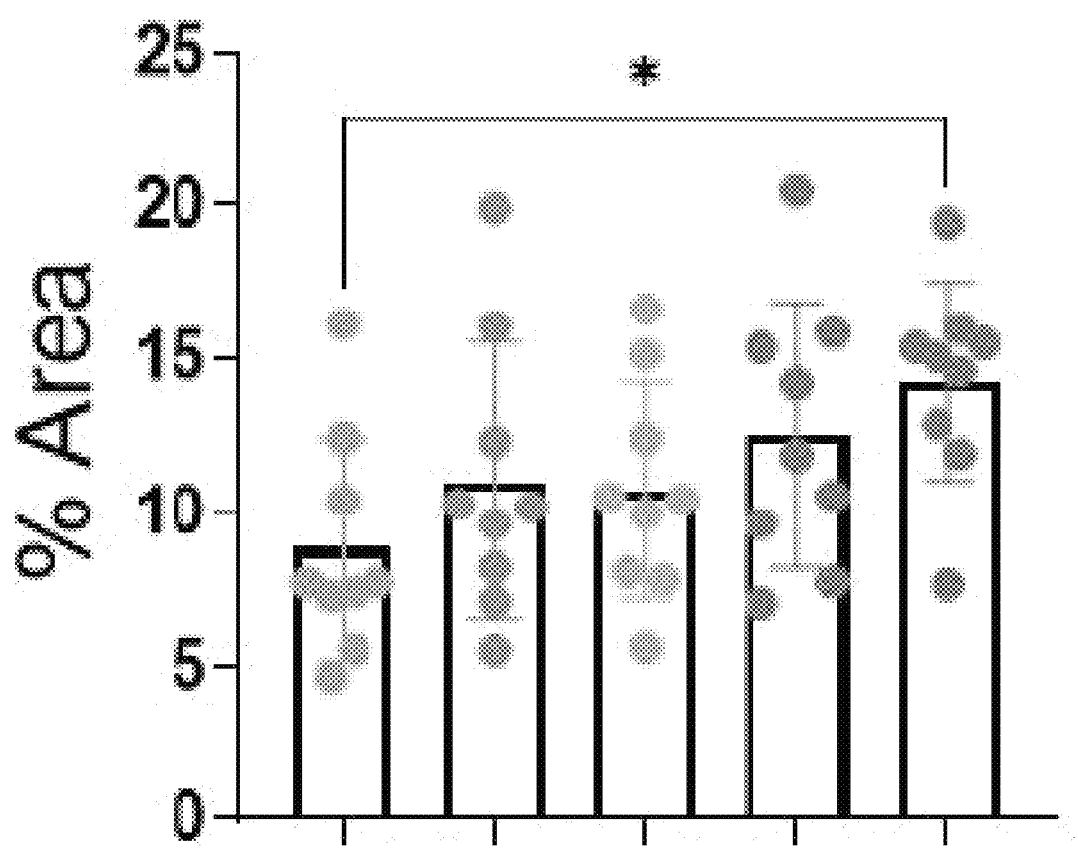
Figure 25E:
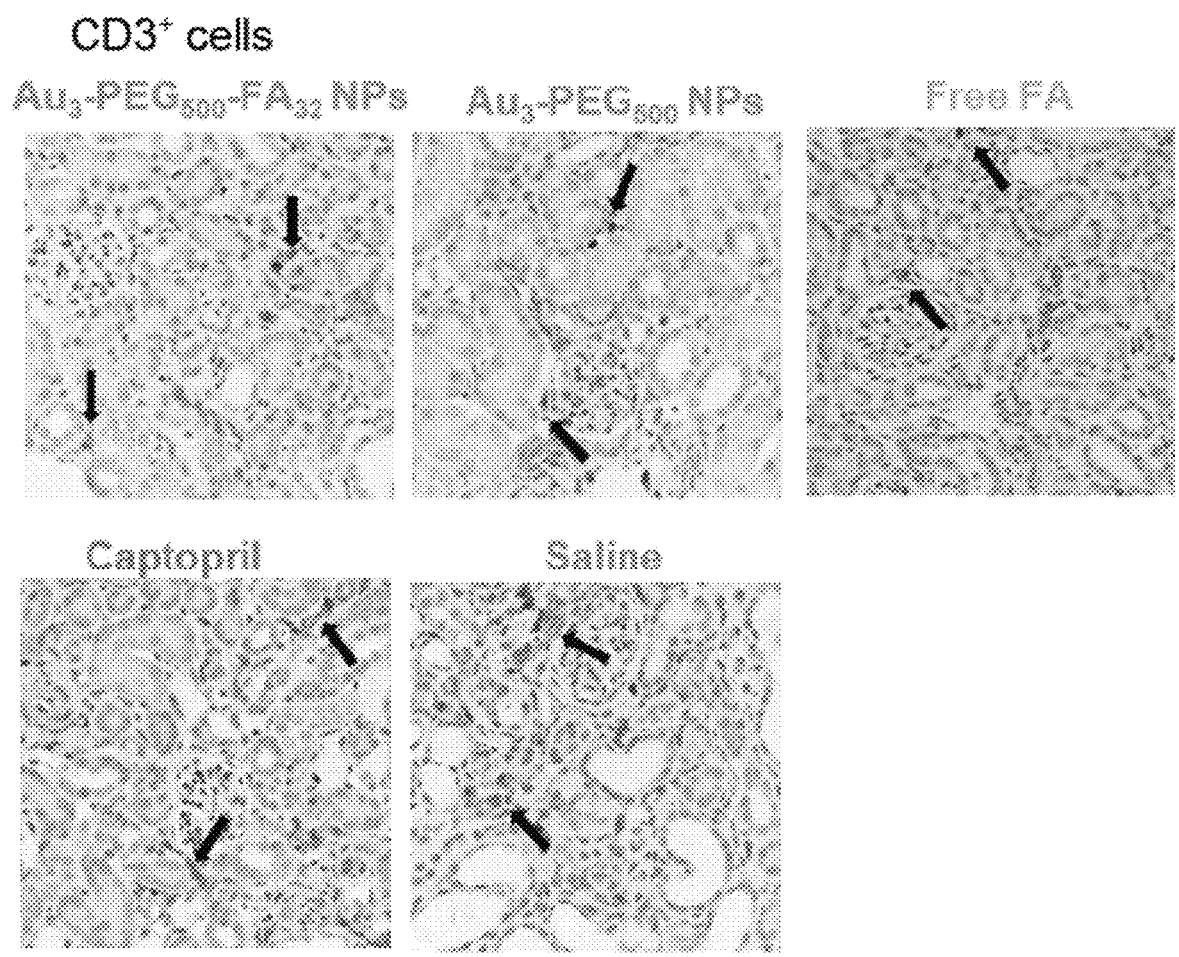
Figure 25F:
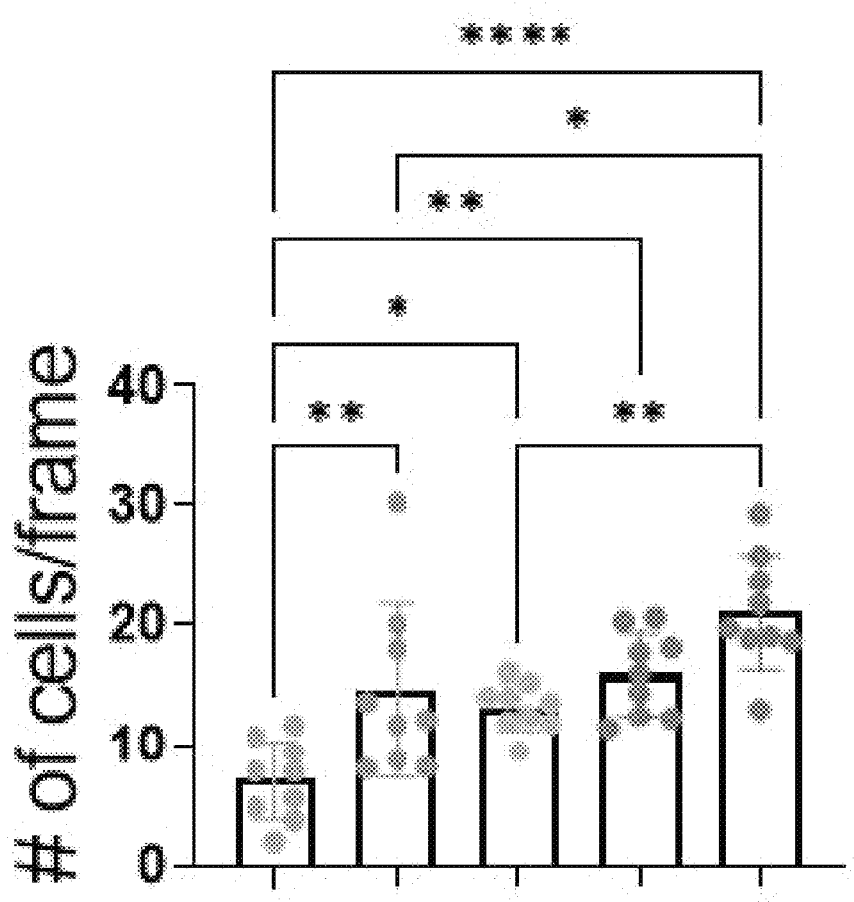

Besides type I collagen, we also stained the tissues for α-smooth muscle actin (a-SMA) and CD3+ T cell infiltration. α-SMA+ cells, such as myofibroblasts, are the primary source of ECM in fibrotic kidneys[17] and T cells is a pathological feature of renal fibrosis[2]. The area with positive α-SMA in the UUO kidney of animals treated with $Au_3$-$PEG_{500}$-$FA_{32}$ NPs (8.8%) was 38% lower when compared with animals treated with saline (14.3%) (p=0.037; FIGS. 25C-25D). No significant differences in the a-SMA area were seen between animals treated with saline, $Au_3$—$PEG_{500}$ NPs (11.0%), Captopril (12.5%), and free FA (10.7%). Meanwhile, of all the treatment groups, the $Au_3$-$PEG_{500}$-$FA_{32}$ NP group showed the lowest mean population of CD3+ T cells (7 cells/frame) (FIGS. 25E-25F). Besides the $Au_3$-$PEG_{500}$-$FA_{32}$ NP and free FA groups, none of the other treatment groups were significantly different from the saline group (21 cells/frame). Notably, $Au_3$—$PEG_{500}$-$FA_{32}$ NP treatment led to a more significant reduction in CD3+ T cell population than free FA (13 cells/frame; p=0.047). Collectively, our data indicate that a single injection of $Au_3$-$PEG_{500}$-$FA_{32}$ NPs can treat renal fibrosis more effectively than the current daily injections of ACE inhibitor.

Example 12—$Au_3$-$PEG_{500}$-$FA_{32}$ NPs Downregulate ECM-Related Genes

Figure 27A:
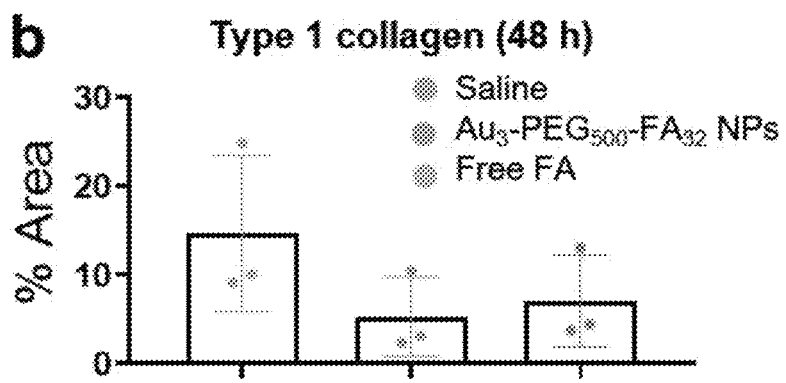
FIGS. 27A-27C Au$_3$-PEG$_{500}$-FA$_{32}$ NPs downregulate ECM-related genes after 2 days of treatment.
Figure 35:
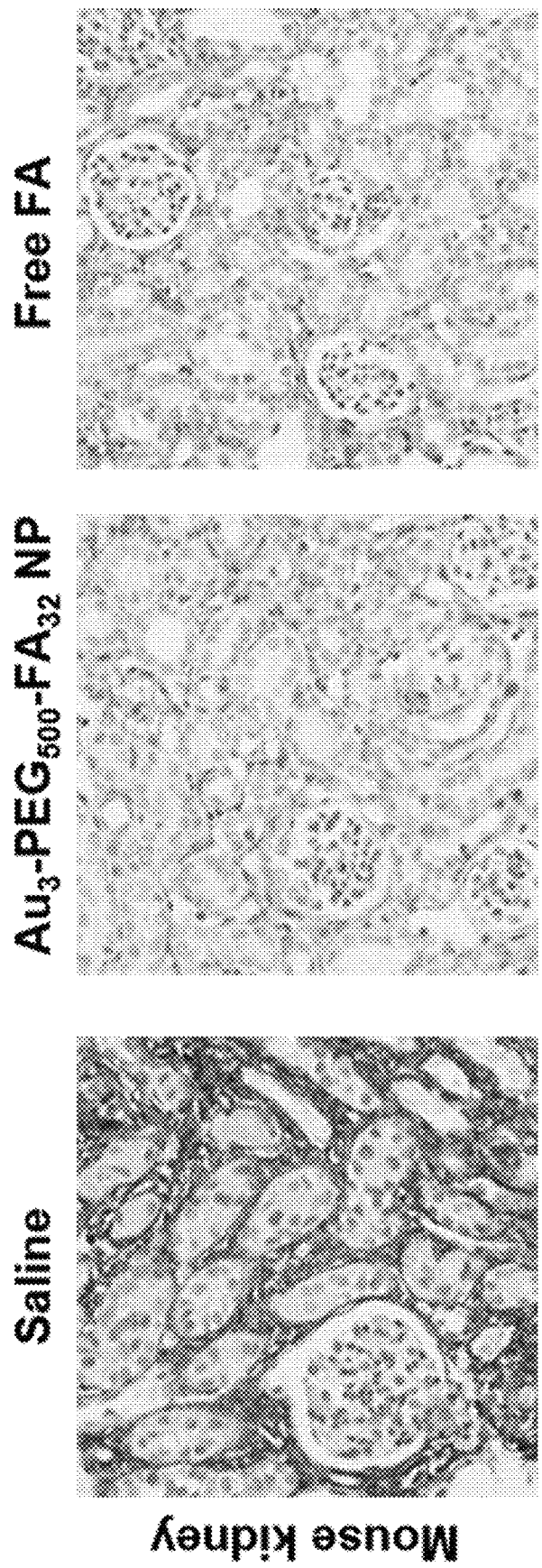
FIG. 35 IHC staining of type I collagen in UUO kidneys used for RNA-seq of saline, Au$_3$-PEG$_{500}$-FA$_{32}$ NP, and Free FA treated mouse kidney. These raw IHC images form the basis of the area calculation listed in FIG. 27A of the main text. Representative images from n=2 kidney sections from 3 mice/group.

To gain insights into the efficacy of $Au_3$-$PEG_{500}$-$FA_{32}$ NPs, we performed RNA sequencing (RNA-seq) analysis to compare the changes in gene expression 48 h post-injection of $Au_3$-$PEG_{500}$-$FA_{32}$ NPs, free FA, or saline to UUO mice at the same dosage used for the efficacy studies above (FIGS. 31A-31C, 32A-32C, 33A-33C, 34A-34C). We chose the 48 h time point to avoid the potential degradation or translation of mRNA. Notably, the type I collagen (gene ID: Col1a1) transcript was significantly downregulated in the $Au_3$-$PEG_{500}$-$FA_{32}$ NP group when compared to the saline group (log 2 fold change=−0.99, Q value=0.0074) (Tables 4-5). Further, IHC staining of the UUO kidneys showed $Au_3$-$PEG_{500}$-$FA_{32}$ NP and free FA treatment groups had lower type I collagen protein expression than the saline group 48 h post-injection (FIG. 27A and FIG. 35), validating our RNA-seq data. The statistically insignificant difference in protein expression of type I collagen between the $Au_3$-$PEG_{500}$-$FA_{32}$ NP and free FA groups at 48 h post-injection is reasonable because changes in gene expression occur faster at the mRNA level than at the protein level. Significant downregulation of type I collagen at the protein level took 7 days as shown in FIG. 25A.

Figure 27B:
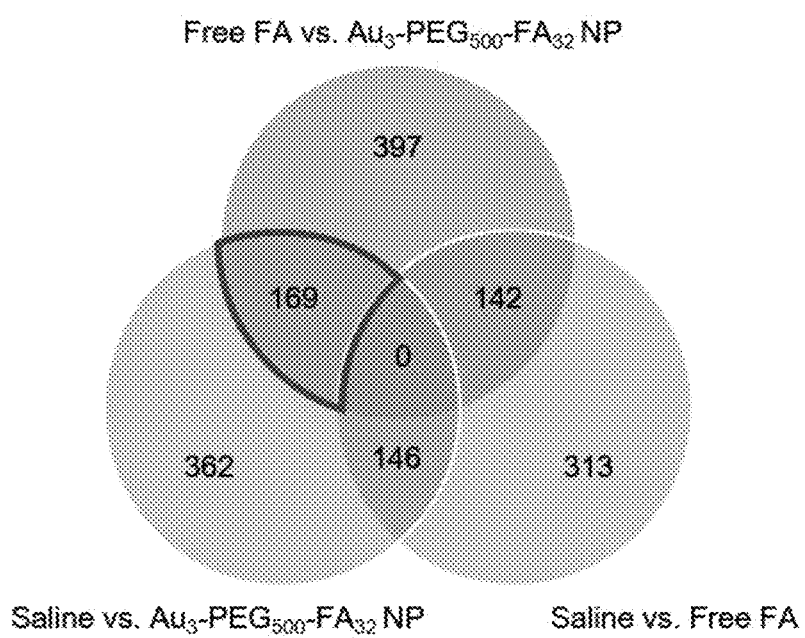
Figure 27C:
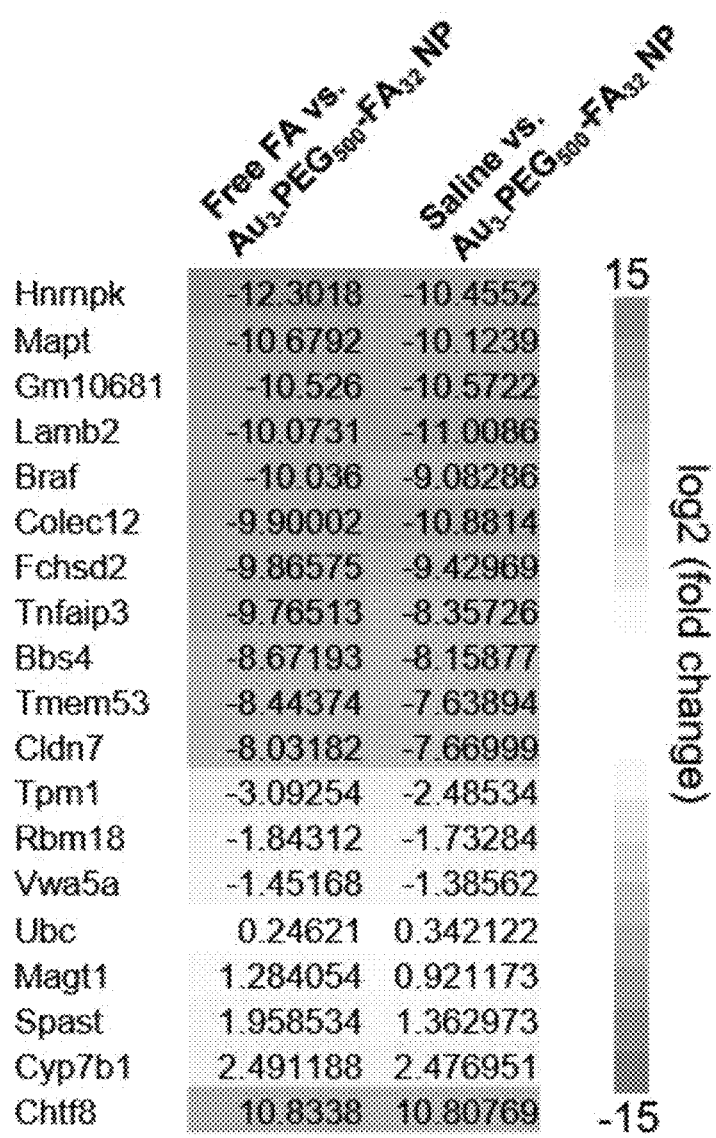
Figure 28A:
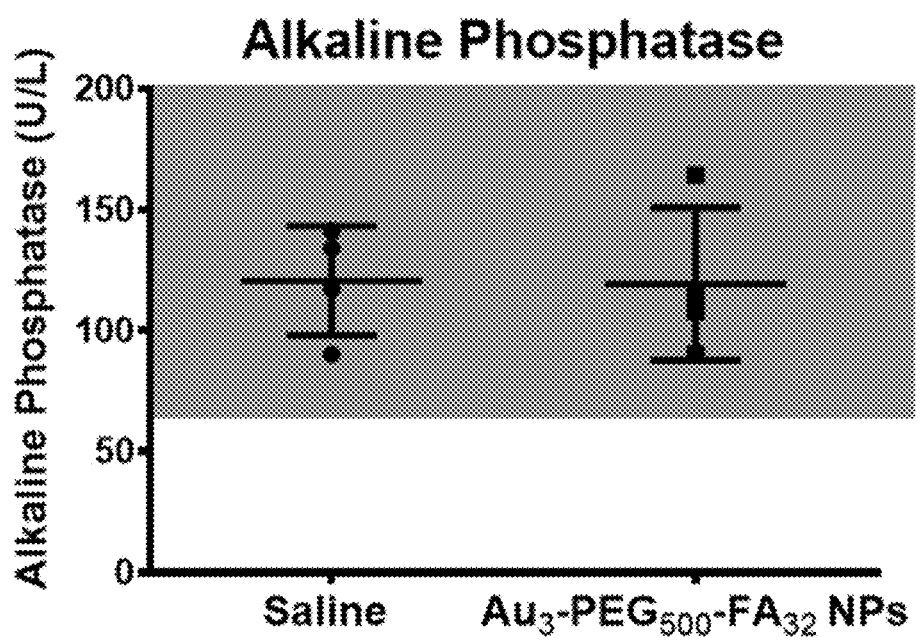
FIGS. 28A-28E Hepatotoxicity analysis of UUO mice 7 days after i.v. injection of AU$_3$-PEG$_{500}$-FA$_{32}$NPs and saline (n=4 mice/group) (or Day 14 after UUO surgery). The serum markers include alkaline phosphatase (ALP) (FIG. 28A), total bilirubin (FIG. 28B), aspartate aminotransferase (AST) (FIG. 28C), alanine transaminase (ALT) (FIG. 28D) and total protein (FIG. 28E). Grey shaded area represents normal range for mice. Error bar denotes ±1 SD. Data are from n=4, across 1 experiment.
Figure 28B:
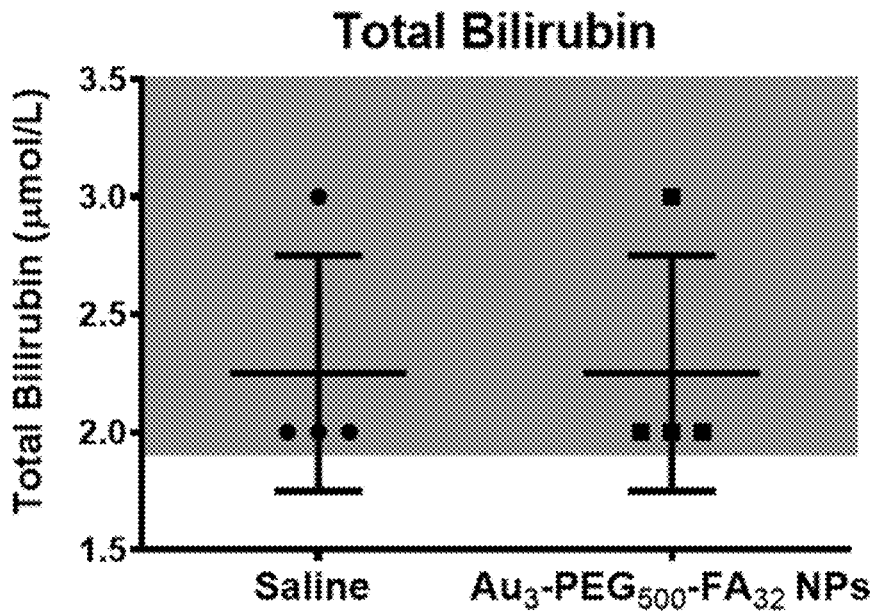
Figure 28C:
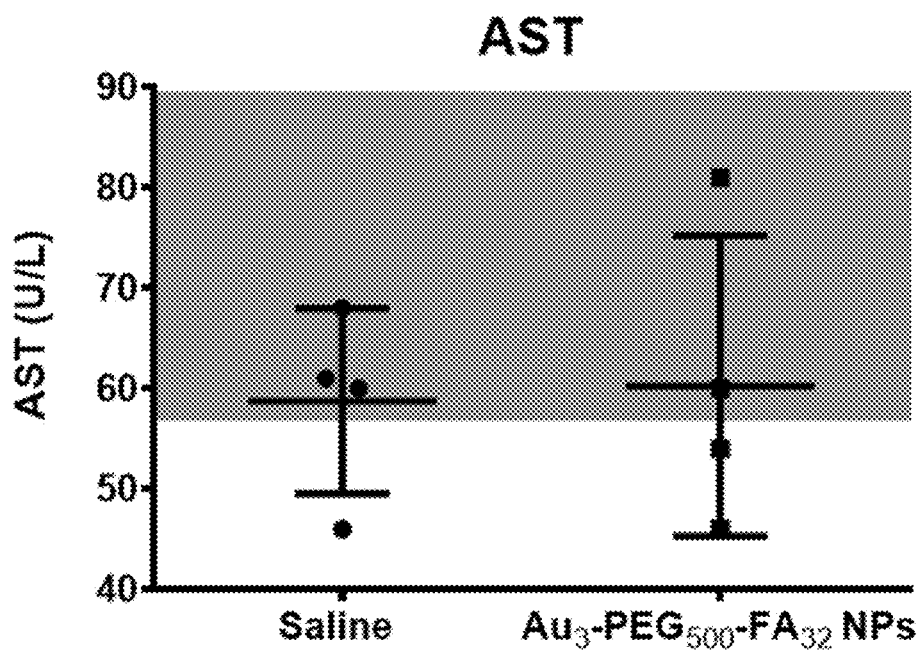
Figure 28D:
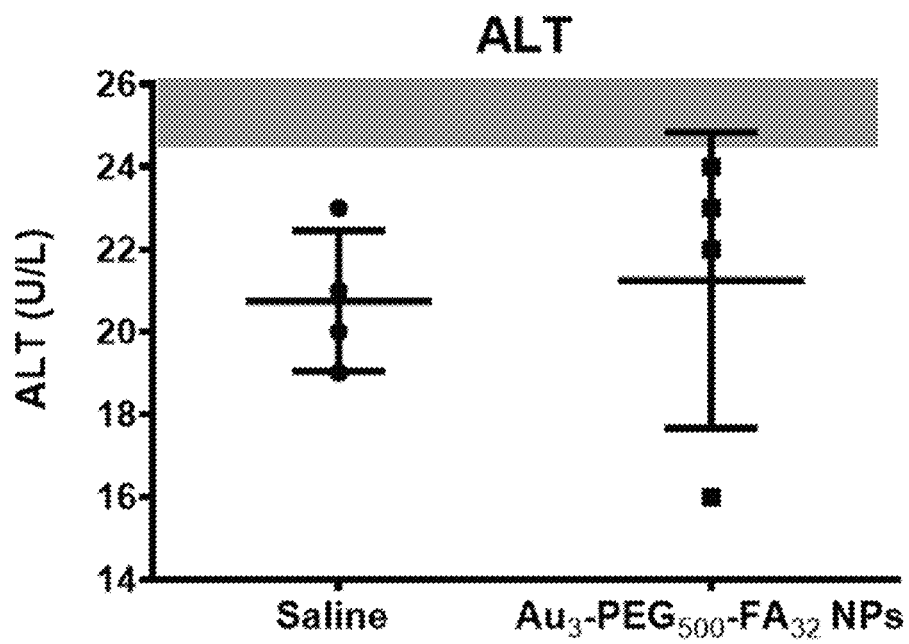
Figure 28E:
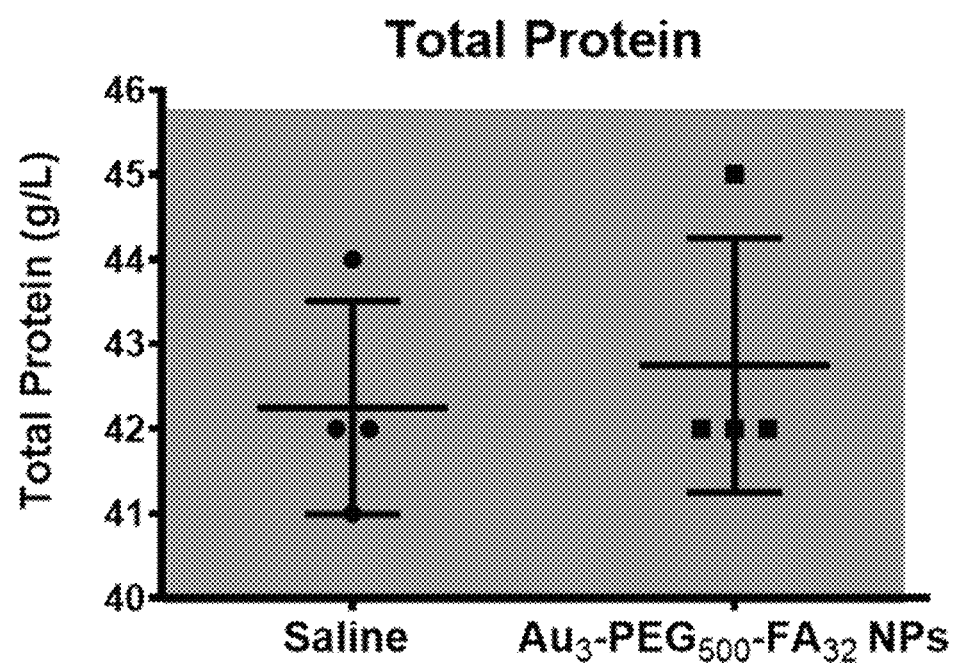
Figure 29A:
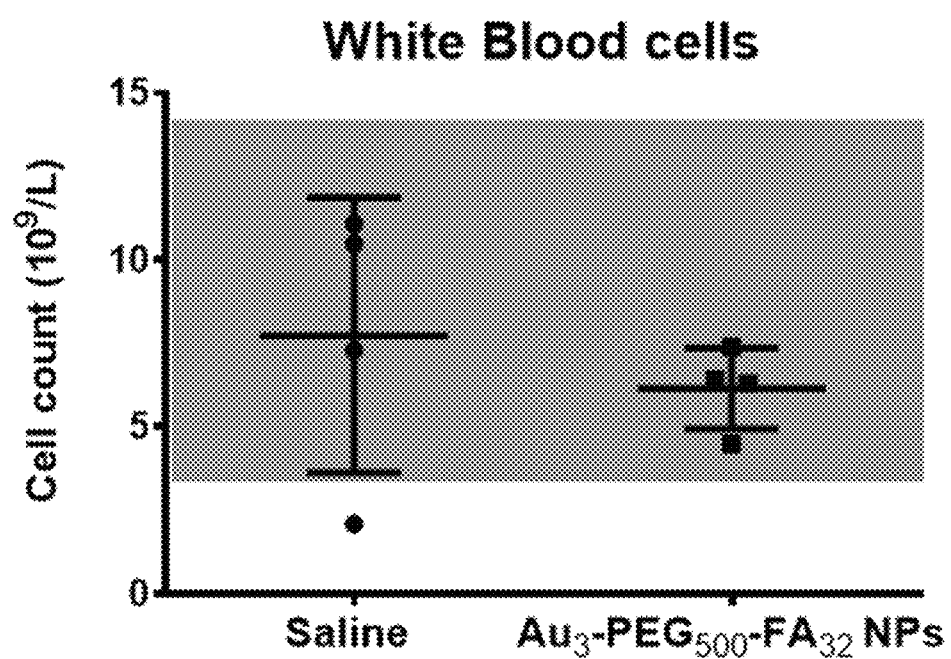
FIGS. 29A-29D Immune cell counts of white blood cells (FIG. 29A), neutrophils (FIG. 29B), lymphocytes (FIG. 29C) and monocytes (FIG. 29D) from blood drawn from UUO mice 7 days after i.v. injection of Au$_3$-PEG$_{500}$-FA$_{32}$ NPs and saline (n=4 mice/group) (or Day 14 after UUO surgery). Grey shaded area represents the normal range of cell counts for mice. Error bar denotes ±1 SD. Data are from n=4, across 1 experiment.
Figure 29B:
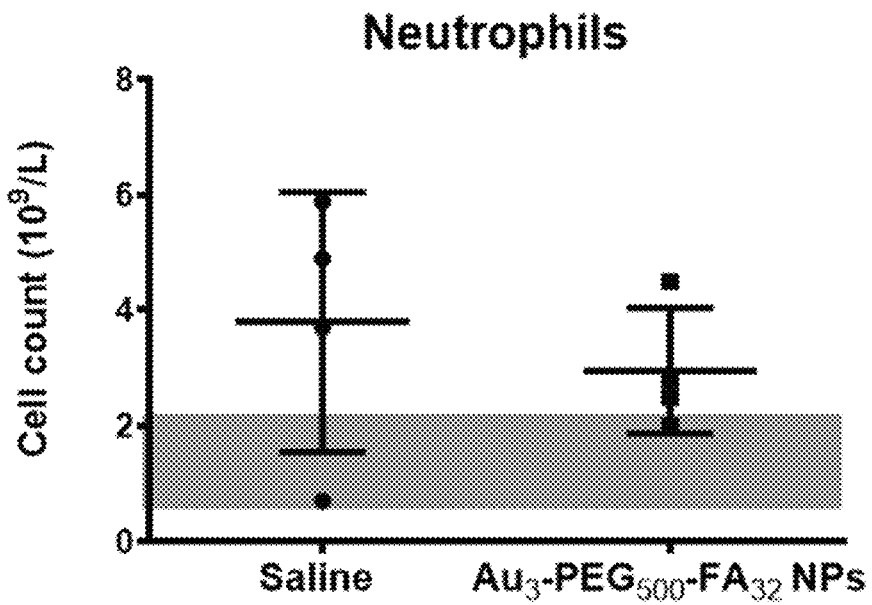
Figure 29C:
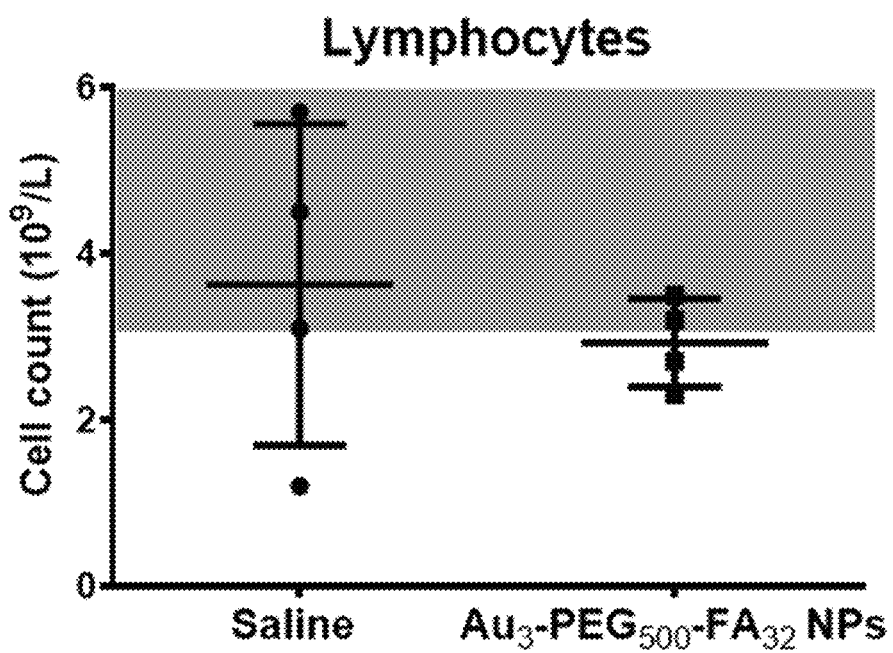
Figure 29D:
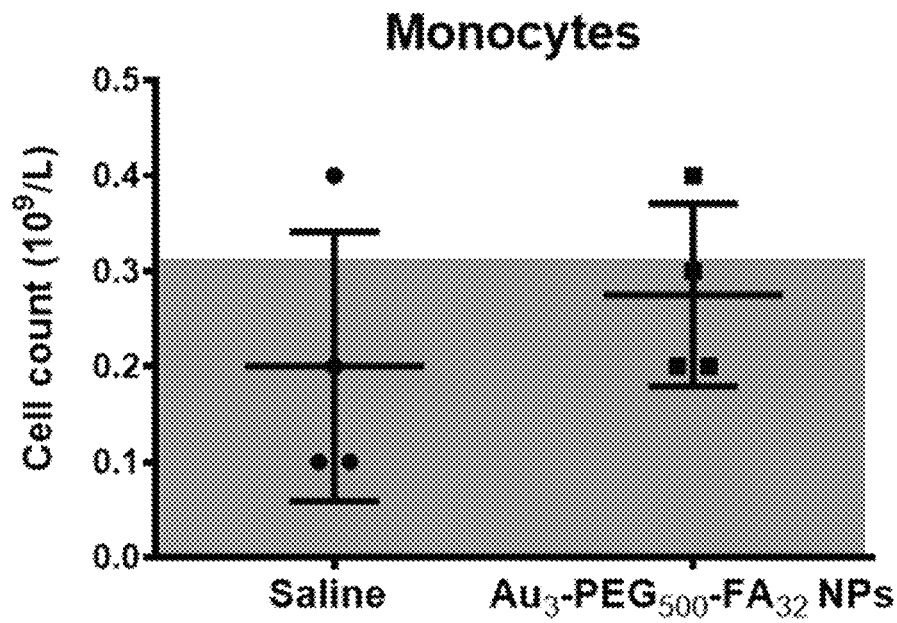
Figure 30A:
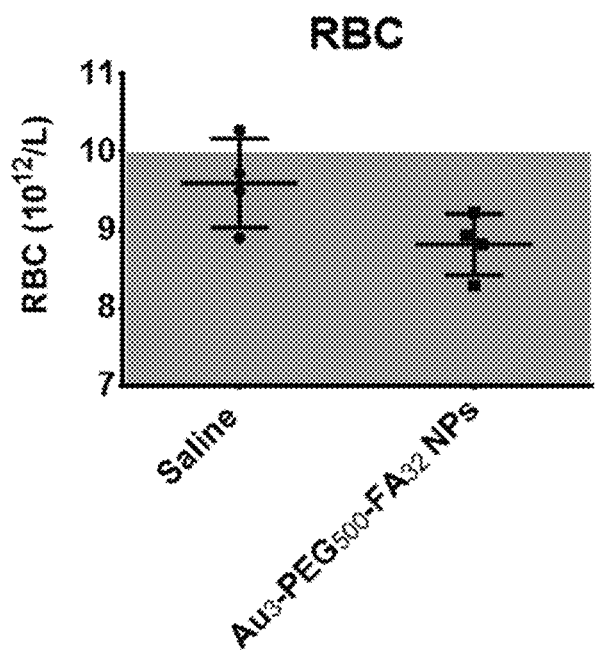
FIGS. 30A-30H Hematology analysis of UUO mice 7 days after i.v. injection of Au$_3$-PEG$_{500}$-FA$_{32}$ NPs and saline (n=4 mice/group) (or Day 14 after UUO surgery). Parameters shown include red blood cell count (RBC) (FIG. 30A), hemoglobin (FIG. 30B), hematocrit (FIG. 30C), mean corpuscular volume (MCV) (FIG. 30D), mean corpuscular hemoglobin (MCH), (FIG. 30E), mean corpuscular hemoglobin concentration (MCHC) (FIG. 30F), red cell distribution width (RDW) (FIG. 30G), and platelet count (FIG. 3011). Grey shaded area represents the normal range for mice. Error bar denotes ±1 SD. Data are from n=4, across 1 experiment.
Figure 30B:
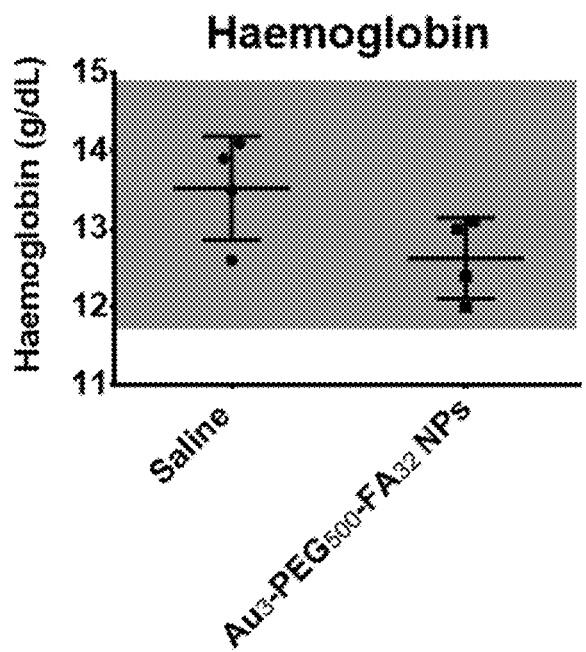
Figure 30C:
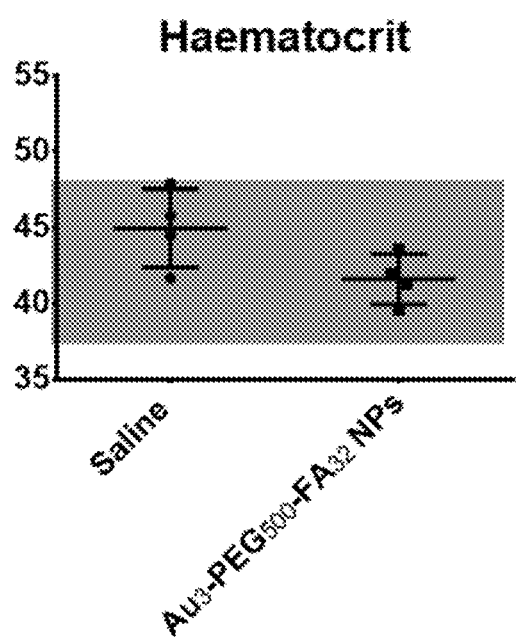
Figure 30D:
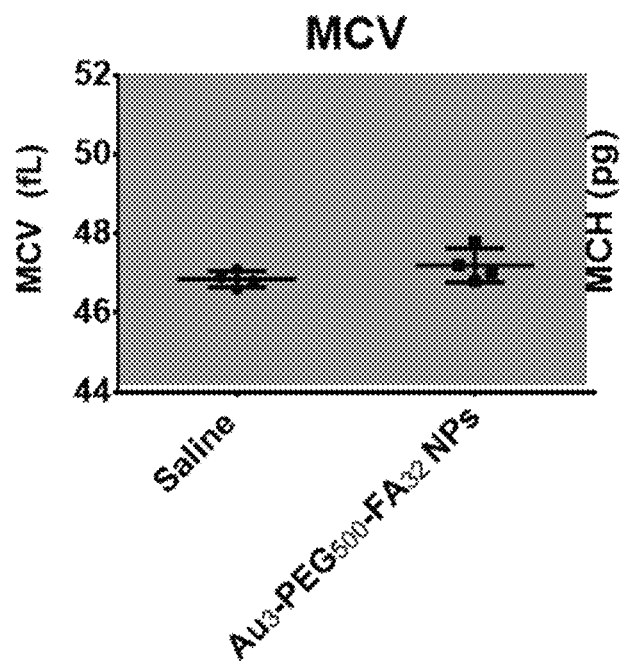
Figure 30E:
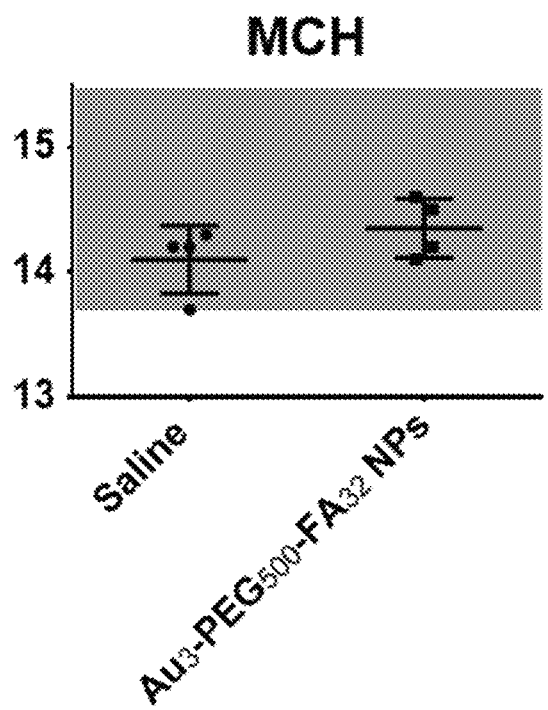
Figure 30F:
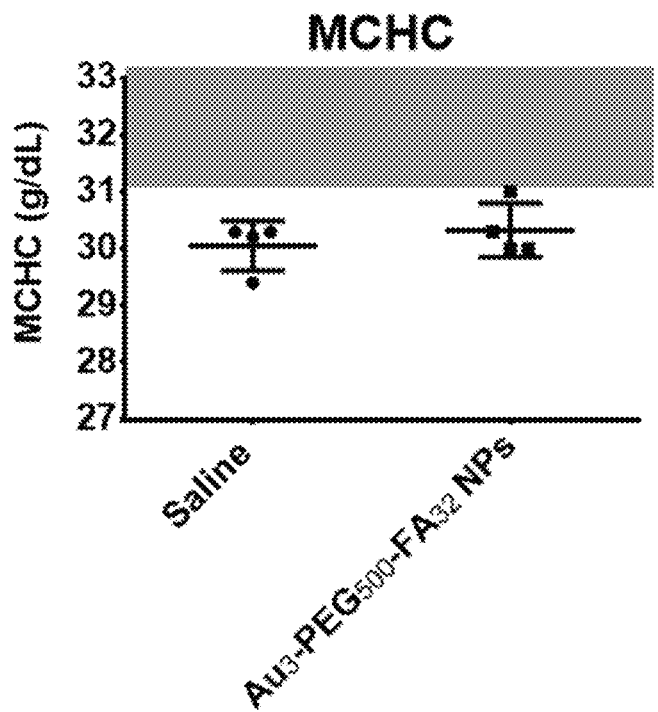
Figure 30G:
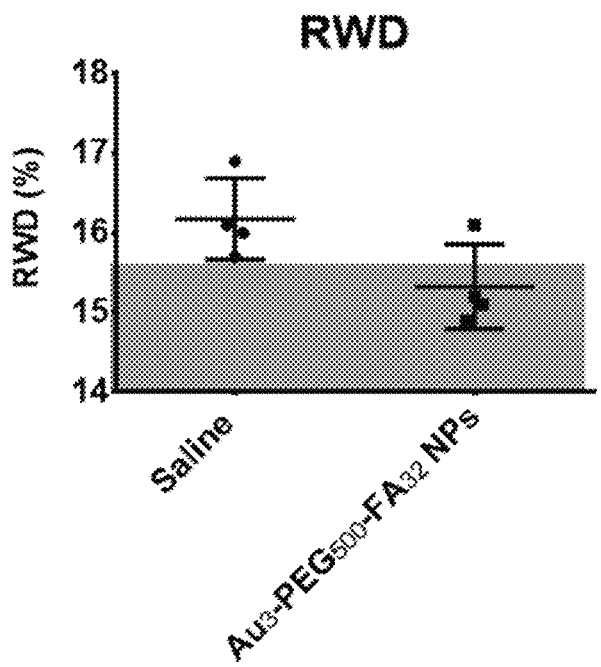
Figure 30H:
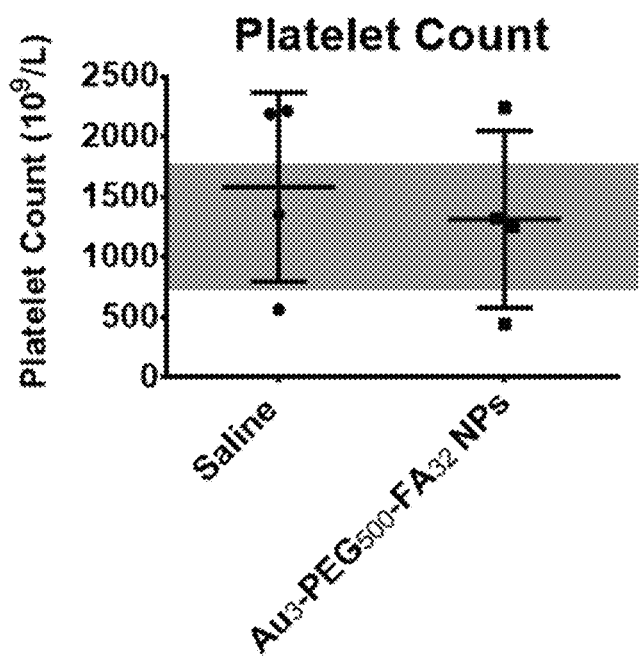
Figure 31A:
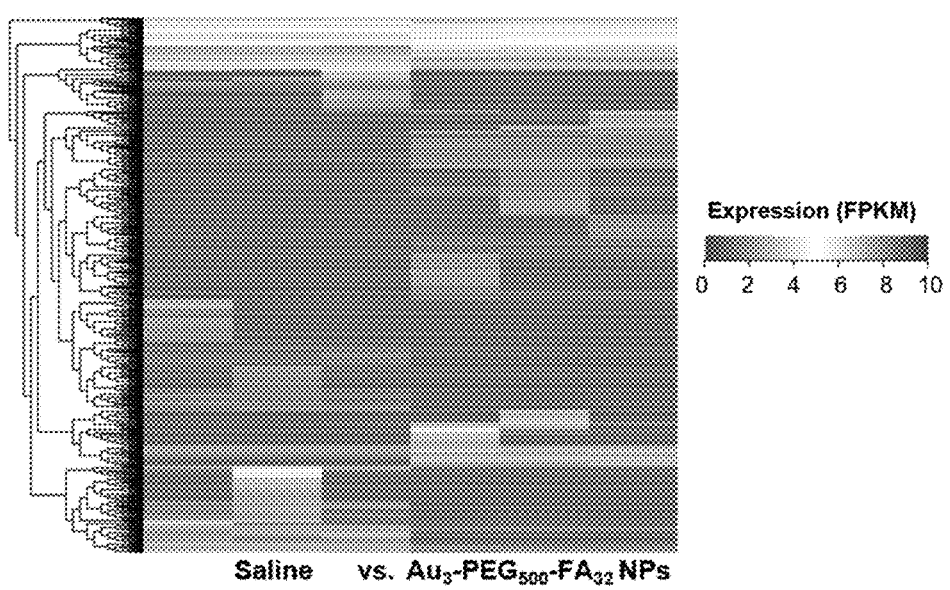
FIGS. 31A-31C Transcriptomic profile of UUO kidneys from various treatment groups.
Figure 31B:
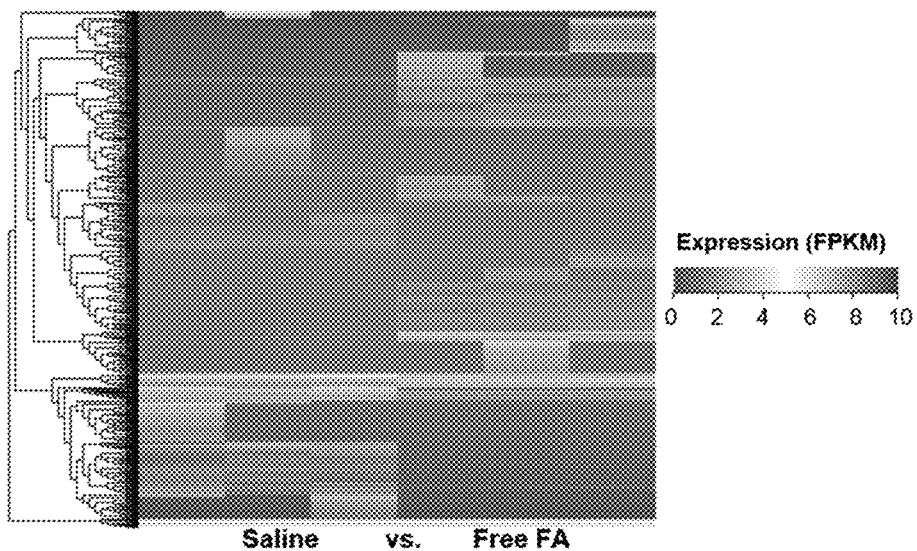
Figure 31C:
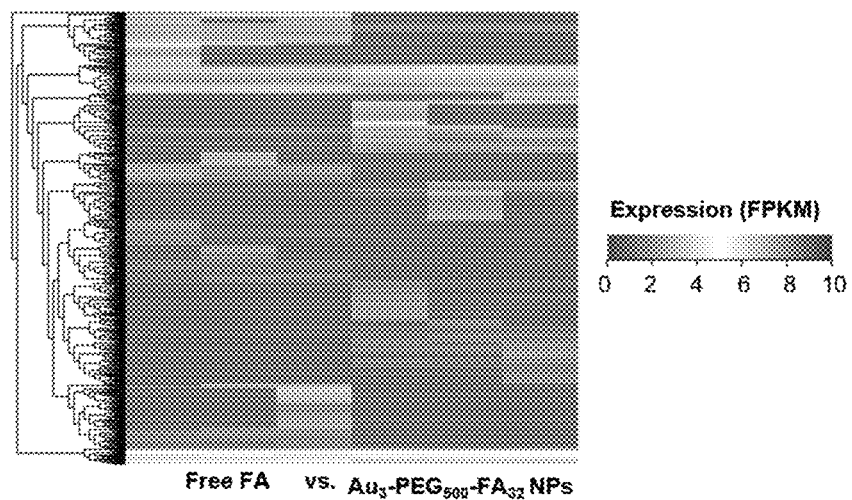
Figure 32A:
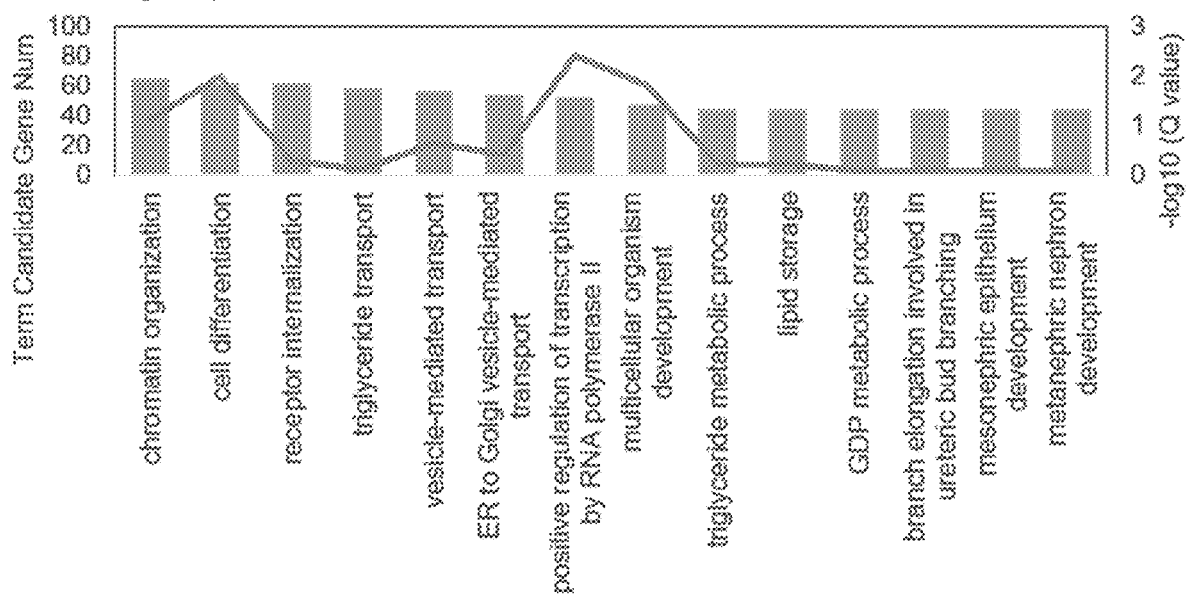
FIGS. 32A-32C Gene ontology (GO) term analysis. Statistically significant GO terms that were found in the Au$_3$-PEG$_{500}$-FA$_{32}$ NP group with reference to the free FA group as baseline (saline vs. free FA). The associated GO terms are classified three categories.
Figure 32B:
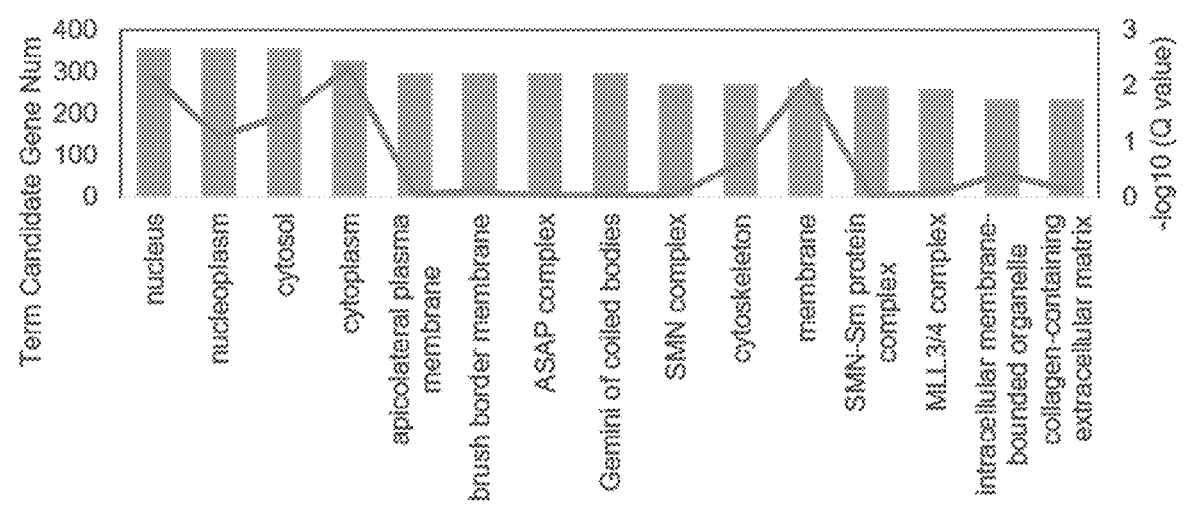
Figure 32C:
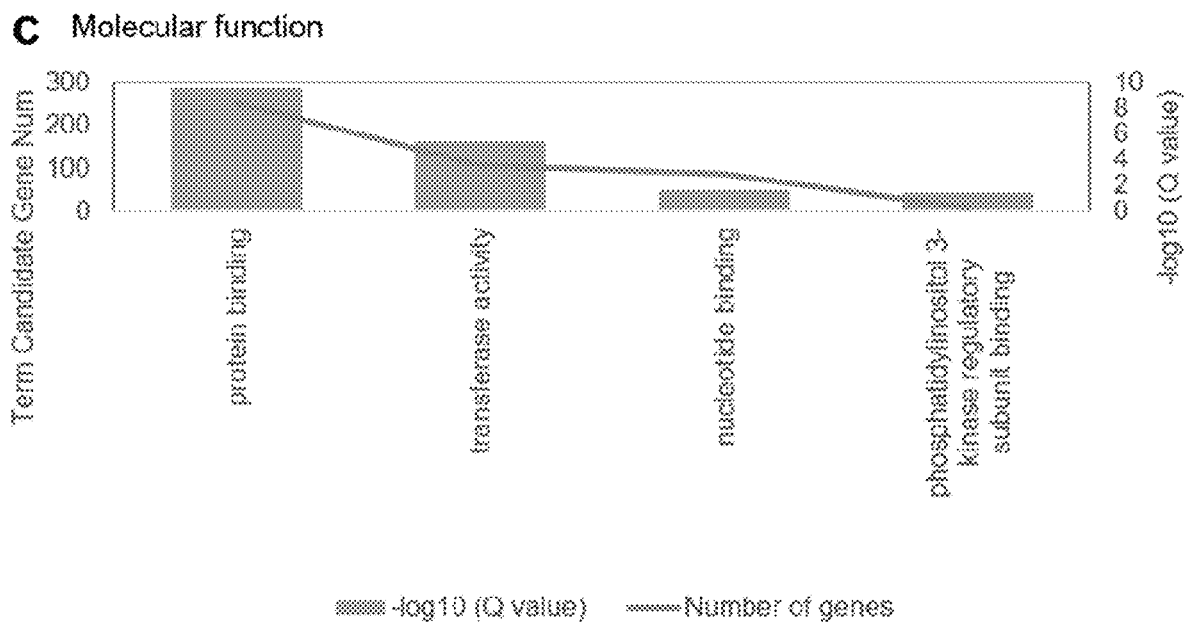
Figure 33A:
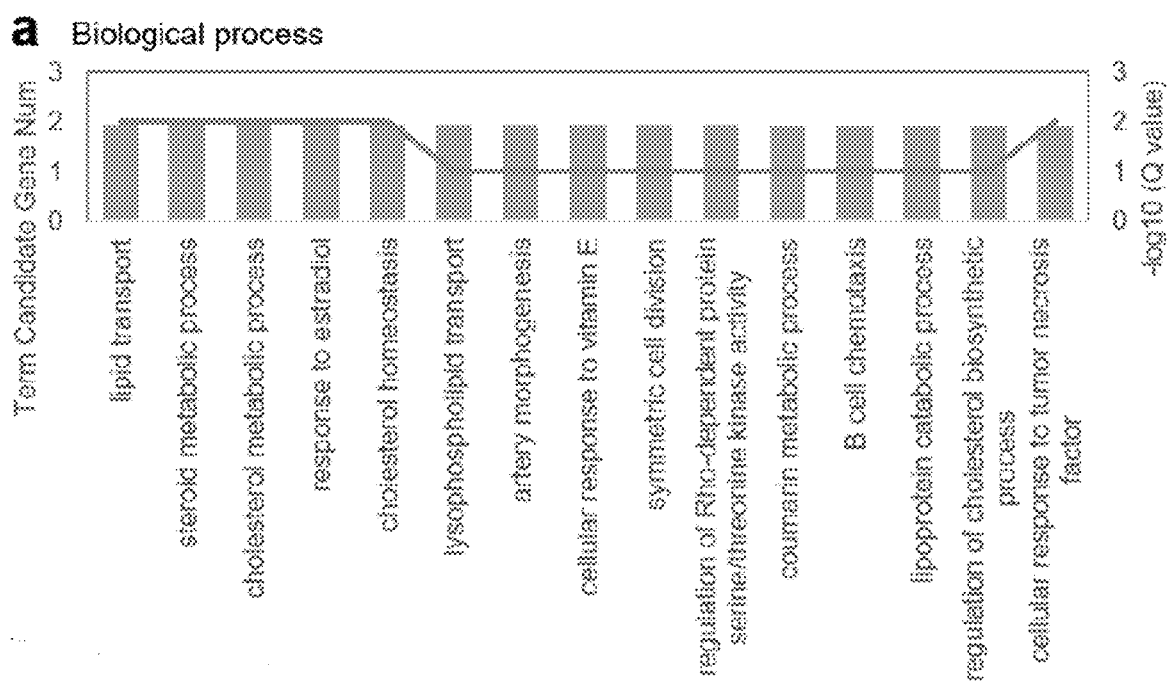
FIGS. 33A-33C Gene ontology (GO) term analysis. Statistically significant GO terms that were found in the Au$_3$-PEG$_{500}$-FA$_{32}$ NP group with reference to the saline group as baseline (saline vs. Au$_3$-PEG$_{500}$-FA$_{32}$ NP). The associated GO terms are classified three categories.
Figure 33B:
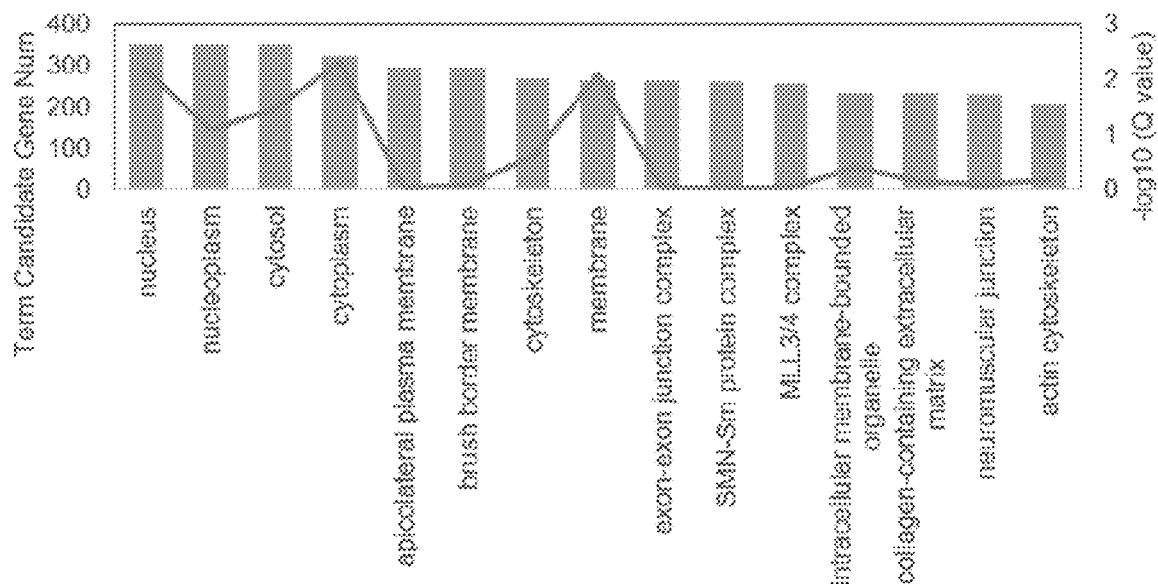
Figure 33C:
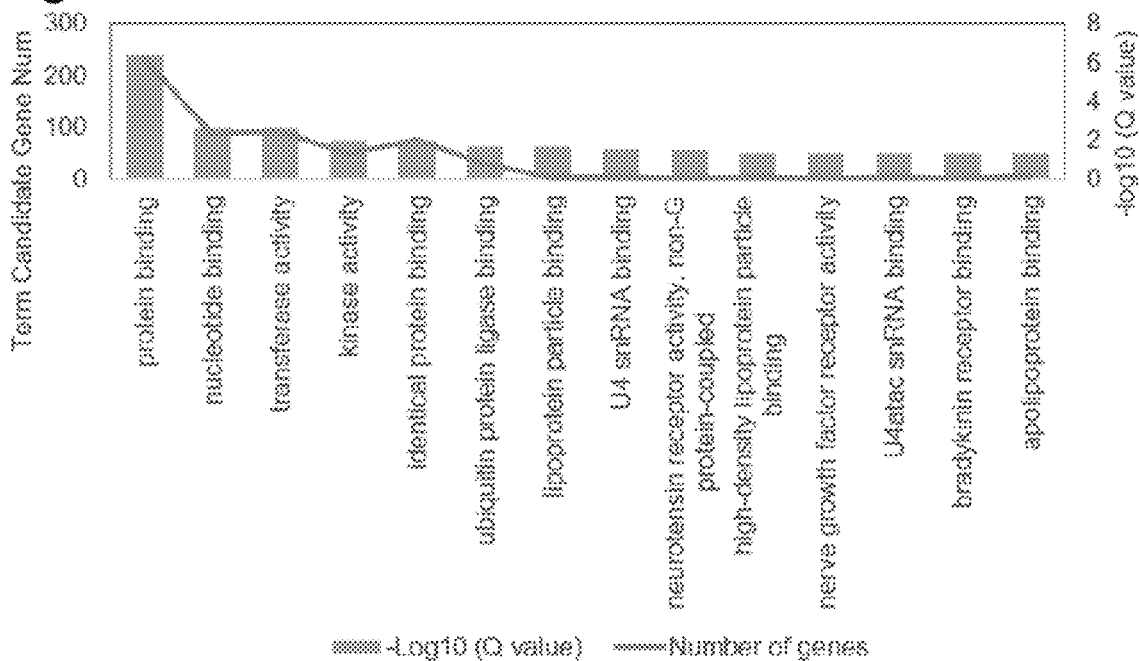
Figure 34A:
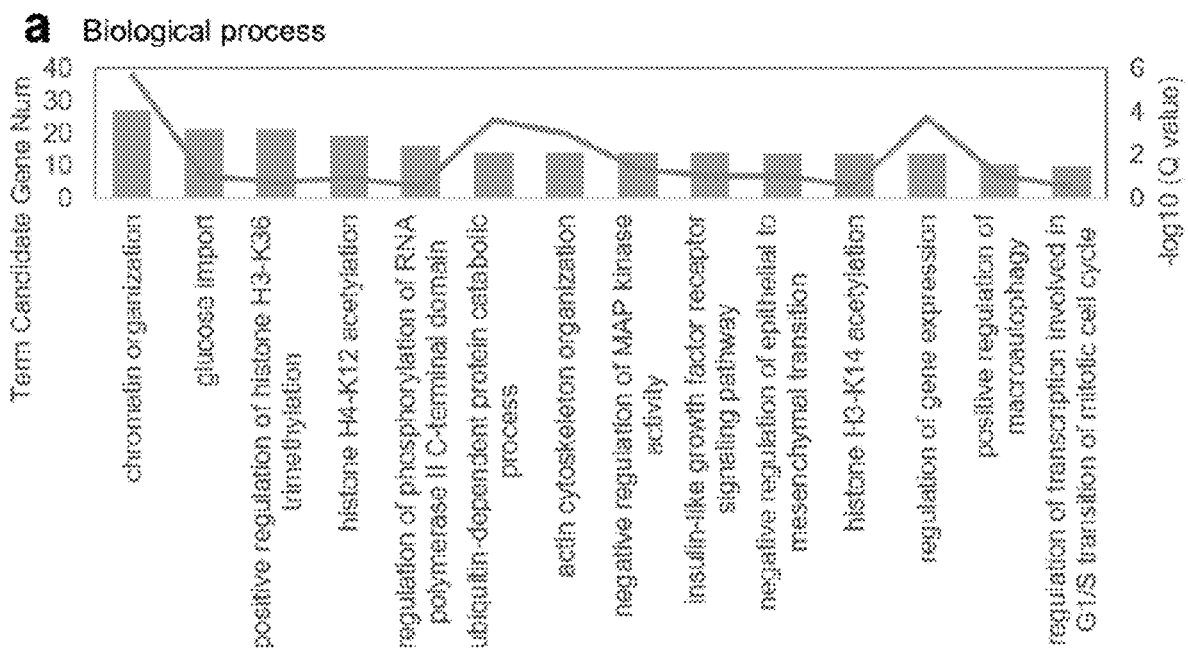
FIGS. 34A-34C Gene ontology (GO) term analysis. Statistically significant GO terms that were found in the free FA group with reference to the saline group as baseline (saline vs. free FA). The associated GO terms are classified three categories.
Figure 34B:
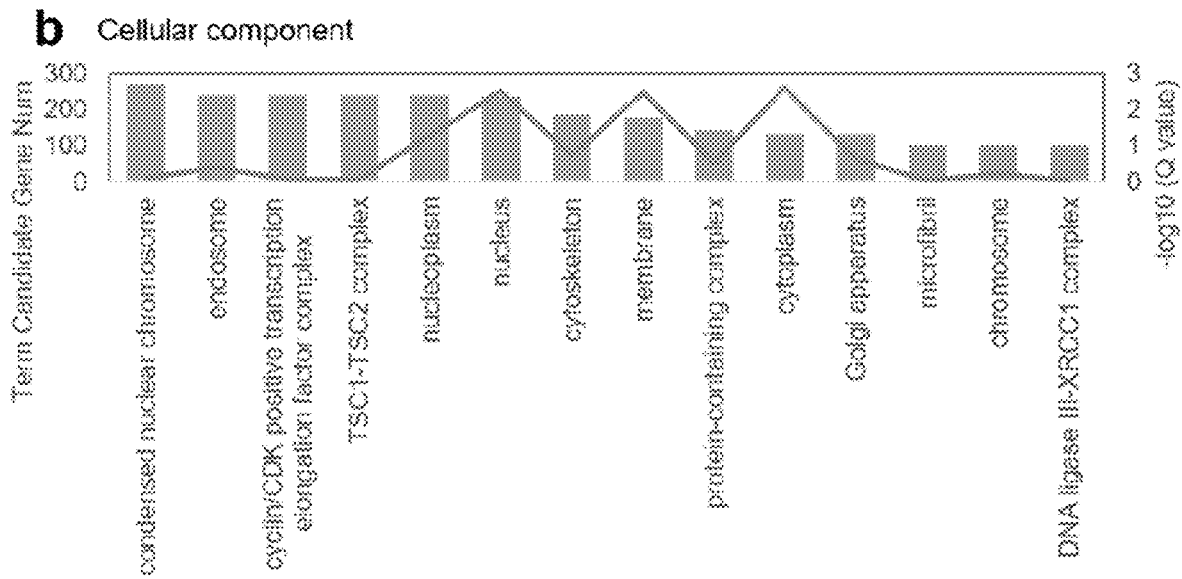
Figure 34C:
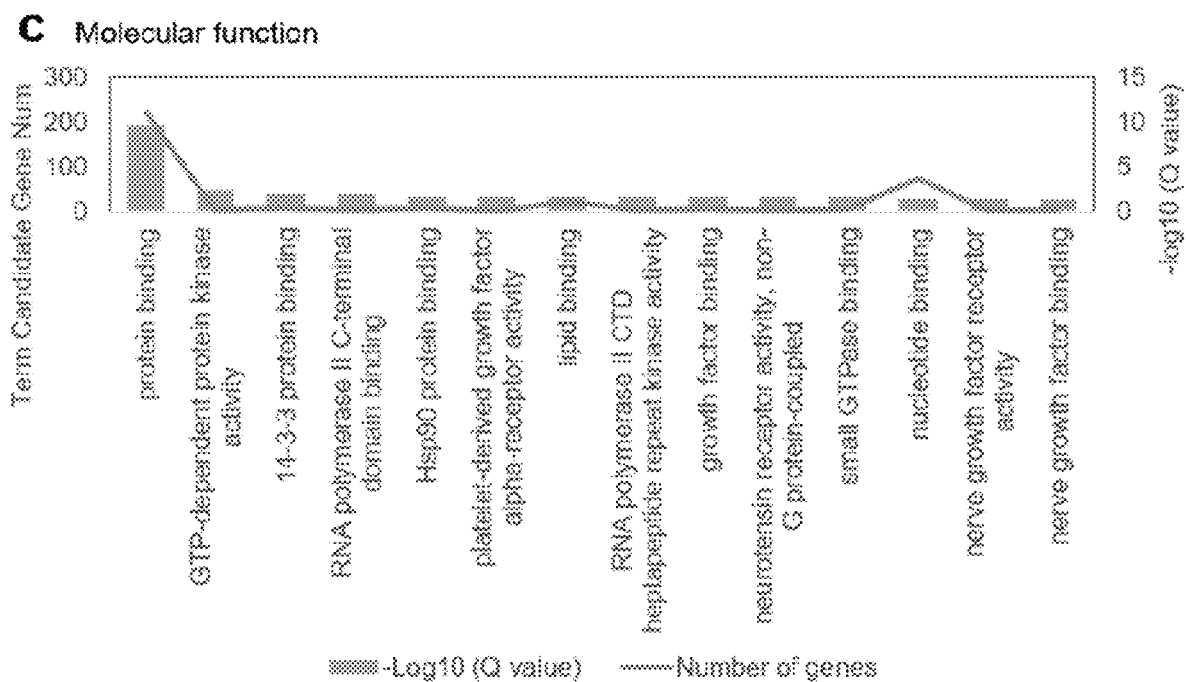

RNA-seq analysis reveals 169 differentially expressed genes (DEGs) that were enriched in both pairwise comparisons when we benchmarked the $Au_3$-$PEG_{500}$-$FA_{32}$ NP group against the saline group (saline vs. $Au_3$—$PEG_{500}$-$FA_{32}$ NP) and when we benchmarked the $Au_3$-$PEG_{500}$-$FA_{32}$ NP group against the free FA group (free FA vs. $Au_3$—$PEG_{500}$-$FA_{32}$ NP) (FIG. 27B). Notably, 19 out of these 169 genes have values of fragments per kilobase of transcript per million mapped reads (FPKM) larger than 2 in at least 6 out of the 9 UUO kidneys (from all three treatment groups) tested (FIG. 27C). The gene ontology (GO) terms associated with these 19 transcripts include collagen-containing ECM (Colec12 and Vwa5a), extracellular space (Lamb2 and Tpm1), apical membrane (Cldn7), and cell matrix adhesion (Plekha2). These data suggest that $Au_3$-$PEG_{500}$-$FA_{32}$ NPs suppressed the expression of ECM-associated components more significantly than free FA or saline.

In summary, we show that sub-10 nm NPs can cross the GBM upon i.v. injection in CKD mice. When conjugated with FA moieties, these NPs preferentially bind to FRs in the tubules of fibrotic kidneys. These data not only improve our fundamental understanding in the bio-nano interactions of NPs with diseased kidneys, but also showcase the rational design of bionanomaterials for targeting tubules and treating CKDs based on defined physiological attributes of the kidney (i.e., size cutoff of GFB and FR expression levels). Notably, a single i.v. injection of $Au_3$-$PEG_{500}$-$FA_{32}$ NPs into CKD mice significantly downregulated ECM-associated genes and reduced tissue degeneration and fibrosis without inducing toxicity. Our results reveal FA as a dual targeting ligand of FR in renal tubules and therapeutic agent for renal fibrosis; broadly, they may suggest the potential of FA-based nanomedicines for other kidney diseases. Lastly, this work highlights the treatment potential of $Au_3$-$PEG_{500}$-$FA_{32}$ NPs for renal fibrosis because our NPs were injected after the establishment of fibrosis. Most reported nanomedicines for CKD were preventive strategies that entailed injection of NPs before fibrosis was established. This point is of clinical importance; as early development of CKD is asymptomatic, patients are mostly diagnosed at a later stage of progression.

Example 13—In Vivo Toxicity of $Au_3PEG_{500}$-$FA_{32}$ NPs

Figure 26:
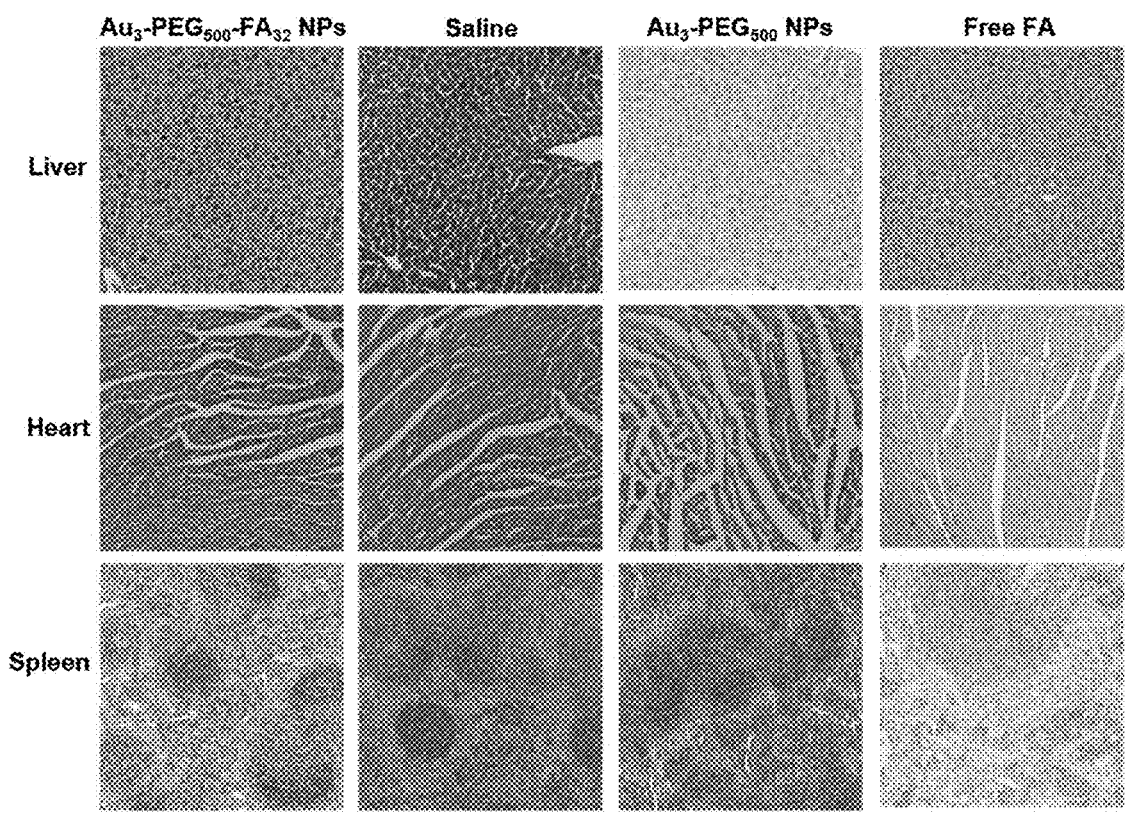
FIG. 26 shows H&E stains of the liver, heart and spleen of mice treated with Au$_3$-PEG$_{500}$-FA$_{32}$ NPs, saline, Au$_3$—PEG$_{500}$ NPs, and free folic acid.

To evaluate the in vivo toxicity of our $Au_3$-$PEG_{500}$-$FA_{32}$ NPs as the dose applied for our efficacy studies (i.e., 2.5 mg-Au/kg-mouse), the liver, heart, and spleen were collected for histological examination 7 days post-injection in UUO mice. As presented in FIG. 26, no noticeable tissue damage was observed when compared with the saline injected group. We also did not observe noticeable toxicity in mice injected with $Au_3$-$PEG_{500}$ NPs (2.5 mg-Au/kg-mouse), free FA (0.12 mg-FA/kg-mouse), or Captopril (5 mg-drug/kg-mouse/day).

To confirm the in vivo safety of $Au_3$-$PEG_{500}$-$FA_{32}$ NPs, we performed blood biochemistry tests and observed no appreciable toxicity in the liver (FIGS. 28A-28E), in agreement with the limited distribution of $Au_3$-$PEG_{500}$-$FA_{32}$ NPs to the liver (FIG. 21B).

The immune cell counts and hematology indices of mice injected with $Au_3$-$PEG_{500}$-$FA_{32}$ NPs and saline showed similar readings (FIGS. 29A-29D and 30A-30H). These data suggest that $Au_3$-$PEG_{500}$-$FA_{32}$ NPs are largely non-toxic, in line with the general understanding that non-cationic carriers are biocompatible[13]. We do not expect our therapeutic FA dosage to accelerate the development of renal fibrosis because development of AKI and CKD in rodents requires the injection of a 2000-fold higher dose of FA (250 mg/kg) to form FA crystals in the kidney[14].

To monitor the presence of bacterial endotoxins before injecting $Au_3$-$PEG_{500}$-$FA_{32}$ NPs, we verified that the endotoxin levels of our NP solution (Table 3) were exceedingly low for $Au_3$-$PEG_{500}$ and $Au_3$—$PEG_{500}$-$FA_{32}$ NPs (0.01 EU/mL and 0.003 EU/mL, respectively). In addition, the NPs endotoxin values were lower than the limits stipulated by the guidelines for pre-clinical research for injecting mice (1 EU/mL for injecting a 20-g mouse over a 24 h time period)[54].

Example 14—Validation of RNA-SEQ Data Using Type 1 Collagen as the Marker

UUO mice were i.v. injected with either $Au_3$-$PEG_{500}$-$FA_{32}$ NPs, free FA, or saline on Day 7 post-UUO surgery. Animals were sacrificed on Day 9. Their UUO kidneys were harvested for RNA extraction and subsequent RNA-seq analysis.

TABLE 4

Log2 (Fold change) comparison for type I collagen

| Gene ID | Compare group | Log2 (Fold change) | Q value |
|---|---|---|---|
| 12842 | Saline (untreated) vs. $Au_3$—$PEG_{500}$—$FA_{32}$ NPs | −0.99492 | 0.00737 |
| | Saline (untreated) vs. Free FA | −0.1405 | 0.99989 |
| | Free FA vs. $Au_3$—$PEG_{500}$—$FA_{32}$ NPs | −0.85591 | 0.99801 |

Note
that "Group X vs. Group Y" indicates statistically significant changes in RNA expression that were found in Group Y with reference to Group X as baseline.

TABLE 5

Expression level (FPKM) for type I collagen

| Gene ID | Saline | | | $Au_3$-$PEG_{500}$-$FA_{32}$ NPs | | | Free FA | | |
|---|---|---|---|---|---|---|---|---|---|
| | 1 | 2 | 3 | 1 | 2 | 3 | 1 | 2 | 3 |
| 12842 | 91.37 | 97.65 | 114.3 | 37.8 | 44.81 | 59.96 | 185.4 | 80.71 | 18.57 |

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES (1) GBD 2015 Mortality and Causes of Death Collaborators, H.; Naghavi, M.; Allen, C.; Barber, R. M.; Bhutta, Z. A.; Carter, A.; Casey, D. C.; Charlson, F. J.; Chen, A. Z.; Coates, M. M.; et al. Global, Regional, and National Life Expectancy, All-Cause Mortality, and Cause-Specific Mortality for 249 Causes of Death, 1980-2015: A Systematic Analysis for the Global Burden of Disease Study 2015. Lancet (London, England) 2016, 388, 1459-1544.
(2) Zeisberg, M.; Neilson, E. G. Mechanisms of Tubulointerstitial Fibrosis. J. Am. Soc. Nephrol. 2010, 21, 1819-1834.
(3) Williams, R. M.; Jaimes, E. A.; Heller, D. A. Nanomedicines for Kidney Diseases. Kidney Int. 2016, 90, 740-745.
(4) Yang, C.; Nilsson, L.; Cheema, M. U.; Wang, Y.; Frøkiær, J.; Gao, S.; Kjems, J.; Nørregaard, R. Chitosan/SiRNA Nanoparticles Targeting Cyclooxygenase Type 2 Attenuate Unilateral Ureteral Obstruction-Induced Kidney Injury in Mice. Theranostics 2015, 5, 110-123.
(5) Meng, X. M.; Zhang, Y.; Huang, X. R.; Ren, G. L.; Li, J.; Lan, H. Y. Treatment of Renal Fibrosis by Rebalancing TGF-β/Smad Signaling with the Combination of Asiatic Acid and Naringenin. 2015, 6, 36984-36997.
(6) Dolman, M. E. M.; Harmsen, S.; Storm, G.; Hennink, W. E. Drug Targeting to the Kidney: Advances in the Active Targeting of Therapeutics to Proximal Tubular Cells. Adv. Drug Deliv. Rev. 2010, 62, 1344-1357.
(7) Birn, H. The Kidney in Vitamin B12 and Folate Homeostasis: Characterization of Receptors for Tubular Uptake of Vitamins and Carrier Proteins. Am. J. Physiol. Renal Physiol. 2006, 291, F22-36.
(8) Zhao, X.; Li, H.; Lee, R. J. Targeted Drug Delivery via Folate Receptors. Expert Opin. Drug Deliv. 2008, 5, 309-319.
(9) Knight, S. F.; Kundu, K.; Joseph, G.; Dikalov, S.; Weiss, D.; Murthy, N.; Taylor, W. R. Folate Receptor-Targeted Antioxidant Therapy Ameliorates Renal Ischemia-Reperfusion Injury. J. Am. Soc. Nephrol. 2012, 23, 793-800.
(10) Sarin, H. Physiologic Upper Limits of Pore Size of Different Blood Capillary Types and Another Perspective on the Dual Pore Theory of Microvascular Permeability. J. Angiogenes. Res. 2010, 2, 14.
(11) Du, B.; Yu, M.; Zheng, J. Transport and Interactions of Nanoparticles in the Kidneys. Nat. Rev. Mater. 2018, 3, 358-374.
(12) Hesketh, E. E.; Vernon, M. A.; Ding, P.; Clay, S.; Borthwick, G.; Conway, B.; Hughes, J. A Murine Model of Irreversible and Reversible Unilateral Ureteric Obstruction. J. Vis. Exp. 2014, e52559.
(13) Ho, L. W. C.; Liu, Y.; Han, R.; Bai, Q.; Choi, C. H. J. Nano-Cell Interactions of Non-Cationic Bionanomaterials. Acc. Chem. Res. 2019, 52, 1519-1530.
(14) Yang, H. C.; Zuo, Y.; Fogo, A. B. Models of Chronic Kidney Disease. Drug Discovery Today: Disease Models, 2010, 7, 13-19.
(15) Liu, Y. Renal Fibrosis: New Insights into the Pathogenesis and Therapeutics. Kidney Int. 2006, 69, 213-217.
(16) Nogueira, A.; Pires, M. J.; Oliveira, P. A. Pathophysiological Mechanisms of Renal Fibrosis: A Review of Animal Models and Therapeutic Strategies. In Vivo 2017, 31, 1-22.
(17) Liu, Y. Cellular and Molecular Mechanisms of Renal Fibrosis. Nat. Rev. Nephrol. 2011, 7, 684-696.
(18) El Chaar, M.; Chen, J.; Seshan, S. V.; Jha, S.; Richardson, I.; Ledbetter, S. R.; Vaughan, E. D.; Poppas, D. P.; Felsen, D. Effect of Combination Therapy with Enalapril and the TGF-β Antagonist 1D11 in Unilateral Ureteral Obstruction. Am. J. Physiol. Physiol. 2007, 292, F1291-F1301.
(19) Gao, X.; Mae, H.; Ayabe, N.; Takai, T.; Oshima, K.; Hattori, M.; Ueki, T.; Fujimoto, J.; Tanizawa, T. Hepato-

(19) ...cyte Growth Factor Gene Therapy Retards the Progression of Chronic Obstructive Nephropathy. *Kidney Int.* 2002, 62, 1238-1248.

(20) Lan, H. Y.; Mu, W.; Tomita, N.; Huang, X. R.; Li, J. H.; Zhu, H.-J.; Morishita, R.; Johnson, R. J. Inhibition of Renal Fibrosis by Gene Transfer of Inducible Smad7 Using Ultrasound-Microbubble System in Rat UUO Model. *J. Am. Soc. Nephrol.* 2003, 14, 1535-1548.

(21) He, W.; Dai, C.; Li, Y.; Zeng, G.; Monga, S. P.; Liu, Y. Wnt/β-Catenin Signaling Promotes Renal Interstitial Fibrosis. *J. Am. Soc. Nephrol.* 2009, 20, 765-776.

(22) Tan, R. J.; Zhou, D.; Zhou, L.; Liu, Y. Wnt/β-Catenin Signaling and Kidney Fibrosis. *Kidney International Supplements*, 2014, 4, 84-90.

(23) Huo, S.; Chen, S.; Gong, N.; Liu, J.; Li, X.; Zhao, Y.; Liang, X. J. Ultrasmall Gold Nanoparticles Behavior in Vivo Modulated by Surface Polyethylene Glycol (PEG) Grafting. *Bioconjug. Chem.* 2017, 28, 239-243.

(24) Piella, J.; Bastús, N. G.; Puntes, V. Size-Controlled Synthesis of Sub-10-Nanometer Citrate-Stabilized Gold Nanoparticles and Related Optical Properties. *Chem. Mater.* 2016, 28, 1066-1075.

(25) Bastús, N. G.; Comenge, J.; Puntes, V. Kinetically Controlled Seeded Growth Synthesis of Citrate-Stabilized Gold Nanoparticles of up to 200 Nm: Size Focusing versus Ostwald Ripening. *Langmuir* 2011, 27, 11098-11105.

(26) Haiss, W.; Thanh, N. T. K.; Aveyard, J.; Fernig, D. G. Determination of Size and Concentration of Gold Nanoparticles from UV-Vis Spectra. *Anal. Chem.* 2007, 79, 4215-4221.

(27) Sarah J. Hurst; Abigail K. R. Lytton-Jean, A.; Mirkin*, C. A. Maximizing DNA Loading on a Range of Gold Nanoparticle Sizes. *Anal. Chem.* 2006, 78, 8313-8318.

(28) Ho, L. W. C.; Yung, W. Y.; Sy, K. H. S.; Li, H. Y.; Choi, C. K. K.; Leung, K. C. F.; Lee, T. W. Y.; Choi, C. H. J. Effect of Alkylation on the Cellular Uptake of Polyethylene Glycol-Coated Gold Nanoparticles. *ACS Nano* 2017, 11, 6085-6101.

(29) Chevalier, R. L.; Forbes, M. S.; Thornhill, B. A. Ureteral Obstruction as a Model of Renal Interstitial Fibrosis and Obstructive Nephropathy. *Kidney Int.* 2009, 75, 1145-1152.

(30) Takemoto, M.; Asker, N.; Gerhardt, H.; Lundkvist, A.; Johansson, B. R.; Saito, Y.; Betsholtz, C. A New Method for Large Scale Isolation of Kidney Glomeruli from Mice. *Am. J. Pathol.* 2002, 161, 799-805.

(31) Kah, J. C. Y.; Olivo, M. C.; Lee, C. G. L.; Sheppard, C. J. R. Molecular Contrast of EGFR Expression Using Gold Nanoparticles as a Reflectance-Based Imaging Probe. *Mol. Cell. Probes* 2008, 22, 14-23.

(32) Yamashita, S. Heat-Induced Antigen Retrieval: Mechanisms and Application to Histochemistry. *Prog. Histochem. Cytochem.* 2007, 41, 141-200.

(33) Veenstra, D. L., Best, J. H., Hornberger, J., Sullivan, S. D. & Hricik, D. E. Incidence and long-term cost of steroid-related side effects after renal transplantation. *Am. J. Kidney Dis.* 33, 829-839 (1999).

(34) Fried, L. F. et al. Combined angiotensin inhibition for the treatment of diabetic nephropathy. *N. Engl. J. Med.* 369, 1892-1903 (2013).

(35) Choi, C. H. J., Zuckerman, J. E., Webster, P. & Davis, M. E. Targeting kidney mesangium by nanoparticles of defined size. *Proc. Natl. Acad. Sci.* 108, 6656-6661 (2011).

(36) Zuckerman, J. E., Choi, C. H. J., Han, H. & Davis, M. E. Polycation-siRNA nanoparticles can disassemble at the kidney glomerular basement membrane. *Proc. Natl. Acad. Sci. U. S.A.* 109, 3137-42 (2012).

(37) Huang, Y., Jiang, K., Zhang, X. & Chung, E. J. The effect of size, charge, and peptide ligand length on kidney targeting by small, organic nanoparticles. *Bioeng. Transl. Med.* 5, (2020).

(38) Williams, R. M. et al. Selective nanoparticle targeting of the renal tubules. *Hypertension* 71, 87-94 (2018).

(39) Du, B. et al. Glomerular barrier behaves as an atomically precise bandpass filter in a sub-nanometre regime. *Nat. Nanotechnol.* 12, 1096-1102 (2017).

(40) Kamaly, N., He, J. C., Ausiello, D. A. & Farokhzad, O. C. Nanomedicines for renal disease: current status and future applications. *Nat. Rev. Nephrol.* 12, 738-753 (2016).

(41) Wang, J. et al. Oral delivery of metformin by chitosan nanoparticles for polycystic 375 kidney disease. *J. Control. Release* 329, 1198-1209 (2020).

(42) Huang, C. et al. Folate Receptor-Mediated Renal-Targeting Nanoplatform for the Specific Delivery of Triptolide to Treat Renal Ischemia/Reperfusion Injury. *ACS Biomater. Sci. Eng.* 5, 2877-2886 (2019).

(43) Zhang, Y. N., Poon, W., Tavares, A. J., McGilvray, I. D. & Chan, W. C. W. Nanoparticle-liver interactions: Cellular uptake and hepatobiliary elimination. *J. Control. Release* 240, 332-348 (2016).

(44) Choi, S. H. et al. Renal clearance of quantum dots. *Nat. Biotechnol.* 25, 1165-1170 392 (2007).

(45) Wu, Z., Li, X., Hou, C. & Qian, Y. Solubility of folic acid in water at pH values between 0 and 7 at temperatures (298.15, 303.15, and 313.15) K. *J. Chem. Eng. Data* 55, 3958-3961 (2010).

(46) Nestor, J. et al. Lupus antibodies induce behavioral changes mediated by microglia and blocked by ACE inhibitors. *J. Exp. Med.* 215, 2554-2566 (2018).

(47) Keppler, A. et al. Plasma creatinine determination in mice and rats: An enzymatic method compares favorably with a high-performance liquid chromatography assay. *Kidney Int.* 71, 74-78 (2007).

(48) Hesketh, E. E. et al. A murine model of irreversible and reversible unilateral ureteric obstruction. *J. Vis. Exp.* e52559 (2014). doi:10.3791/52559

(49) Dunnett, C. W. A Multiple Comparison Procedure for Comparing Several Treatments 424 with a Control. *J. Am. Stat. Assoc.* 50, 1096-1121 (1955).

(50) Yin, B. et al. Intrapulmonary Cellular-Level Distribution of Inhaled Nanoparticles with Defined Functional Groups and Its Correlations with Protein Corona and Inflammatory Response. *ACS Nano* 13, 14048-14069 (2019).

(51) Cobley, C. M., Chen, J., Cho, E. C., Wang, L. V. & Xia, Y. Gold nanostructures: a class of multifunctional materials for biomedical applications. *Chem. Soc. Rev.* 40, 44-56 (2011).

(52) Ucero, A. C. et al. Unilateral ureteral obstruction: beyond obstruction. *Int. Urol. Nephrol.* 46, 765-776 (2014).

(53) Forbes, M. S. et al. Fight-or-flight: murine unilateral ureteral obstruction causes extensive proximal tubular degeneration, collecting duct dilatation, and minimal fibrosis. *Am. J. Physiol. Renal Physiol.* 303, F120-9 (2012).

(54) Malyala, P. & Singh, M. Endotoxin limits in formulations for preclinical research. *Journal of Pharmaceutical Sciences* 97, 2041-2044 (2008).

We claim:

1. A dual function bionanomaterial for the treatment of kidney fibrosis comprising a nanoparticle comprising:
   a metal core;
   at least one polymer; and
   at least 16 dual function targeting and therapeutic molecules, wherein the size of the dual function bionanomaterial is about 5.2 nm to about 10 nm in diameter, wherein the dual function bionanomaterial is folic acid, folate, dihydrofolate, tetrahydrofolate, 10-formyl, or 5-methyl substituted folate.

2. The dual function bionanomaterial according to claim 1, wherein the metal core comprises gold, silver, nickel, iron, or platinum.

3. The dual function bionanomaterial according to claim 1, wherein the at least one polymer comprises at least one of poly(ethylene glycol), poly(ethylene oxide), poly(lactic acid), poly(glycolic acid), poly(ethylene oxide)-poly(lactic acid), poly(ethylene oxide)-poly(glycolic acid), poly(glycolic acid)-poly(lactic acid), sodium alginate, dextran, and poloxamers.

4. The dual function bionanomaterial according to claim 3, wherein the at least one polymer is a mixture of at least two of poly(ethylene glycol), poly(ethylene oxide), poly(lactic acid), poly(glycolic acid), poly(ethylene oxide)-poly(lactic acid), poly(ethylene oxide)-poly(glycolic acid), poly(glycolic acid)-poly(lactic acid), sodium alginate, dextran, and poloxamers.

5. The dual function bionanomaterial according to claim 1, wherein the at least 16 dual function targeting and therapeutic molecules are folic acid molecules.

6. The dual function bionanomaterial according to claim 5, wherein the at least 16 folic acid molecules are present on the surface of the nanoparticle.

7. The dual function bionanomaterial according to claim 1, comprising 16 or 32 dual function targeting and therapeutic molecules.

8. The dual function bionanomaterial according to claim 7, wherein the 16 or 32 dual function targeting and therapeutic molecules are folic acid molecules.

9. The dual function bionanomaterial according to claim 8, wherein the 16 or 32 folic acid molecules are present on the surface of the nanoparticle.

10. A method of treating a kidney disease in a subject comprising administering at least one therapeutically effective amount of a dual function bionanomaterial according to claim 1 to the subject.

11. The method according to claim 10, wherein the dual function bionanomaterial is administered by intravenous, oral, rectal, bronchial, nasal, topical, buccal, sub-lingual, transdermal, vaginal, intramuscular, intraperitoneal, intra-arterial, intracerebral, or intraocular administration.

12. The method according to claim 11, wherein the dual function bionanomaterial is administered by intravenous administration.

13. The method according to claim 10, wherein the kidney disease is kidney fibrosis.

14. The method according to claim 10, further comprising administering at least one additional therapeutically effective amount to the subject.

15. The method according to claim 14, wherein the at least one therapeutically effective amount and the at least one additional therapeutically effective amount are administered less than 48 hours apart and/or more than 21 days apart.

16. The dual function bionanomaterial according to claim 1, wherein the metal core comprises gold.

17. The dual function bionanomaterial according to claim 1, wherein the at least one polymer has a molecular weight of about 500 Da to about 1000 Da.

18. The dual function bionanomaterial according to claim 17, wherein the at least one polymer comprises at least one of poly(ethylene glycol).

* * * * *